(12) United States Patent
Fischer et al.

(10) Patent No.: US 7,179,612 B2
(45) Date of Patent: Feb. 20, 2007

(54) METHOD FOR DETECTING A LIPOPROTEIN-ACUTE PHASE PROTEIN COMPLEX AND PREDICTING AN INCREASED RISK OF SYSTEM FAILURE OR MORTALITY

(75) Inventors: Timothy J. Fischer, Raleigh, NC (US); Colin Downey, Liverpool (GB); Mike Nesheim, Kingston (CA); John A. Samis, Kingston (CA); Liliana Tejidor, Coral Gables, FL (US); Cheng-Hock Toh, Liverpool (GB); John B. Walker, Edmonton (CA)

(73) Assignee: bioMerieux, Inc., Durham, NC (US)

( * ) Notice: Subject to any disclaimer, the term of this patent is extended or adjusted under 35 U.S.C. 154(b) by 265 days.

(21) Appl. No.: 10/019,087

(22) PCT Filed: Jun. 8, 2001

(86) PCT No.: PCT/US01/18611

§ 371 (c)(1),
(2), (4) Date: Dec. 19, 2001

(87) PCT Pub. No.: WO01/96864

PCT Pub. Date: Dec. 20, 2001

(65) Prior Publication Data

US 2002/0193949 A1  Dec. 19, 2002

Related U.S. Application Data

(63) Continuation of application No. 09/591,642, filed on Jun. 9, 2000, now abandoned.

(51) Int. Cl.
*G01N 33/536* (2006.01)
*G01N 33/537* (2006.01)
*G01N 33/539* (2006.01)
*G01N 55/564* (2006.01)
*C12Q 1/60* (2006.01)

(52) U.S. Cl. .................. 435/11; 436/507; 436/515; 436/516; 436/517

(58) Field of Classification Search .................. 436/69, 436/71, 34, 164, 517, 536, 805, 80; 435/11
See application file for complete search history.

(56) References Cited

U.S. PATENT DOCUMENTS

| | | | |
|---|---|---|---|
| 3,307,392 A | 3/1967 | Owen et al. |
| 3,458,287 A | 7/1969 | Gross et al. |
| 3,658,480 A | 4/1972 | Kane et al. |
| 4,040,788 A | 8/1977 | Simons et al. |
| 4,047,890 A | 9/1977 | Eichelberger et al. |
| 4,199,748 A | 4/1980 | Bacus |
| 4,217,107 A | 8/1980 | Saito et al. |
| 4,279,616 A | 7/1981 | Saito et al. |
| 4,289,498 A | 9/1981 | Baughman et al. |
| 4,766,083 A | 8/1988 | Miyashita et al. |
| 4,782,014 A | 11/1988 | Serban et al. |
| 4,902,630 A | 2/1990 | Bennett et al. |
| 4,965,725 A | 10/1990 | Rutenberg |
| 4,998,535 A | 3/1991 | Selker et al. |
| 5,003,065 A | 3/1991 | Merritt et al. |
| 5,055,412 A | 10/1991 | Proksch |
| 5,156,974 A | 10/1992 | Grossman et al. |
| 5,218,529 A | 6/1993 | Meyer et al. |
| 5,221,628 A | 6/1993 | Anderson et al. |
| 5,358,852 A | 10/1994 | Wu |
| 5,388,164 A | 2/1995 | Yonekawa et al. |
| 5,473,551 A | 12/1995 | Sato et al. |
| 5,473,732 A | 12/1995 | Chang |
| 5,500,345 A | 3/1996 | Soe et al. |
| 5,506,146 A | 4/1996 | Josef |
| 5,525,477 A | 6/1996 | Hassouna |
| 5,526,111 A | 6/1996 | Collins et al. |
| 5,553,616 A | 9/1996 | Ham et al. |
| 5,563,983 A | 10/1996 | Nozaki et al. |
| 5,567,596 A | 10/1996 | Diamond et al. |
| 5,591,403 A | 1/1997 | Gavin et al. |
| 5,593,897 A | 1/1997 | Potempa et al. |
| 5,646,046 A | 7/1997 | Fischer et al. |
| 5,670,329 A | 9/1997 | Oberhardt |
| 5,705,395 A | 1/1998 | Griffin et al. |
| 5,708,591 A | 1/1998 | Givens et al. |

(Continued)

FOREIGN PATENT DOCUMENTS

DE    2635081    2/1978

(Continued)

OTHER PUBLICATIONS

Stryer et al, in Biochemistry, Third edition, W H Freeman Company, New York, pp. 31-33, 1998.*

(Continued)

*Primary Examiner*—Christina Chan
*Assistant Examiner*—Phuong Huynh
(74) *Attorney, Agent, or Firm*—Myers Bigel Sibley & Sajovec, P.A.

(57) ABSTRACT

A method for diagnosing a condition of a patient involves the steps of (a) adding one or more reagents to a test sample from a patient, the test samples comprising at least part of a blood sample from the patient, in order to cause formation of a complex comprising at least one acute phase protein and at least one human lipoprotein, while causing substantially no fiber polymerization; (b) measuring the formation of the complex over time so as to derive a time-dependent measurement profile, and (c) determining a slope and/or total change in the time-dependent measurement profile, so as to diagnose a condition of the patient. A greater formation of the complex is correlated to increased probability of death of the patient.

5 Claims, 32 Drawing Sheets

U.S. PATENT DOCUMENTS

| | | | |
|---|---|---|---|
| 5,715,821 | A | 2/1998 | Faupel |
| 5,716,795 | A | 2/1998 | Matschiner |
| 5,834,223 | A | 11/1998 | Griffin et al. |
| 5,856,114 | A | 1/1999 | Mann et al. |
| 5,862,304 | A | 1/1999 | Ravdin et al. |
| 5,981,285 | A | 11/1999 | Carroll et al. |
| 6,010,911 | A | 1/2000 | Baugh et al. |
| 6,040,147 | A | 3/2000 | Ridker et al. |
| 6,101,449 | A | 8/2000 | Givens et al. |
| 6,156,530 | A | 12/2000 | R.ang.nby |
| 6,269,313 | B1 | 7/2001 | Givens et al. |
| 6,321,164 | B1 | 11/2001 | Braun et al. |
| 6,429,017 | B1 * | 8/2002 | Toh et al. ..................... 436/69 |

FOREIGN PATENT DOCUMENTS

| | | |
|---|---|---|
| DE | 3502 878 | 1/1985 |
| EP | 0 115 459 | 8/1984 |
| EP | 0 434 377 | 6/1991 |
| EP | 0 525 273 | 2/1993 |
| EP | 818 680 | 1/1998 |
| EP | 841 566 | 5/1998 |
| FR | 2364 453 | 9/1976 |
| GB | 2005014 | 4/1979 |
| JP | 59-203959 | 11/1984 |
| JP | 60-114768 | 6/1985 |
| JP | 61-272655 | 12/1986 |
| JP | 05-180835 | 12/1991 |
| JP | 06-027115 | 7/1992 |
| JP | 04-254760 | 9/1992 |
| JP | 06-249855 | 9/1994 |
| JP | 10-104239 | 9/1996 |
| RU | 2012877 | 4/1991 |
| RU | 2061953 | 6/1996 |
| RU | 2070327 | 12/1996 |
| SU | 590665 | 2/1976 |
| SU | 1076086 | 2/1984 |
| SU | 1691741 | 8/1989 |
| SU | 1777089 | 6/1990 |
| WO | WO 86/06840 | 11/1986 |
| WO | WO 89/09628 | 10/1989 |
| WO | WO 91/00872 | 1/1991 |
| WO | WO 91/01383 | 2/1991 |
| WO | WO 91/01497 | 2/1991 |
| WO | WO 91/02812 | 3/1991 |
| WO | WO 91/05874 | 5/1991 |
| WO | WO 91/08460 | 6/1991 |
| WO | WO 91/16453 | 10/1991 |
| WO | WO 93/07491 | 4/1993 |
| WO | WO 93/09438 | 5/1993 |
| WO | WO 93/24530 | 12/1993 |
| WO | WO 94/07145 | 3/1994 |
| WO | WO 94/11714 | 5/1994 |
| WO | WO 94/16095 | 7/1994 |
| WO | WO 95/05590 | 2/1995 |
| WO | WO 95/08121 | 3/1995 |
| WO | WO 96/42018 | 9/1995 |
| WO | WO 95/30154 | 11/1995 |
| WO | WO 96/06624 | 3/1996 |
| WO | WO 96/14581 | 5/1996 |
| WO | WO 96/21740 | 7/1996 |
| WO | WO 96/41291 | 12/1996 |
| WO | WO 97/04317 | 2/1997 |
| WO | WO 97/20066 | 6/1997 |
| WO | WO 97/34698 | 9/1997 |
| WO | WO 98/09628 | 3/1998 |
| WO | WO 99/34208 | 7/1999 |
| WO | WO 99/47699 | 9/1999 |

OTHER PUBLICATIONS

Ngo et al, 1994, The Protein Folding Problem and Tertiary Structure Prediction, pp. 492-495.*
Kuby et al., 1994, Immunology, second edition, pp. 85-96.*
Row et al, Clin Exp Immunol 58(1): 237-44, 1984.*
Li et al, Biochemical and Biophys Research Communications 224: 249-252, 1998.*
Ridker et al, Circulation 97: 2007-2011, 1998.*
Artherotech, *VAP/CAD Lipoprotein Risk Assessment Test and Sample of VAP Profile*, http://www.artherotech.com/risk_assessment.html.
Cabana, et al., Effects of the acute phase response on the concentration and density distribution of plasma lipids and apolipoproteins, *J. Lipid Res.*, 30:39-49 (1989).
Cabana, et al., Inflammation-induced changes in rabbit CRP and plasma lipoproteins, *J. Immunol.*, 130(4):1736-1742 (Apr. 1983).
Lindh, et al., Agglutinate formation in serum samples mixed with intravenous fat emulsions, *Crit Care Med.*, 13(3):151-154 (Mar. 1985).
Malle, et al., Serum amyloid A (SAA): an acute phase protein and apolipoprotein, *Atherosclerosis*, 102:131-146 (1993).
Maury et al., Clinical usefulness of serum amyloid A and C-reactive protein measurements in inflammatory disorders a comparative study, *Market Proteins in Inflammation Proceedings, Symposium*, Lyon, France, 3:Abstract only-(1985), 153-156.
McCarty, M., Historical perspective on C-reactive protein, *Ann N.Y. Acad Sci.*, 389:1-10 (1982).
McDonald, et al., A monoclonal antibody sandwich immunoassay for serum amyloid A (SAA) protein, *J. Immunol. Methods*, 144:149-155 (Nov. 22, 1991).
Pepys, et al., C-reactive protein: binding to lipids and lipoproteins, *Int Rev.Exp.Pathol.*, 27:83-111 (1985).
Preciado-Pratt et al. et al., Serum amyloid A complexed with extracellular matrix induces the secretion of tumor necrosis factor-alpha by human T-lymphocytes, *Letters in Peptide Science*, 5:349-355 (Oct. 1988).
Richter, et al., The fat emulsion agglutination test: a reliable and cost effective alternative to the latex agglutination test for rapid bedside CRP measurement, *Clin. Chim. Acta*, 261:141-148 (May 1997).
Robin et al., Prognostic value of waveform analysis in the intensive care setting, *Intensive Care Med.*, 25(Suppl 1):S63 (1999).
Rowe, et al., Agglutination of intravenous lipid emulsion ('Intralipid') and plasma lipoproteins by C-reactive protein, *Clin. Exp. Immunol.*, 66:241-247 (1986).
Rowe, et al., Circulating human C-reactive protein binds very low density lipoproteins, *Clin.Exp.Immunol.*, 58:237-244 (1984).
Rowe, et al., *In vivo* turnover studies of C-reactive protein and lipoproteins in the rabbit, *Clin.Exp.Immunol.*, 58:245-252 (1984).
Rowe, et al., Rabbit and rat C-reactive proteins bind apolipoprotein B-containing lipoproteins, *J.Exp.Med.*, 159:604-616 (Feb. 1984).
Rybarska, J., Konieczny, L., Piekarska, B., Stopa, B., and Roterman, I. et al., The detection of specific acute phase serum protein complexes and immune complexes by congo red binding, *J.Physiol Pharmacol.*, 46(2):221-231 (Jun. 1995).
Sammalkorpi, et al., Lipoproteins and acute phase response during acute infection. Interrelationships between C-reactive protein and serum amyloid-A protein and lipoproteins, *Ann Med.*, 22:397-401 (1990).
Cabana, et al., Interaction of very low density lipoproteins (VLDL) with rabbit C-reactive protein, *J Immunol.*, 128(5):2342-2348 (May 1982).
Canivet, et al., Postoperative changes in lipid profile: their relations with inflammatory markers and endocrine mediators, *Acta Anaesthesiol Belg.*, 40(4):263-268 (1989).
Christner and Mortensen, Specificity of the binding interaction between human serum amyloid P-component and immobilized human C-reactive protein, *J.Biol.Chem.*, 269(13):9760-9766 (Apr. 1994).
de Beer, et al., Low density lipoprotein and very low density lipoprotein are selectively bound by aggregated C-reactive protein, *J.Exp.Med.*, 156:230-242 (Jul. 1982).

Dennis et al., Utility of prothrombin time waveform analysis in the routine clinical setting, *Abstract Instruction and Submission Form*, (Sep. 1999).

Downey et al., Transmittance waveforms—adjunctive information from automated coagulometers, *Int.J.Hematol.*, 64 Suppl:S160, Abstract #619, (Aug. 1996).

Downey, et al., Novel and diagnostically applicable information from optical waveform analysis of blood coagulation in disseminated intravascular coagulation, *Br.J.Haematol.*, 98:68-73 (1997).

Eitoku et al. et al., Studies on the serum amyloid A (SAA): Part 2 latex agglutination nephelometric immunoassay system for the quantitation of SAA in human serum and its clinical values, *Physico.Chem.Biol.*, 37:19-23 (Feb. 1993).

Engler, R., [Acute-phase proteins in inflammation], *C.R. Seances Soc. Biol. Fil.*, 189(4):563-578 (1995).

Gewurz, et al., C-reactive protein and the acute phase response, *Adv.Intern.Med.*, 27:345-372 (1982).

Harris et al., Reactivity of serum amyloid P component with C-reactive protein and IgM, *Clin. Res.*, 37, Abstract #614A (1989).

Hulman and Fuller, Comparison of fat agglutination slide test and latex test for C- reactive protein, *Clin.Chim.Acta*, 165:89-93 (May 29, 1987).

Hulman, et al., Agglutination of intralipid by sera of acutely ill patients, *Lancet*, 2:1426-1427 (Dec. 1982).

Hulman, G., The pathogenesis of fat embolism, *J Pathol.*, 176:3-9 (1995).

Husebekk, et al., High-density lipoprotein has different binding capacity for different apoproteins. The amyloidogenic apoproteins are easier to displace from high-density lipoprotein, *Scand.J.Immunol.*, 28:653-658 (1988).

Lagrand, et al., C-reactive protein as a cardiovascular risk factor: more than an epiphenomenon?, *Circulation*, 100:96-102 (Jul. 1999).

Schwalbe, et al., Association of rat C-reactive protein and other pentraxins with rat lipoproteins containing apolipoproteins E and A1, *Biochemistry*, 34(33):10432-10439 (Aug. 1995).

Simmons, A. Ethanol-gel solubility test, In: *Technical Hematology*, 3rd Edition, J.B. Lippincott Company, Philadelphia, PA, p. 334-335 (1980).

Stewart, et al., Sensitive and rapid measurement of C-reactive protein (CRP) by lipid agglutination, *J.Clin.Pathol.*, 40:585-588 (1987).

Swanson, et al., Human serum amyloid P-component (SAP) selectively binds to immobilized or bound forms of C-reactive protein (CRP), *Biochim Biophys Acta*, 1160:309-316 (Dec. 28, 1992).

Toh and Downey, A previously unrecognized mechanism that is calcium-dependent and thrombin-independent characterizes the pre-DIC state, *The American Society of Hematology, 1999 Submission Form*, Abstract #450426 (1999).

Toh and Downey, The mechanism underlying the atypical clot waveform profile of DIC is thrombin-independent but calcium-dependent, *European Haematology Association, Abstract Form* (Jun. 2000).

Toh et al., APTT Waveform analysis: predicting mortality in the critical care setting using the light transmittance level at 18 seconds, *XVII Congress International Society for Thrombosis & Haemostasis, Abstract Submission Form*, (Aug. 1999).

Toh et al., Impending clinical decompensation is characterized by the detection of a novel calcium-dependent and thrombin-independent pathway, *5th World Congress on Trauma, Shock, Inflammation and Sepsis—Pathophysiology, Immune Consequences and Therapy, Abstract Submission Form*, (Feb. 2000).

Toh et al., Prospective detection of pre-disseminated intravascular coagulation (DIC) in a sepsis cohort by waveform analysis, *XVII Congress International Society for Thrombosis & Haemostasis, Abstract Submission Form*, (Aug. 1999).

Toh et al., Waveform analysis of the prothrombin time (PT) assay also shows characteristic changes in disseminated intravascular coagulation, *XVII Congress International Society for Thrombosis & Haemostasis, Abstract Submission Form*, (Aug. 1999).

Toh, C.H., Disseminated intravascular coagulation (DIC): Old problem, new hope, *Clin Hemostasis Rev.*, p. 18 (Jan. 1998).

Wilkins, et al., Rapid automated enzyme immunoassay of serum amyloid A, *Clin Chem.*, 40(7):1284-1290 (1994).

3×15 Test Kit for Detection of Plasma Protein C Activity Using a Clotting End-Point, Product #ACC-45, *American Diagnostica Inc.*, 1-2 (Feb. 1989).

Aillaud et al., *New Direct Assay of Free Protein S. Antigen Applied to Diagnosis of Protein S. Deficiency*, Thrombosis and Haemostatis, vol. 75, No. 2, 1996, pp. 283-285.

Astion, et al., Overtraining in neural networks that interpret clinical data, *Clin Chem.*, 39(9):1998-2004 (1993).

Astion, et al., The application of backpropagation neural networks to problems in pathology and laboratory medicine, *Arch. Pathol. Lab. Med.*, 116:995-1001 (Oct. 1992).

Baum and Haussler, What size net gives valid generalization?, *Neural Computation*, p. 81-89 (Jan. 1989).

Baumann et al., "Simulation of the extrinsic pathway of the plasmatic clotting system," *Haemostasis*, 21:329-337 (1991).

Baumann, et al., Computerized analysis of the *in vitro* activation of the plasmatic clotting system, *Haemostasis*, 19:309-321 (1989).

Bluestein and Archer, The sensitivity, specificity and predictive value of diagnostic information: a guide for clinicians, *Nurse Practitioner*, 16(7):39-45 (Jul. 1991).

Boone et al., Neural networks in radiologic diagnosis, *Investigative Radiology*, 25(9):1013-1023 (Sep. 1990).

Brandt, et al., Effect of lupus anticoagulants on the activated partial thromboplastin time. Results of the College of American Pathologists survey program, *Arch. Pathol. Lab Med.*, 115:109-114 (Feb. 1991).

Braun et al., Examination of prothrombin time (PT) and activated partial thromboplastin time (APTT) optical clot profiles using an automated thrombosis-hemostasis, *Coagulation Methods Instrumentation and Quality Control*, p. 1236, Abstract #1286 (1995).

Braun, et al., Properties of optical data from activated partial thromboplastin time and prothrombin time assays, *Thromb. Haemost.*, 78:1079-1087 (1997).

Carrol, et al., Ortho Educational Monograph,*The Clot Signature and New Aspects in Coagulation Testing*, Ortho Diagnostic Systems, Inc., p. 1-20 (1989).

Dassen, et al., Self-learning neural networks in electrocardiography, *J.Electrocardiol.*, 23 Suppl:200-202 (1990).

Downey et al., *Early Identification and Prognostic Implications in Disseminated Intravascular Coagulation through Transmittance Waveform Analysis*, Thromb. Haemost 1998; 80: 65-9.

Furlong, et al., Neural network analysis of serial cardiac enzyme data. A clinical application of artificial machine intelligence, *Am. J. Clin. Pathol.*, 96(1):134-141 (Jul. 1991).

Givens and Braun, Classification of factor deficiencies from coagulation assays using neural networks, *Int.J.Med.Inf.*, 46:129-143 (1997).

Givens et al., Interpretation of clot formation parameters from APTT and PT assays using neural networks, *Clin.Chem.*, 42(6):S192, Abstract #399 (1996).

Givens, et al., Predicting the presence of plasma heparin using neural networks to analyze coagulation screening assay optical profiles, *Comput.Biol.Med.*, 26(6):463-476 (1996).

Givens, T.B., Clot signatures, *Clin.Hemostasis Rev.*, p. 11-12 (Aug. 1997).

Heuck and Baumann, Kinetic analysis of the clotting system in the presence of heparin and depolymerized heparin, *Haemostasis*, 21:10-18 (1991).

Hoffman and Callahan, The Coag-A-Mate RA4 Fibrinogen Assay, *Interface* (Organon Teknika), p. 3-7 (1990).

Khanin and Semenov, A mathematical model of the kinetics of blood coagulation, *J.Theor.Biol.*, 136:127-134 (Jan. 1989).

*Koagulab 16-S Plus Graphics, Koagulab 32-S Coagulation System, Graphics Binder*, 2,3,5,6,8-12,14-17,19-21,23.

*Ortho Factor VIII: C Deficient Plasma*, Ortho Diagnostic Systems, Inc., pp. 1-2 (Sep. 1998).

Package insert for Ortho Brain Thromboplastic Reagent, *Ortho Diagnostic System, Inc.*, p. 1-7 (Oct. 1985).

Pattichis, et al., Efficient training of neural network models in classification of electromyographic data, *Med.Biol.Eng Comput.*, 33(3):499-503 (May 1995).

Pohl, et al., The quick machine—a mathematical model for the extrinsic activation of coagulation, *Haemostasis*, 24:325-337 (1994).

Sabbatini, R.M.E., Neural networks for classification and pattern recognition of biological samples, *Conf.of the Engineering in Medicine and Biology Society* (IEEE, New York, U.S.).

Schweiger, et al., Evaluation of laboratory data by conventional statistics and by three types of neural networks, *Clin.Chem.*, 39(9):1966-1971 (1993).

Supplementary European Search Report, European Application No. 00953788.7, May 19, 2003.

Supplementary European Search Report, European Application No. 00953788.7, Jun. 5, 2003.

Sweeney et al., Abnormal clot signatures in hereditary bleeding disorders, *Blood*, 74 Suppl 1(7):395, Abstract #1509 (Nov. 1989).

Sweeney et al., Abnormal clot signatures in hereditary bleeding disorders, *The American Society of Hematology Abstract Reproduction Form* (1989).

Sweeney et al., Kinetic clot parameters in gynecological tumors, *Blood*, 76 Suppl 1(10):439a, Abstract #1745-(Nov. 1990).

Swets, J. A., Measuring the accuracy of diagnostic systems, *Science*, 240:1285-1293 (Jun. 1988).

Talstad, I., Which coagulation factors interfere with the one-stage prothrombin time?, *Haemostasis*, 23:19-25 (1993).

Triplett, et al., Graphic monitoring of coagulation assays, *American Clinical Laboratory*, p. 1-5 (Apr. 1989).

Zuckerman et al. "Comparison of thrombelastography with common coagulation tests," *Thromb Haemostas*, 46: 752-6 (1981).

Zweig and Campbell, Receiver-operating characteristic (ROC) plots: a fundamental evaluation tool in clinical medicine, *Clin. Chem.*, 39(4):561-577 (1993).

Downey et al., "The Robustness and Reproducibility of APTT Waveform Analysis in Relation to Reagent and Batch Variation", *Thrombosis and Haemostasis* 805 (1999).

Toh et al., Characterisation of the Novel Calcium-Activation, Thrombin Suppression Assay (CaTs) in the DIC of.Sepsis, *Haemostasis*, 30:39 (2000).

\* cited by examiner

A.

B.

TRUNCATED CHART

```
                                SEQUENCE LISTING

<160> NUMBER OF SEQ ID NOS: 1

<210> SEQ ID NO 1
<211> LENGTH: 10
<212> TYPE: PRT
<213> ORGANISM: Homo sapiens
<220> FEATURE:
<221> NAME/KEY: misc_feature
<222> LOCATION: (6)..(6)
<223> OTHER INFORMATION: Amino acid residue unknown

<400> SEQUENCE: 1

Gln Thr Asp Met Ser Xaa Lys Ala Phe Val
1               5                   10
```

METHOD FOR DETECTING A LIPOPROTEIN-ACUTE PHASE PROTEIN COMPLEX AND PREDICTING AN INCREASED RISK OF SYSTEM FAILURE OR MORTALITY

CROSS-REFERENCES TO RELATED APPLICATIONS

This application is a National Phase application of PCT/US01/18611 filed on Jun. 8, 2001, published in English, which claims priority from U.S. patent application Ser. No. 09/591,642, filed Jun. 9, 2000, and is a continuation of U.S. patent application Ser. No. 09/591,642, filed Jun. 9, 2000, now abandoned, the subject matter of each being incorporated herein by reference.

BACKGROUND OF THE INVENTION

Blood clots are the end product of a complex chain reaction where proteins form an enzyme cascade acting as a biologic amplification system. This system enables relatively few molecules of initiator products to induce sequential activation of a series of inactive proteins, known as factors, culminating in the production of the fibrin clot. Mathematical models of the kinetics of the cascade's pathways have been previously proposed.

Thrombosis and hemostasis testing is the in vitro study of the ability of blood to form clots and to break clots in vivo. Coagulation (hemostasis) assays began as manual methods where clot formation was observed in a test tube either by tilting the tube or removing fibrin strands by a wire loop. The goal was to determine if a patient's blood sample would clot after certain materials were added. It was later determined that the amount of time from initiation of the reaction to the point of clot formation in vitro is related to congenital disorders, acquired disorders, and therapeutic monitoring. In order to remove the inherent variability associated with the subjective endpoint determinations of manual techniques, instrumentation has been developed to measure clot time, based on (1) electromechanical properties, (2) clot elasticity, (3) light scattering, (4) fibrin adhesion, and (5) impedance. For light scattering methods, data is gathered that represents the transmission of light through the specimen as a function of time (an optical time-dependent measurement profile).

Two assays, the PT and APTT, are widely used to screen for abnormalities in the coagulation system, although several other screening assays can be used, e.g. protein C, fibrinogen, protein S and/or thrombin time. If screening assays show an abnormal result, one or several additional tests are needed to isolate the exact source of the abnormality. The PT and APTT assays rely primarily upon measurement of time required for clot time, although some variations of the PT also use the amplitude of the change in optical signal in estimating fibrinogen concentration.

Blood coagulation is affected by administration of drugs, in addition to the vast array of internal factors and proteins that normally influence clot formation. For example, heparin is a widely-used therapeutic drug that is used to prevent thrombosis following surgery or under other conditions, or is used to combat existing thrombosis. The administration of heparin is typically monitored using the APTT assay, which gives a prolonged clot time in the presence of heparin. Clot times for PT assays are affected to a much smaller degree. Since a number of other plasma abnormalities may also cause prolonged APTT results, the ability to discriminate between these effectors from screening assay results may be clinically significant.

The present invention was conceived of and developed for predicting haemostatic dysfunction in a sample based on one or more time-dependent measurement profiles, such as optical time-dependent measurement profiles. In addition, the present invention is directed to predicting the presence of Disseminated Intravascular Coagulation in a patient based on a time-dependent profile, such as an optical transmission profile, from an assay run on the patient's blood or plasma sample.

SUMMARY OF THE INVENTION

The present invention is directed to a method for detecting a precipitate in a test sample in the absence of clot formation. The method includes providing a test sample and adding thereto a reagent, the reagent alone or in combination with additional reagents causing the formation of a precipitate. The reagent preferably comprises a metal divalent cation and optionally includes a clot inhibiting substance. The detection of the precipitate can be qualitative or quantitative, and the precipitate can be detected such as by a clotting assay, a latex agglutination or gold sol assay, an immunoassay such as an ELISA, or other suitable method that would allow for detection and/or quantitation of the precipitate. The formation of the precipitate can be detected as an endpoint value, or kinetically. This precipitate detection allows for predicting Haemostatic Dysfunction in patients. The present invention is useful for predicting Haemostatic Dysfunction that can lead to bleeding or thrombosis, or specifically to Disseminated Intravascular Coagulation (DIC).

More particularly, the present invention is directed to a method comprising adding a reagent to a test sample having at least a component of a blood sample from a patient, measuring the formation of a precipitate due to the reaction of the test sample and the reagent, over time so as to derive a time-dependent measurement profile, the reagent capable of forming a precipitate in the test sample without causing substantial fibrin polymerization.

The invention is also directed to a method for determining whether or not a patient has haemostatic dysfunction, comprising obtaining a blood sample from a patient, obtaining plasma from said blood sample, adding a reagent capable of inducing the formation of a precipitate in patients with haemostatic dysfunction without causing any substantial fibrin polymerization, taking one or more measurements of a parameter of the sample wherein changes in the sample parameter are capable of correlation to precipitate formation if present, and determining that a patient has haemostatic dysfunction if precipitate formation is detected.

The present invention is also directed to a method for determining in a patient sample the presence of a complex of proteins comprising at least one of a 300 kDa protein, serum amyloid A and C-reactive protein, comprising obtaining a test sample from a patient, adding an alcohol, a clot inhibitor, and a metal cation, wherein a precipitate is formed which comprises a complex of proteins including at least one of a 300 kDa protein, serum amyloid A and C-reactive protein.

The invention is also directed to a method comprising adding a coagulation reagent to an aliquot of a test sample from a patient, monitoring the formation of fibrin over time in said test sample by measuring a parameter of the test sample which changes over time due to addition of the coagulation reagent, determine a rate of change, if any, of said parameter in a period of time prior to formation of fibrin polymerization in said test sample, if the determined rate of change is beyond a predetermined threshold, then with a second aliquot of the patient test sample, add thereto a reagent that induces the formation of a precipitate in the absence of fibrin polymerization, measuring the formation of the precipitate over time, and determining the possibility or probability of haemostatic dysfunction based on the measurement of the precipitate.

The invention is also directed to a method for monitoring an inflammatory condition in a patient, comprising adding a reagent to a patient test sample, the reagent capable of causing precipitate formation in some patient test samples without causing fibrin polymerization, measuring a parameter of the test sample over time which is indicative of said precipitate formation, determining the slope of the changing parameter, repeating the above steps at a later date or time, wherein an increase or decrease in the slope at the later date or time is indicative of progression or regression, respectively, of the inflammatory condition.

The invention is further directed to a method for diagnosing and treating patients with haemostatic dysfunction, comprising adding a reagent to a test sample that causes precipitate formation without causing fibrin polymerization, taking measurements over time of a parameter of the test sample that changes due to the formation of the precipitate, determining the rate of change of said parameter, determining that a patient has haemostatic dysfunction if said rate of change is beyond a predetermined limit; intervening with treatment for said haemostatic dysfunction if said rate of change is beyond the predetermined limit.

The invention also is directed to a method comprising adding a reagent to a patient sample capable of causing formation of a precipitate in said sample, monitoring a changing parameter of said sample over time, said parameter indicative of said precipitate formation, determining the rate of change of said parameter or whether said parameter exceeds a predetermined limit at a predetermined time, repeating the above steps at least once, each time at a different plasma/reagent ratios, measuring the maximum, average and/or standard deviation for the measurements; and determining haemostatic dysfunction based on the maximum, average and/or standard deviation measurements.

The present invention is further directed to an immunoassay comprising providing a ligand capable of binding to C-reactive protein or the 300 kDa protein in lane 5 of FIG. 21, adding said ligand to a test sample from a patient and allowing binding of said ligand to C-reactive protein or said 300 kDa protein in said test sample, detecting the presence and or amount of C-reactive protein or said 300 kDa protein in said sample, and diagnosing haemostatic dysfunction in the patient due to the detection and/or amount of C-reactive protein or said 300 kDa protein detected.

The invention further relates to a method for testing the efficacy of a new drug on a human or animal subject with an inflammatory condition and/or haemostatic dysfunction, comprising adding a reagent to a patient test sample, said reagent capable of causing precipitate formation in some subject test samples without causing fibrin polymerization, measuring a parameter of said test sample over time which is indicative of said precipitate formation, determining the slope of said changing parameter and/or the value of said parameter at a predetermined time, administering a drug to said animal or human subject, repeating the above steps at a later date or time, wherein an increase or decrease in said slope or value at said later date or time is indicative of the efficacy of said drug.

DESCRIPTION OF THE PREFERRED EMBODIMENTS

In the present invention, not only can a particular abnormality (Haemostatic Disfunction) be detected, but in addition the progression of the disease can be monitored in a single patient. More particularly, system failure and/or mortality can be predicted. Haemostatic Dysfunction, as used herein, is a condition evidenced by the formation of a precipitate (prior to or in the absence of clot formation), depending upon the reagent used). As used herein, the term "and/or" includes any and all combinations of one or more of the associated listed items.

Disseminated intravascular coagulation (DIC—a type of Haemostatic Dysfunction) prognosis has been hampered by the lack of an early, useful and rapidly available diagnostic marker. The invention has been found to be not only useful as an early diagnostic and single monitoring marker of DIC, but in addition the quantifiable and standardizable changes also allow for prognostic applicability in clinical management.

Disseminated intravascular coagulation (DIC) is a secondary response to a pre-existing pathology whereby the haemostatic response becomes perturbed and disseminated as opposed to the focused events of normal haemostasis. Despite improvements both in the intensive care management of patients and in our basic knowledge of haemostatic mechanisms in DIC, survival in this patient group is still very discouraging. Fundamental to the management of this complication is the implementation of aggressive therapy directed at forestalling or eradicating the primary pathology as the source of the initiating stimulus. However, in practical terms, the problem remains one of early identification of DIC to facilitate immediate and appropriate intervention. Although the technological armory available to the clinical investigator has expanded enormously, the pace of acute DIC precludes most of the more specific tests and reliance is still placed on traditional screening tests such as the prothrombin (PT), activated partial thromboplastin time (APTT) and platelet count. These tests lack specificity on an individual basis and are only useful in DIC if they lead on to further determinations of fibrinogen and fibrin breakdown products/D-dimers. However, changes in these parameters may not occur all at the same time and as such, serial testing is often needed which inevitably leads to a delay in diagnosis and clinically useful intervention.

Figure 1:
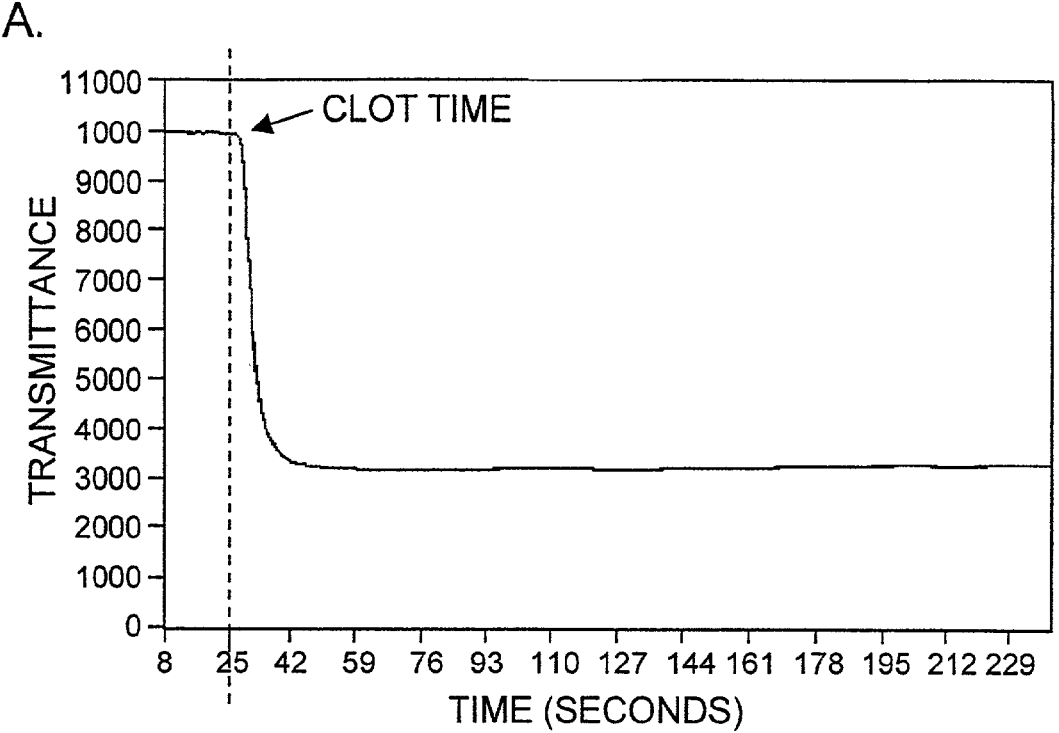
FIGS. 1A and 1B illustrate transmittance waveforms on the APTT assay with (A) showing a normal appearance, and (B) showing a biphasic appearance. Clot time is indicated by an arrow.
Figure 1:
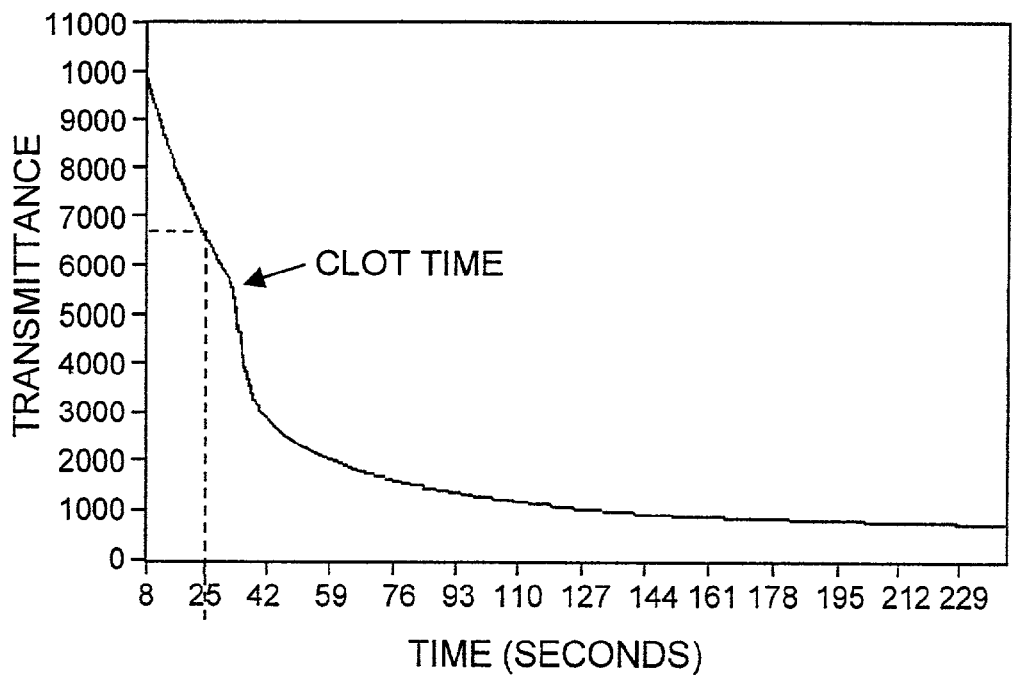

The normal sigmoidal appearance from an APTT transmittance waveform (TW) changes to a "bi-phasic" appearance in DIC patients. This represents a loss in the plateau of a normal APTT-TW, with development of an initial low gradient slope followed by a much steeper slope (FIGS. 1a and b). In addition, this bi-phasic pattern can be seen even when the APTT clotting time result is normal.

Freshly collected blood samples that required a PT or an APTT were analyzed prospectively over a two week working period. These were in 0.105 M tri-sodium citrate in the ratio of 1 part anticoagulant to 9 parts whole blood and the platelet-poor plasma was analyzed on the MDA (Multichannel Discrete Analyzer) 180, an automated analyzer for performing clinical laboratory coagulation assays using an optical detection system (Organon Teknika Corporation, Durham, N.C., USA). In addition, to deriving the clot times for both PT (normal 11.2–15 s) using MDA Simplastin LS™ and APTT (normal 23–35 S) using MDA Platelin LS™ with 0.025M calcium chloride (Organon Teknika Corporation, USA), an analysis of the TW for the APTT was performed on each occasion at a wavelength of 580 nm. To quantitate the visual profile, the amount of light transmittance at 25 seconds was recorded. A normal waveform has a light transmittance of 100% that is represented on the analyzer and in FIG. 1a without the decimal point as 10000. As such, a bi-phasic change will have a reduced light transmittance of less than 10000. As can be seen in FIG. 1B, decreasing levels of light transmittance prior to clot formation correlate directly with increasing steepness of the bi-phasic slope. The recording of the light transmittance at 25 seconds also allows for standardization between patients and within the same patient with time. If the minimum level of light transmittance for each sample were to be used instead, this would be affected by variations in the clot time of the APTT and would therefore not be ideal for comparisons.

To ensure that no cases of DIC were overlooked, the following criteria was followed. If (a) an abnormal bi-phasic TW was encountered, or (b) a specific DIC screen was requested, or (c) if there was a prolongation in either the PT or APTT in the absence of obvious anticoagulant therapy, a full DIC screen was performed. This would further include the thrombin time (TT) (normal 10.5–15.5 seconds), fibrinogen (Fgn) (normal 1.5–3.8 g/l) and estimation of D-dimer levels (normal <0.5 mg/l) on the Nyocard D-Dimer (Nycomed Pharma AS, Oslo, Norway). Platelet counts (Plt) (normal 150–400 $10^9$/l) performed on an EDTA sample at the same time were recorded. In addition, clinical details were fully elucidated on any patient with a bi-phasic TW or coagulation abnormalities consistent with DIC.

The diagnosis of DIC was strictly defined in the context of both laboratory and clinical findings of at least 2 abnormalities in the screening tests (increased PT, increased APTT, reduced Fgn, increased TT or reduced Plt) plus the finding of an elevated D-dimer level (>0.5 mg/l) in association with a primary condition recognized in the pathogenesis of DIC. Serial screening tests were also available on those patients to chart progression and confirmation of the diagnosis of DIC as was direct clinical assessment and management. For statistical analysis, values for the sensitivity, specificity, positive and negative prediction of the APTT-TW for the diagnosis of DIC were calculated employing a two-by-two table. 95% confidence intervals (CI) were calculated by the exact binomial method.

A total of 1,470 samples were analyzed. These were from 747 patients. 174 samples (11.9%) from 54 patients had the bi-phasic waveform change. 22 of these 54 patients had more than 3 sequential samples available for analysis. DIC was diagnosed in 41 patients with 30 of these requiring transfusion support with fresh frozen plasma, cryoprecipitate or platelets. The underlying clinical disorders as shown in Table 1.

TABLE 1

| Disorder | No |
| --- | --- |
| Infections | 17 |
| Trauma or recent major surgery | 16 |
| Malignancy | 2 |
| Hepatic Disease | 1 |
| Obstetric | 1 |
| Miscellaneous Additional Causes* | 4 |

*Includes hypoxia, acidosis, Lithium overdosage and graft rejection 40 of the 41 patients with DIC had the bi-phasic TW. The one false negative result (DIC without a bi-phasic TW) occurred in a patient with pre-eclampsia (PET) where the single sample available for analysis showed a prolonged PT of 21.0 s, APTT of 44.0 s and raised D-dimers of 1.5 mg/l. 5 other patients were identified in this study with PET and none had either DIC or a bi-phasic TW. Of the 14 patients with a bi-phasic TW which did not fulfil the criteria of DIC, all had some evidence of a coagulopathy with abnormalities in one or two of the screening tests. These abnormal results fell short of the criterion for DIC as defined above. 4 of these 14 patients had chronic liver disease with prolonged PT and mild thrombocytopaenia. A further 2 patients had atrial fibrillation with isolated elevation of D-dimer levels only. The remaining 8 patients were on the ICU with multiple organ dysfunction arising from trauma or suspected infection but without the classical laboratory changes of DIC. These patient profiles were described in the ICU as consistent with the "systemic inflammatory response syndrome" (SIRS). Based on these figures, the bi-phasic TW has a 97.6% sensitivity for the diagnosis of DIC with a specificity of 98%. Use of an optical transmittance waveform was found to be helpful in detecting the biphasic waveform.

TABLE 2

|  | Biphasic TW | Normal TW | Total |
|---|---|---|---|
| DIC Positive | 40 | 1 | 41 |
| DIC Negative | 14 | 692 | 706 |
| Total | 54 | 693 | 747 |

Sensitivity 97.6% (CI 85.6–99.99%), Specificity 98.0% (CI 96.6–98.9%), Positive predictive value 74.0% (CI 60.1–84.6%), Negative predictive value 99.9% (CI 99.1–99.99%)

Figure 2:
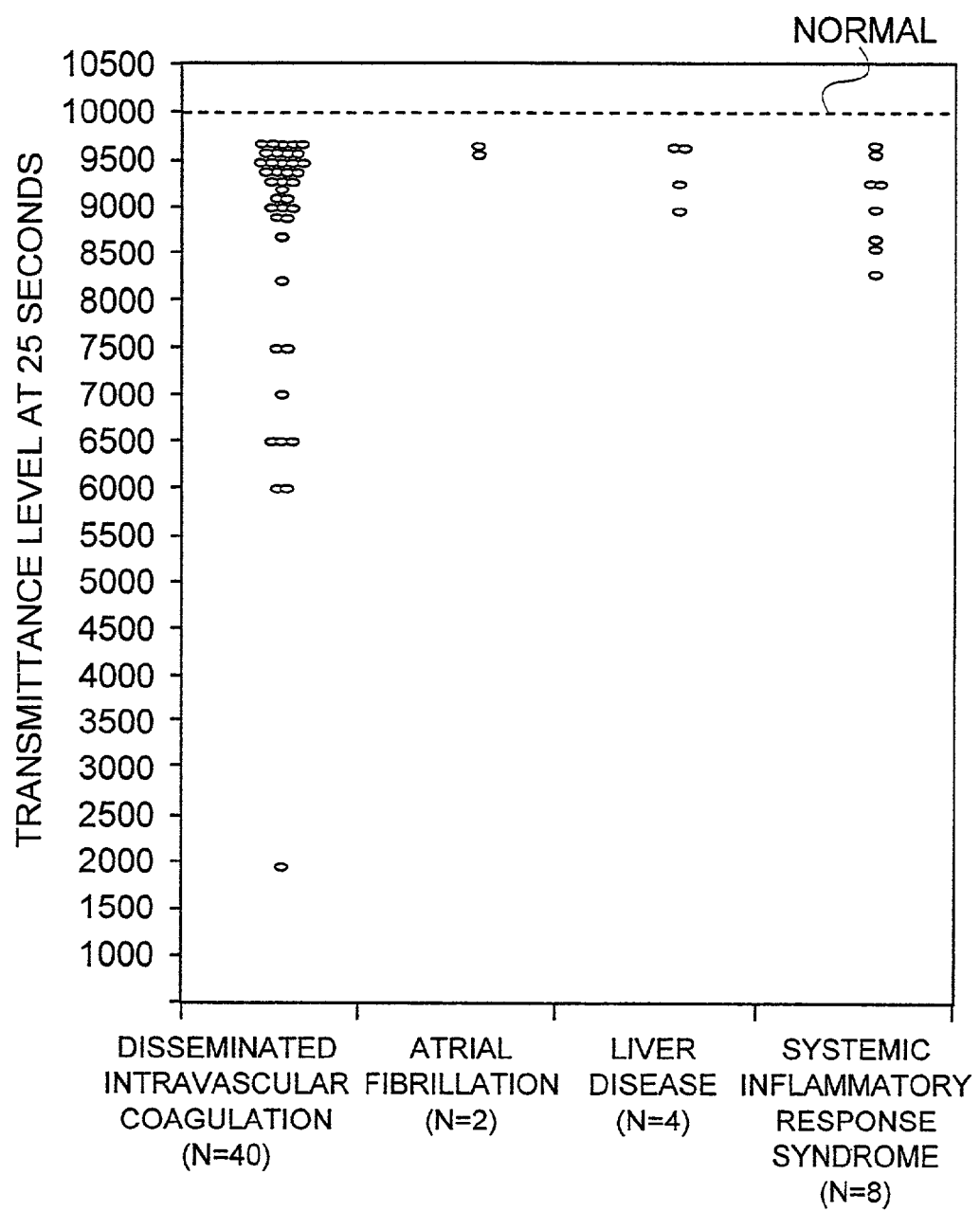
FIG. 2 illustrates transmittance levels at 25 seconds in relation to diagnosis in 54 patients with bi-phasic waveform abnormalities. The horizontal dotted line represents the normal transmittance level.

The positive predictive value of the test was 74%, which increased with increasing steepness of the bi-phasic slope and decreasing levels of light transmittance (Table 2 and FIG. 2). In the first two days of the study, there were 12 patients who had an abnormality in the clotting tests plus elevation of D-dimer levels. These were patients who were clinically recovering from DIC that occurred in the week preceding the study. This led to the impression that TW changes might correlate more closely with clinical events than the standard markers of DIC.

TABLE 3

| Day | Time | PT (11.2–15 s) | APTT (23–35 s) | TT (10.5–15.5 s) | Fgn (1.5–3.8 g/l) | D-Dimer (<0.5 mg/l) | Plt (150–400 × $10^9$/l) | TW |
|---|---|---|---|---|---|---|---|---|
| 1 | 0923 | 14.7 | 32.9 | 12.0 | 4.7 | 0.00 | 193 | B* |
| 1 | 2022 | 20.8* | 38.6* | 12.4 | 5.7 | 6.00* | 61* | B* |
| 2 | 0920 | 18.0* | 33.0 | 13.0 | 5.2 | 2.00* | 66* | N |
| 3 | 1011 | 16.3* | 24.8 | 13.2 | 4.7 | 0.00 | 64* | N |

PT = Prothrombin time, APTT = Activated Partial Thromboplastin Time, TT = Thrombin Time, Fgn = Fibrinogen, PTT = Platelet count, TW = Transmittance Waveform
*Indicates abnormal changes, B = bi-phasic, N = normal The availability of more than 3 sequential samples in 22 patients allowed for further assessment. Table 3 illustrates one such example with serial test results from a patient with *E. coli* septicaemia.

The appearance of a bi-phasic TW preceded changes in the standard tests for the diagnosis of DIC. It was only later in the day that the PT, APTT, Plt and D-dimer levels became abnormal and fulfilled the diagnostic criteria of DIC. Treatment with intravenous antibiotics led to clinical improvement by Day 2 with normalization of her TW in advance of the standard parameters of DIC. D-dimers and Plt were still respectively abnormal 24 and 48 hours later.

Figure 3:
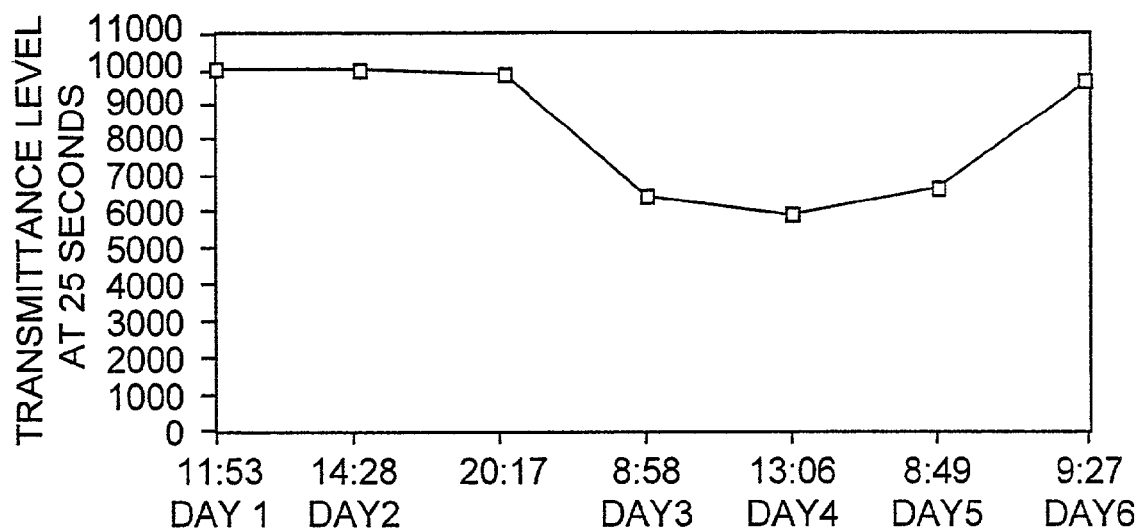
FIG. 3 illustrates serial transmittance levels (A)) and waveforms on day 1 (B), day 4 (C), and day 6 (D) on a patient who developed DIC following sepsis and recovered.
Figure 3:
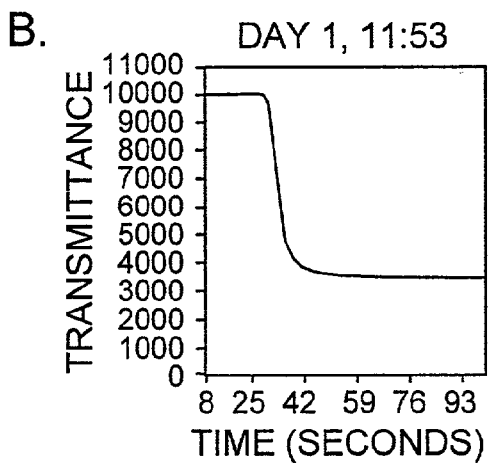
Figure 3:
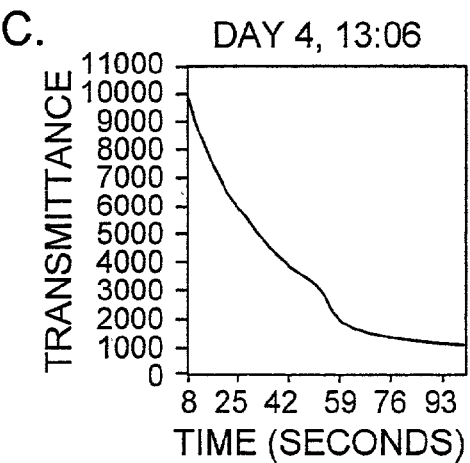
Figure 3:
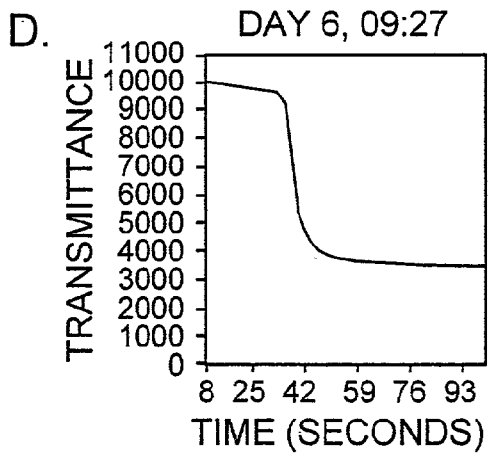
Figure 4:
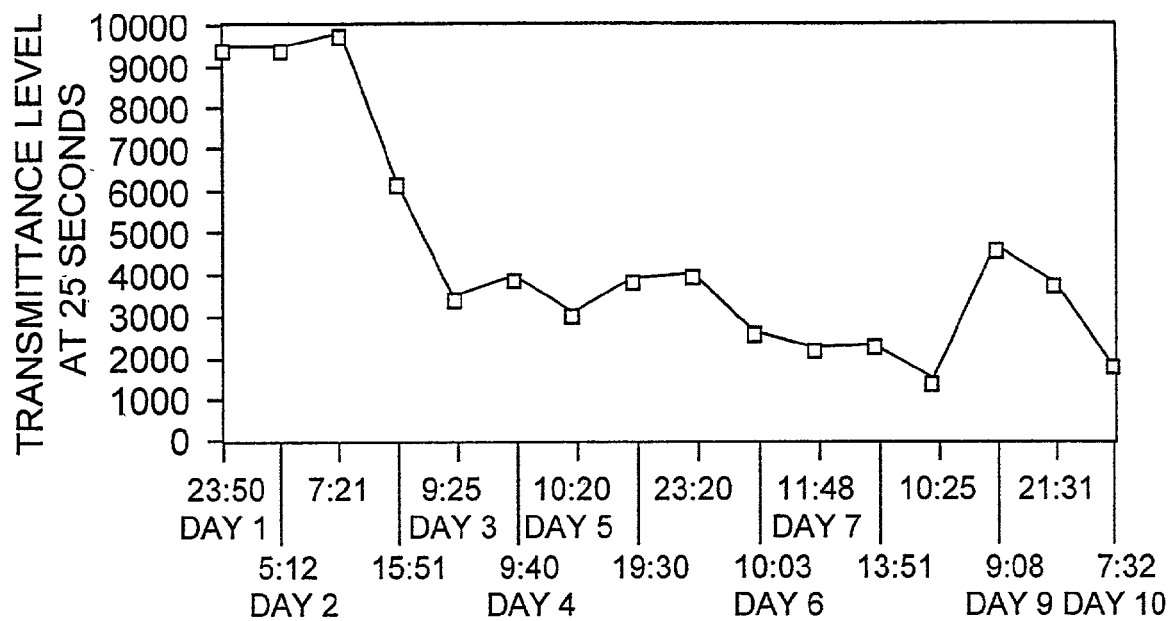
FIG. 4 illustrates serial transmittance levels (A) and waveforms on day 2 (B), day 5 (C), and day 10 (D) on a patient who developed DIC following trauma and died.
Figure 4:
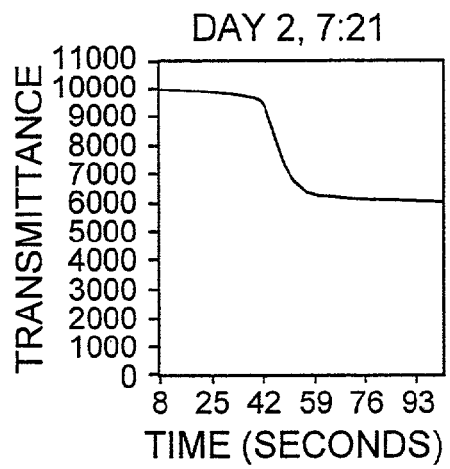
Figure 4:
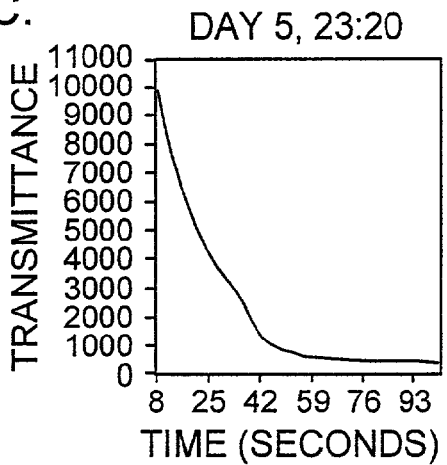
Figure 4:
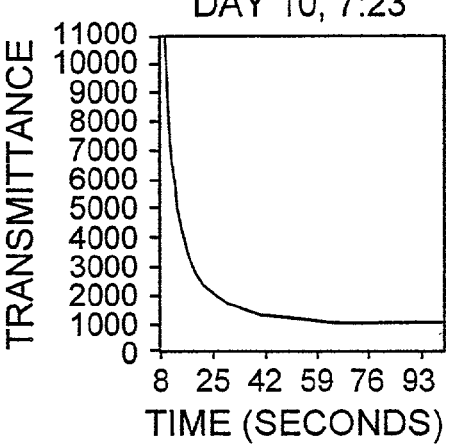

This correlation between clinical events and TW changes was seen in all the DIC patients where samples were available to chart the course of clinical events. As the TW changes were quantifiable and standardizable through recording of the transmittance level at 25 seconds, this analysis provided a handle in assessing prognostic applicability. FIG. 3 illustrates the results of a patient who initially presented with peritonitis following bowel perforation. This was further complicated by gram negative septicaemia postoperatively with initial worsening of DIC followed by a gradual recovery after appropriate therapy. As DIC progressed initially, there was increasing steepness in the bi-phasic slope of the TW and a fall in the light transmittance level. A reversal of this heralded clinical recovery. FIG. 4 illustrates the results of a patient who sustained severe internal and external injuries following a jet-ski accident. Although initially stabilized with blood product support, his condition deteriorated with continuing blood loss and development of fulminant DIC. The bi-phasic slope became increasingly steep with falls in transmittance level as the consequences of his injuries proved fatal.

As DIC can arise from a variety of primary disorders, the clinical and laboratory manifestations can be extremely variable not only from patient to patient but also in the same patient with time. There is therefore, a need for systems that are not only robust in their diagnosis but simple and rapid to perform. Although it has been shown that the bi-phasic TW appeared to be sensitive for Haemostatic Dysfunction (e.g. DIC) and was not seen in other selected patient groups with coagulation aberrations or influenced by either (i) pre-analytical variables, (ii) different silica-based APTT reagents, (iii) the use of thrombin as the initiator of the coagulation reaction or (iv) treatment in the form of heparin or plasma expanders, the robustness of this assay for DIC could only be addressed through a prospective study. This study has shown that the bi-phasic TW provides diagnostic accuracy in DIC with an overall sensitivity of 97.6% and specificity of 98%. In contrast, none of the standard parameters on an individual basis (i.e., PT, APTT, TT, Fgn, Plt, D-dimers) or even in combination, has ever reached the degree of sensitivity or specificity. The ready availability of TW data from the MDA-180 would also fulfil the criteria of simplicity and rapidity unlike the measurements of thrombin-antithrombin complexes or other markers that are dependent on ELISA technology. In addition, the advantages of TW analysis are that: (a) the bi-phasic TW change appears to be the single most useful correlate within an isolated sample for DIC and as such, reliance need no longer be placed on serial estimations of a battery of tests, and (b) the appearance or resolution of the bi-phasic TW can precede changes in the standard, traditional parameters monitored in DIC with strong, clear correlation to clinical events and outcome.

Although the bi-phasic TW was also seen in patients who did not have DIC per se as defined by the above criteria, the clinical conditions were associated with Haemostatic Dysfunction—namely activated coagulation prior to initiation of clot formation resulting in a biphasic waveform (for example in chronic liver disease or in the very ill patients on the Intensive Care Unit who had multiple organ dysfunction). It appears that bi-phasic TW is sensitive to non-overt or compensated DIC and that a transmittance level of less than 90% (FIG. 2) or sequential falls in that level (FIG. 4), reflects decompensation towards a more overt manifestation and potentially fulminant form of DIC. This line of explanation is supported by the observation of only a mild bi-phasic TW (transmittance level of about 95%) in 2 patients with atrial fibrillation; a condition that is associated with mild coagulation activation and elevated D-dimer levels. As no follow-up samples were available on these 2 patients whose clinical details were otherwise unremarkable, their bi-phasic TW could well have been transient. Nonetheless, these cases illustrate that the lower the level of light transmittance, the more likely the bi-phasic TW becomes predictive of Haemostatic Dysfunction, particularly DIC.

The observation of a normal TW in a patient with PET and DIC needs further exploration as the study did not selectively aim to examine any particular patient groups and only had a total of 6 patients with PET; the remaining 5 of which did not have DIC. One explanation which would be supported by other findings in this study is that the patient could have been recovering from PET and DIC at the time of the sample. There may already have been normalization in the bi-phasic TW in advance of the other parameters which were still abnormal and indicative of DIC. Another explanation is that the disturbed haemostatic process in PET is more localized and different from the DIC that arises from other conditions. Such patients respond dramatically to delivery of the fetus which suggests anatomical localization of the pathological process to the placenta despite standard laboratory clotting tests implying systemic evidence of the condition.

EXAMPLE

Though analysis of the transmittance at a time of 25 seconds is helpful in predicting DIC, a second embodiment of the invention has been found that greatly improves sensitivity and specificity. It has been found that looking at transmittance at a particular time can result in detecting an artifact or other decrease in transmittance at that point, even though the waveform is not a bi-phasic waveform. For example, a temporary dip in transmittance at 25 seconds would cause such a patient sample to be flagged as bi-phasic, even if the waveform was normal or at least not bi-phasic. Also, if a patient sample had a particularly short clotting time, then if clot formation begins e.g. prior to 25 seconds (or whatever time is preselected), then the waveform could be flagged as biphasic, even though the real reason for decreased transmittance at 25 seconds is because clot formation has already begun/occurred.

Figure 9:
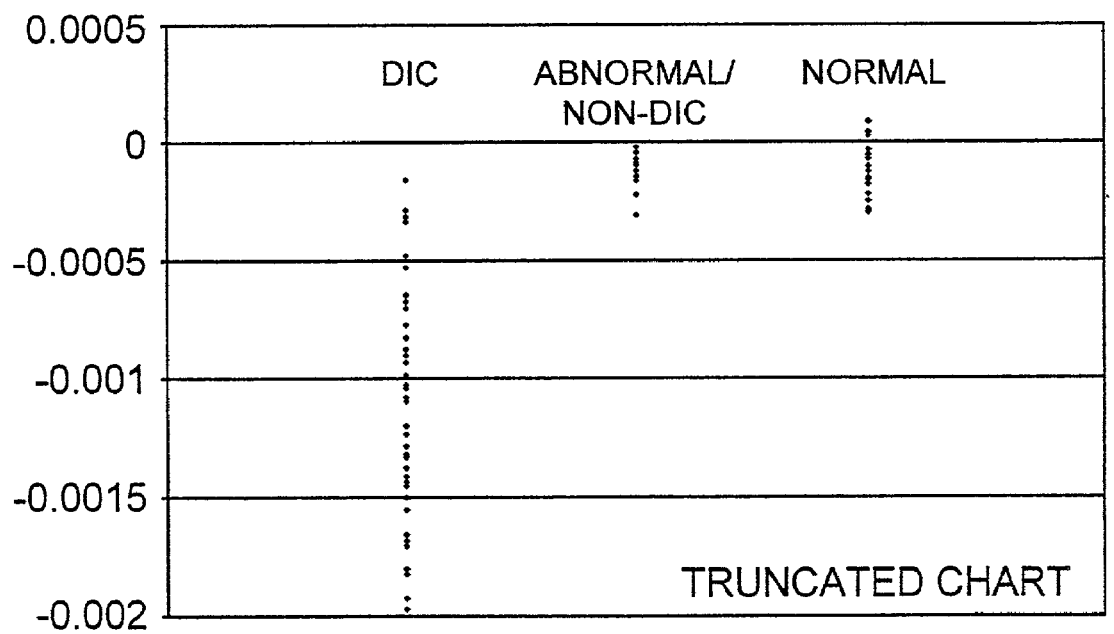
FIG. 9 shows partial subpopulations of the data shown in FIG. 8.
Figure 11:
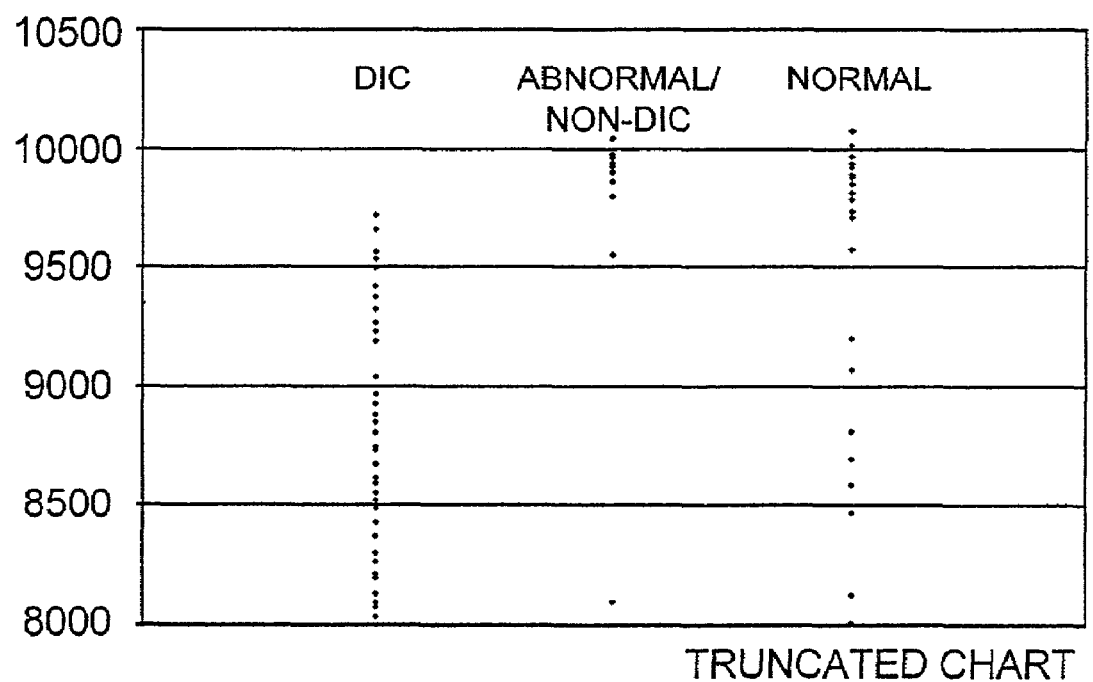
FIG. 11 shows partial subpopulations of the data shown in FIG. 10.

For this reason, it has been found that rather than analysis of transmittance at a particular time, it is desirable to calculate the slope of the waveform prior to initiation of clot formation. This calculation can involve determination of clot time followed by determination of waveform slope prior to clot time. In an additional embodiment, the slope (not transmittance) is determined prior to clot time or prior to a preselected time period, whichever is less. As can be seen in FIG. 11, when transmittance is used for determining e.g. DIC, there is poor specificity and sensitivity: However, as can be seen in FIG. 9, when slope prior to initiation of clot formation is used, specificity and sensitivity are greatly improved, and are better than standard tests used in the diagnosis of Haemostatic Dysfunction, such as DIC.

Figure 5:
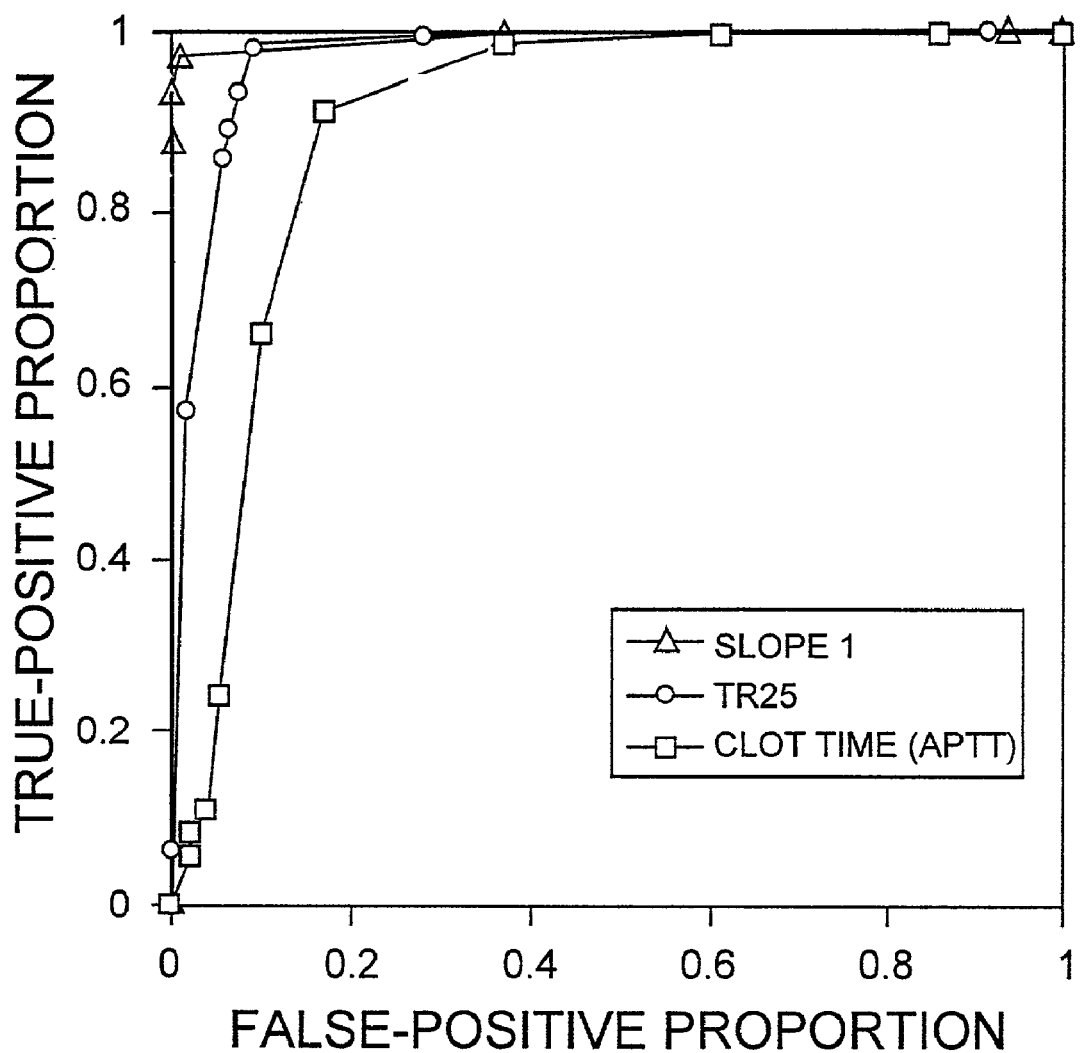
FIG. 5 illustrates ROC plots for the prediction of DIC transmittance at 25 seconds (TR25), APTT clot time, and slope_1 (the slope up to the initiation of clot formation).

Additional testing was performed on three sets of patients. The first set consisted of 91 APTT assays run on samples from 51 different confirmed DIC patients. The second set of data consisted of 110 APTT assays run on samples from 81 different confirmed normal patients. The third set of data included 37 APTT assays run on 22 abnormal, non-DIC samples. FIG. 5 illustrates ROC plots for the prediction of DIC for three different parameters derived from the APTT assay using the combined data sets described: (1) transmittance at 25 seconds (TR25), (2) APTT clot time, and (3) slope 1 (the slope up to initiation of clot formation). Slope 1 exhibited the best predictive power, followed by TR25. It has also been shown that transmittance at 18 seconds has predictive value, particularly when the APTT clot time is less than 25 seconds. The "cutoffs" associated with the highest efficiency for the three parameters are listed in Table 4:

TABLE 4

| Parameter | Cutoff |
| --- | --- |
| TR25 | <9700 |
| Clot Time | >35 |
| Slope 1 | <−0.0003 |

Figure 6:
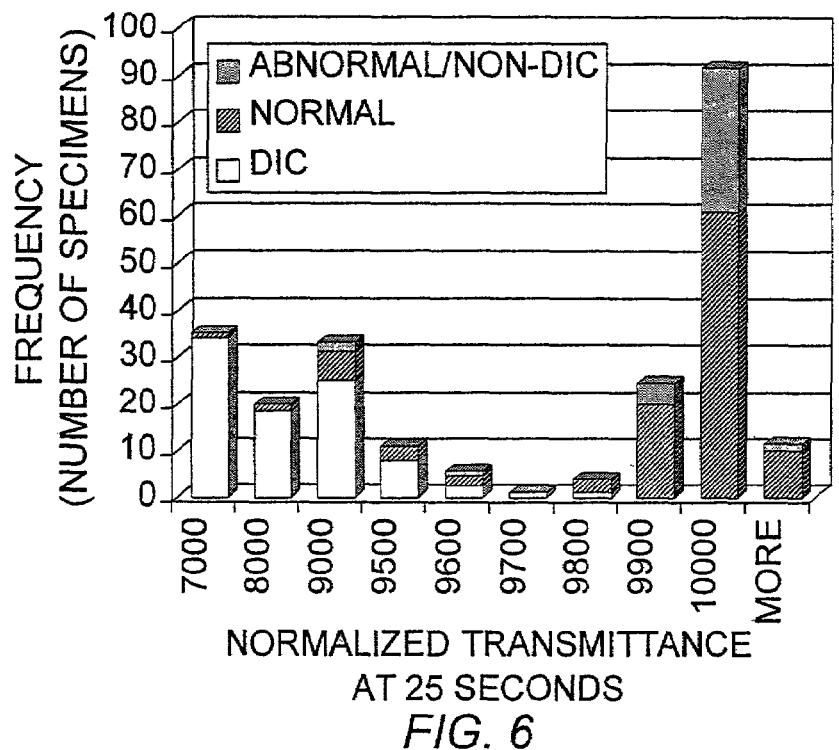
FIG. 6 shows a histogram for DIC, normal and abnormal/non-DIC populations for TR25.
Figure 7:
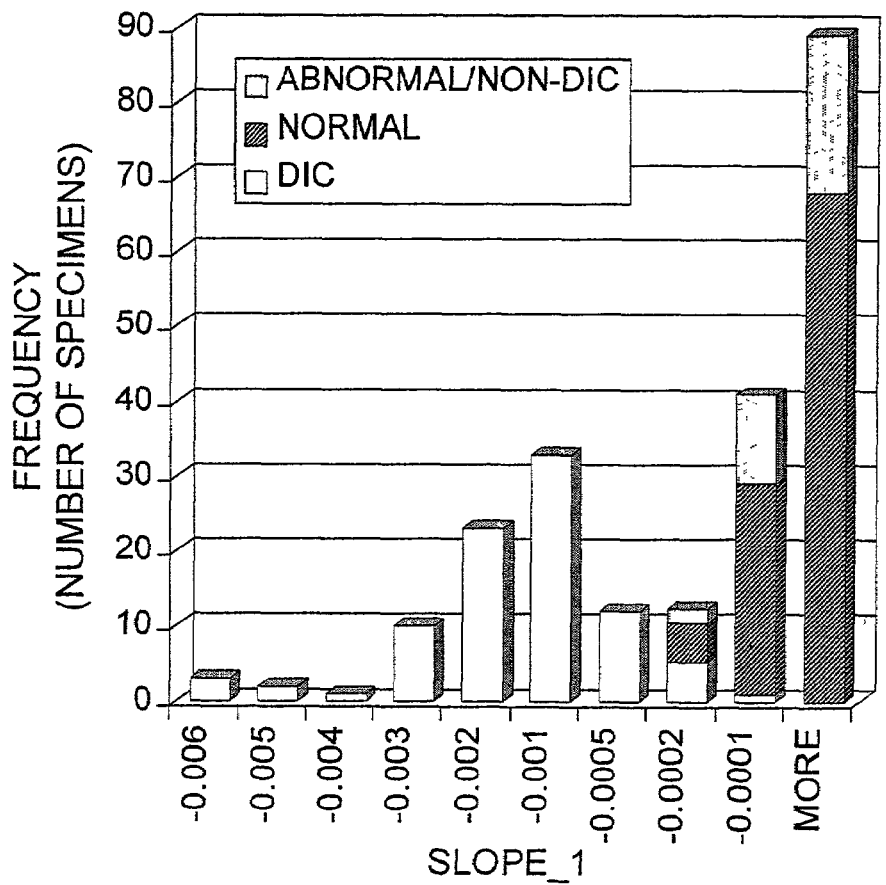
FIG. 7 shows a histogram for DIC, normal and abnormal/non-DIC populations for Slope_1.

It should be noted that these cutoffs have shifted with the addition of the third set, and would likely shift again, depending on the sample populations. FIGS. 6 and 7 show the histograms for the DIC, normal and abnormal/non-DIC populations for TR25 and slope 1 respectively. Tables 5 and 6 show the data for the histograms in FIGS. 6 and 7 respectively:

TABLE 5

| Bins | DIC | Normal | Abnormal/Non-DIC |
| --- | --- | --- | --- |
| −0.006 | 3 | 0 | 0 |
| −0.005 | 2 | 0 | 0 |
| −0.004 | 1 | 0 | 0 |
| −0.003 | 10 | 0 | 0 |
| −0.002 | 24 | 0 | 0 |
| −0.001 | 33 | 0 | 0 |
| −0.0005 | 12 | 0 | 0 |
| −0.0002 | 5 | 5 | 2 |
| −0.0001 | 1 | 37 | 13 |
| More | 0 | 68 | 22 |

TABLE 6

| Bin | DIC | Normal | Abnormal/Non-DIC |
| --- | --- | --- | --- |
| 7000 | 34 | 1 | 0 |
| 8000 | 18 | 2 | 0 |
| 9000 | 26 | 6 | 1 |
| 9500 | 8 | 3 | 0 |
| 9600 | 3 | 2 | 1 |
| 9700 | 1 | 0 | 0 |
| 9800 | 1 | 3 | 0 |
| 9900 | 0 | 21 | 4 |
| 10000 | 0 | 62 | 30 |
| More | 0 | 10 | 1 |

Figure 8:
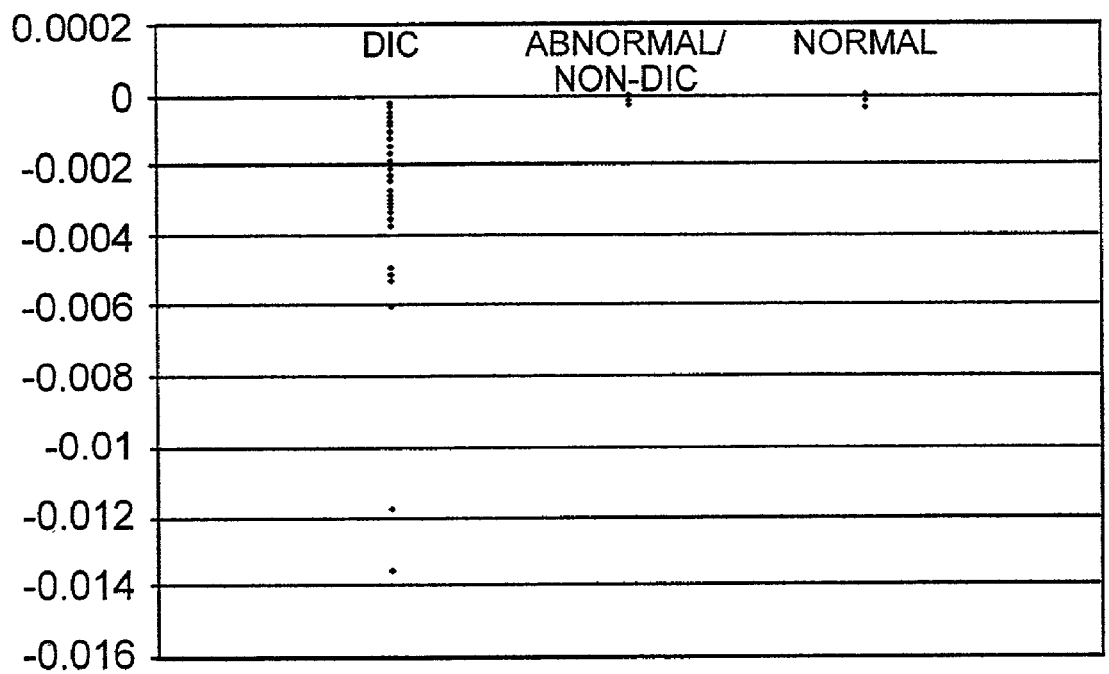
FIG. 8 shows group distributions for slope_11.
Figure 10:
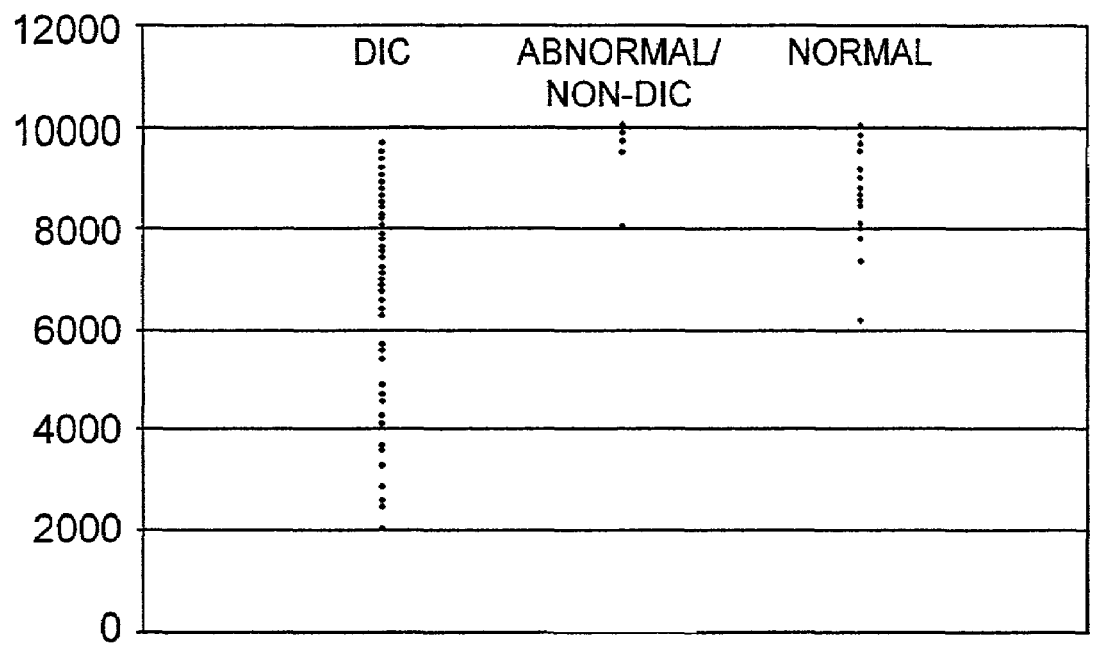
FIG. 10 shows group distributions for TR25.

FIGS. 8 and 10 show the group distributions for Slope 1 and TR25 respectively; and FIGS. 9 and 11 show the group distributions for Slope 1 and TR25 respectively. FIGS. 9 and 11 show partial subpopulations of the data shown in FIGS. 8 and 10.

When the prediction of Haemostatic Dysfunction is performed on an automated or semi-automated analyzer, the detected bi-phasic waveform can be flagged. In this way, the operator of the machine, or an individual interpreting the test results (e.g. a doctor or other medical practitioner) can be alerted to the existence of the biphasic waveform and the possibility/probability of Haemostatic Dysfunction such as DIC. The flag can be displayed on a monitor or printed out. A slope of less than about −0.0003 or less than about −0.0005 is the preferred cutoff for indicating a bi-phasic waveform. An increasing steepness in slope prior to clot formation correlates to disease progression.

The above examples show that waveform analysis on the APTT assay can identify characteristic bi-phasic patterns in patients with haemostatic dysfunction. In the majority of cases, this dysfunction could be labelled as DIC. This diagnostic waveform profile was seen in all APTT reagents tested, which were either silica or ellagaic acid-based. It has also been surprisingly found that a bi-phasic waveform can also be seen on PT assays with particular reagents, and that the bi-phasic waveform is likewise indicative of haemostatic dysfunction, primarily DIC.

Using samples that give bi-phasic APTT waveforms, the PT waveform profile was derived using PT reagents (thromboplastin), namely Recombiplast™ (Ortho), Thromborel™ (Dade-Behring), and Innovin™ (Dade-Behring). Both Recombiplast™ and Thromborel™ were particularly good at showing bi-phasic responses. Innovin™ was intermediate in its sensitivity. Using the transmittance level at 10 seconds into the PT reaction as the quantitative index, Recombiplast™ and Thromborel™ objectively showed lower levels of light transmittance than Innovin™. Thromborel™ can show a slight increase in initial light transmittance before the subsequent fall. This may be, in part, related to the relative opaqueness of Thromborel™.

Figure 12:
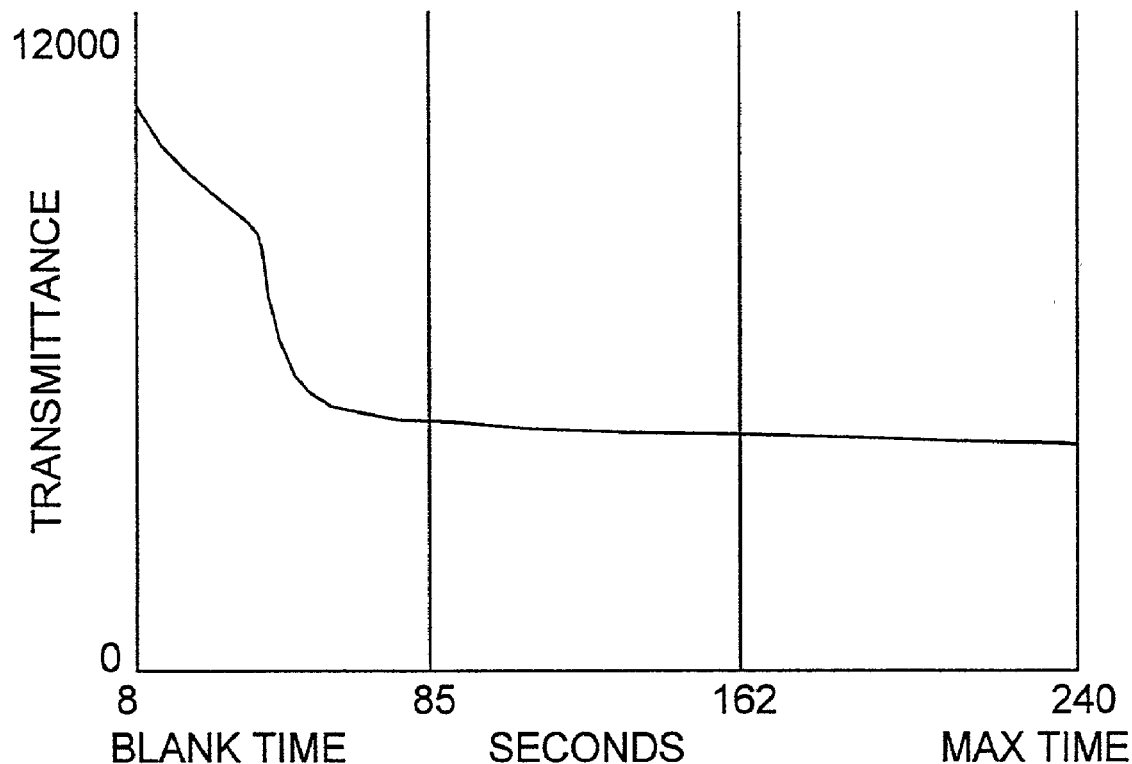
FIG. 12 is an optical transmission profile for an APTT assay using Platelin™.
Figure 13:
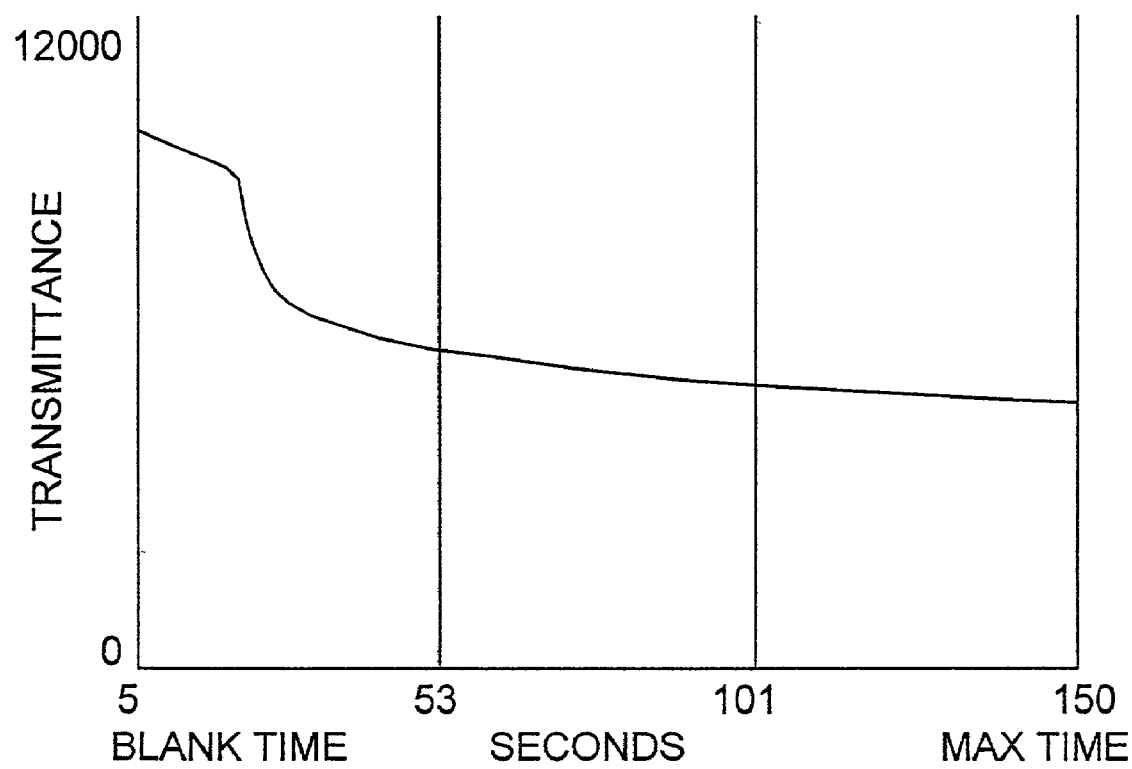
FIG. 13 is an optical transmission profile for the PT assay using Recombiplast™.
Figure 14:
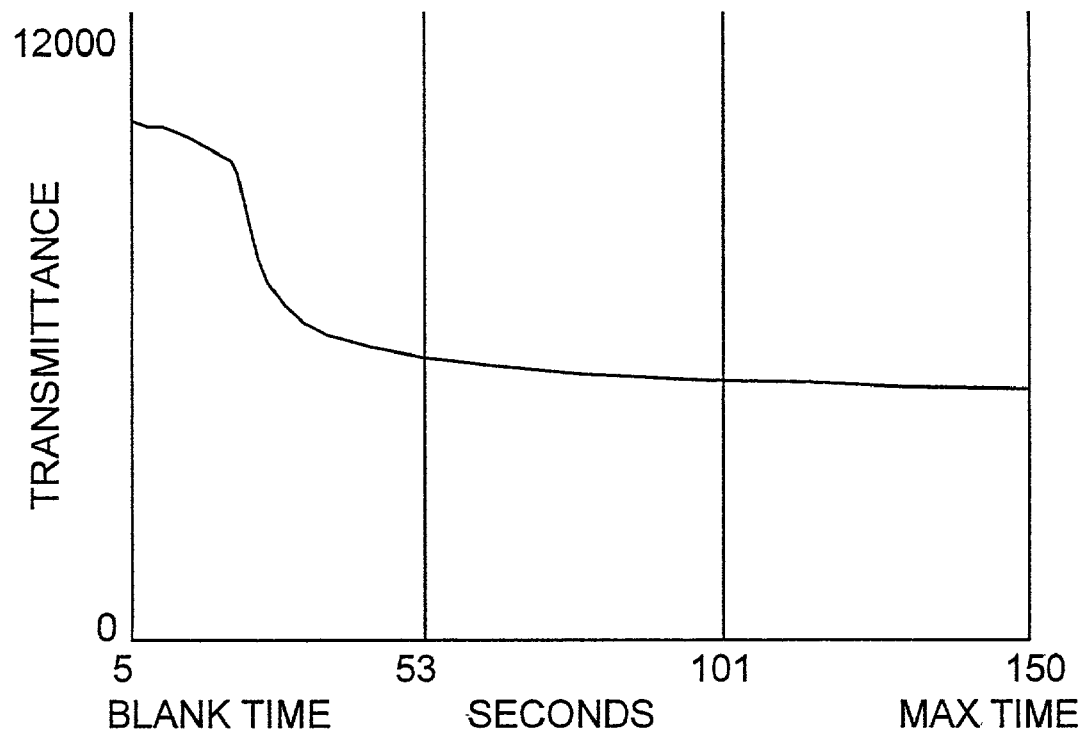
FIG. 14 is an optical transmission profile for the PT assay using Thromborel S™.

Further studies were performed comparing APTT profiles using Platelin™ and PT waveform profiles using Recombiplast™. Consecutive samples over a four week period from the intensive care unit were assessed. Visually, and on objective scores (comparing TL18 for APTT and TL10 for PT), the APTT profile was more sensitive to changes of haemostatic dysfunction and clinical progression than the PT profile. This relative sensitivity can be seen in the APTT profile of FIG. 12 (Platelin) compared to the PT profiles of FIG. 13 (Recombiplast) and FIG. 14 (Thromborel S). Invariably, at smaller changes in light transmittance, the APTT waveform detected abnormalities more easily than the PT waveform. Nonetheless, in severe degrees of haemostatic dysfunction, both bi-phasic profiles were concordant.

In a further embodiment of the invention, the time dependent measurement, such as an optical transmittance profile, can be performed substantially or entirely in the absence of clot formation. In this embodiment, a reagent is added which causes the formation of a precipitate, but in an environment where no fibrin is polymerized. The reagent can be any suitable reagent that will cause the formation of a precipitate in a sample from a patient with haemostatic dysfunction, such as DIC. As an example, divalent cations, preferably of the transition elements, and more preferably calcium, magnesium, manganese, iron or barium ions, can be added to a test sample. These ions cause activation of an atypical waveform that can serve as an indicator of haemostatic dysfunction. It is also possible to run this assay in the absence of a clotting reagent (APTT, PT, or otherwise). As part of the reagent that comprises the activator of the atypical waveform, or separately in another reagent, can also be provided a clot inhibitor. The clot inhibitor can be any suitable clot inhibitor such as hirudin, PPACK, heparin, antithrombin, I2581, etc. The formation of the atypical waveform can be monitored and/or recorded-on an automated analyzer capable of detecting such a waveform, such as one that monitors changes in turbidity (e.g. by monitoring changes in optical transmittance).

Figure 15:
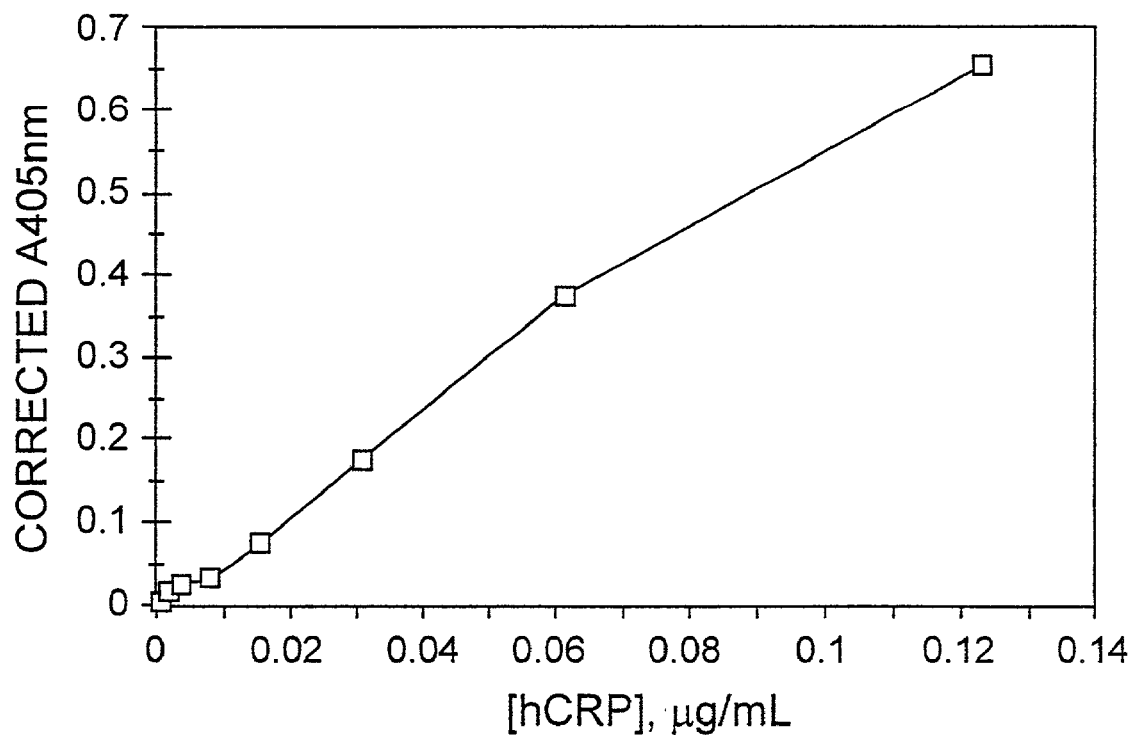
FIG. 15 is a standard curve for ELISA of CRP.
Figure 44:
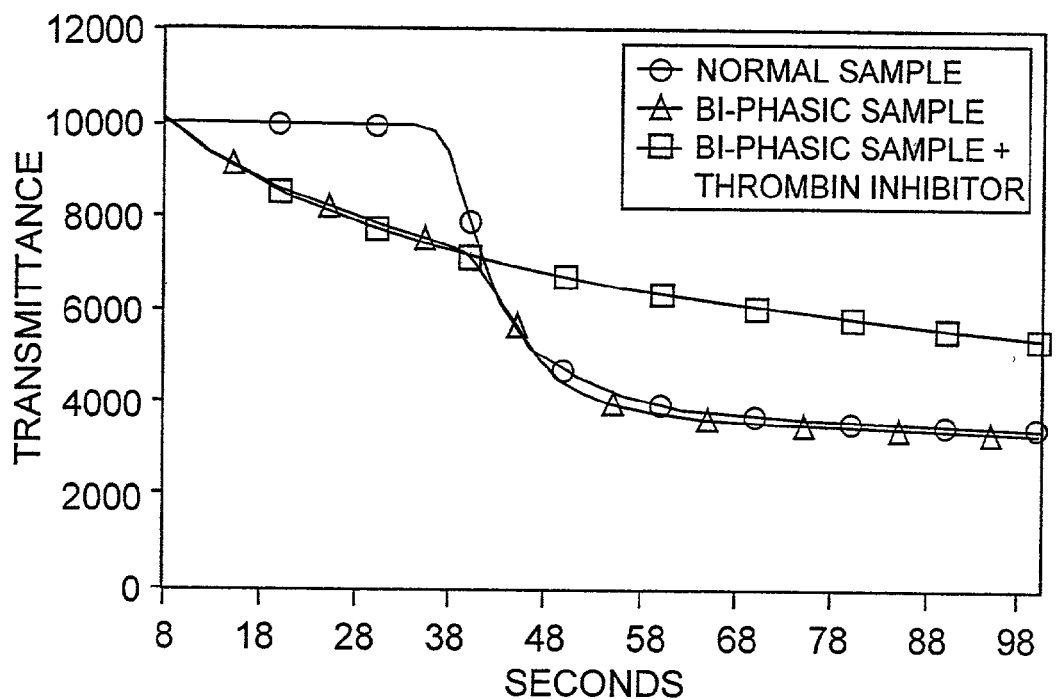
FIG. 44 is a graph depicting MDA waveforms for normal, bi-phasic, and bi-phasic/thrombin inhibitor samples.
Figure 45:
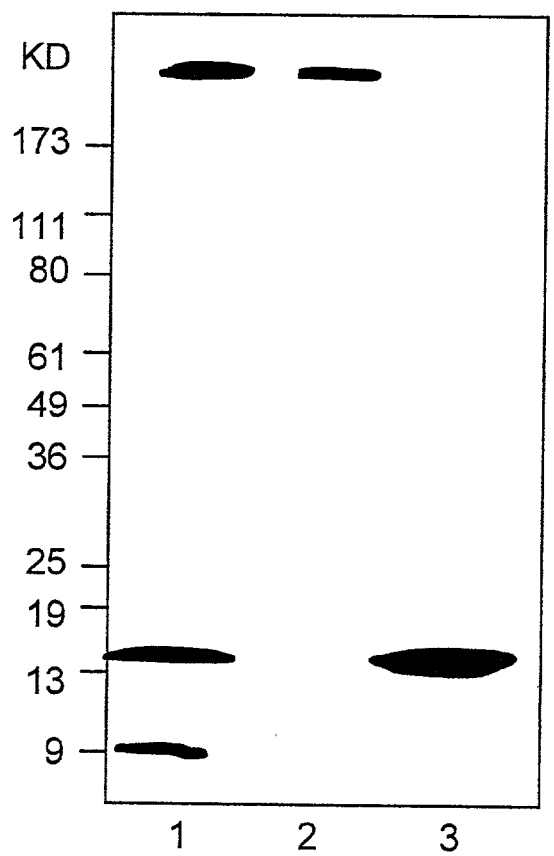
FIG. 45 is non-reducing SDS-PAGE gel of isolated precipitate before and after anion exchange chromatography. Lanes 1–3 were loaded with the starting material, peak 1, and peak 3, respectively.
Figure 46:
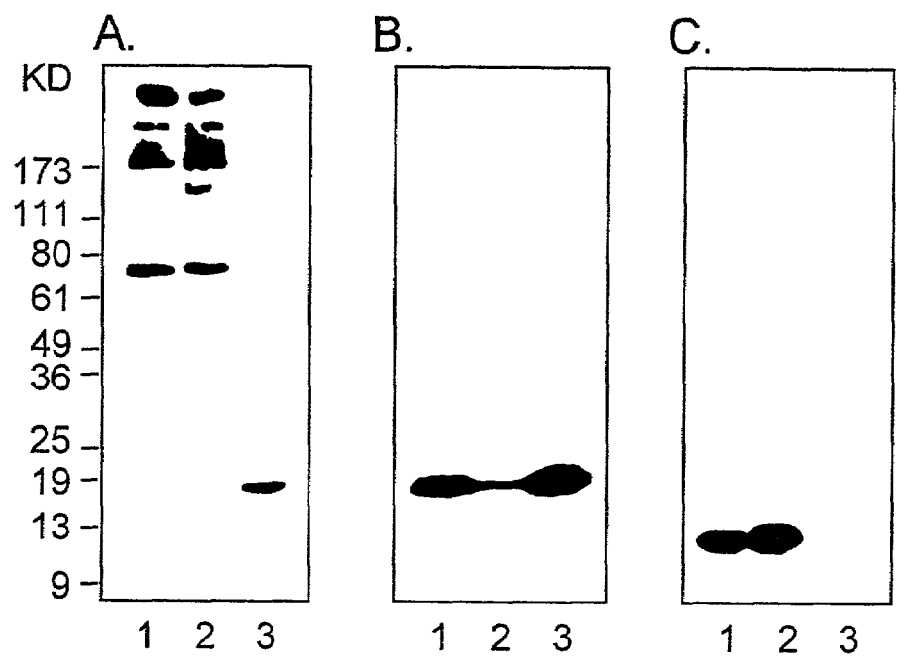
FIG. 46 are non-reducing SDS-PAGE gels that were immunoblotted and probed with either anti-APO(B) (A), anti-CRP (B), or anti-SAA (C) antibody. The blots represent the analysis of isolated precipitate before and after anion exchange chromatography. Lanes 1–3 were loaded with the starting material, peak 1, and peak 3, respectively.
Figure 47:
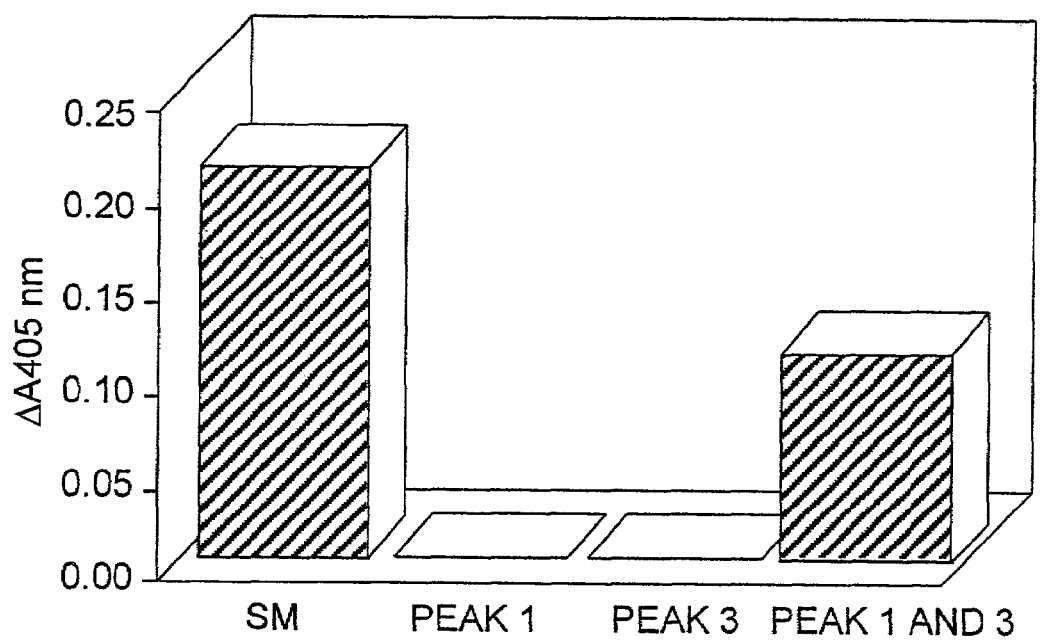
FIG. 47 is a graph depicting the turbidity changes associated with the a mixture of peaks 1 and 3 isolated from anion exchange chromatography.
Figure 48:
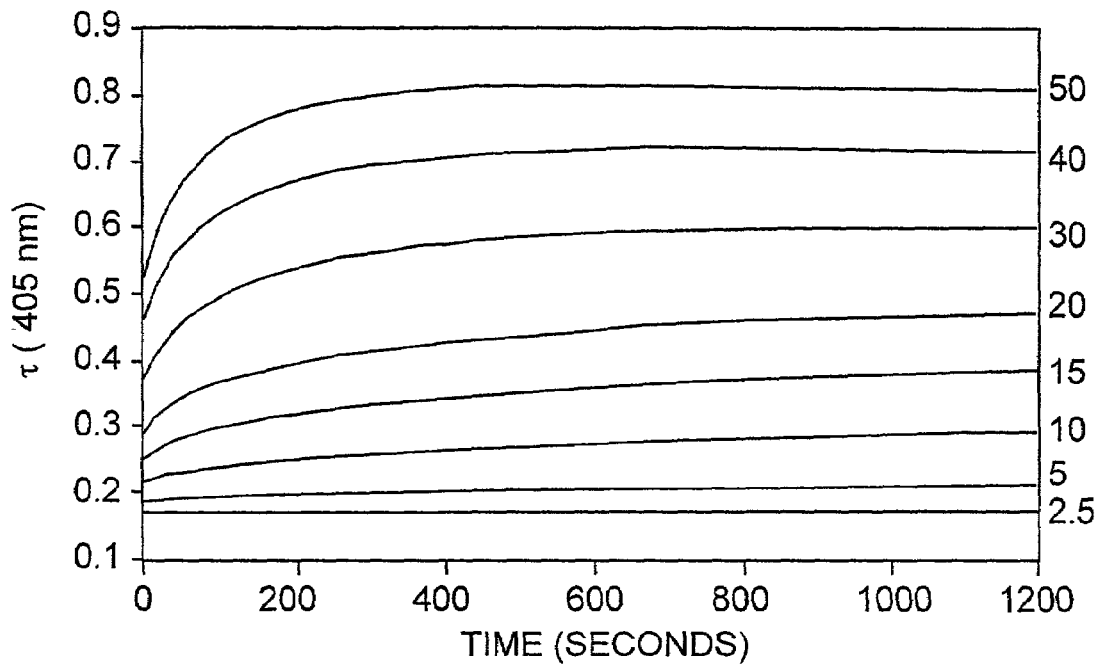
FIG. 48 is a graph showing the time course of turbidity changes after adding $Ca^{++}$ to mixtures of normal plasma and the plasma of a patient with a biphasic waveform. The values at the right are volumes of patient plasma in a total of 50 μL.
Figure 49:
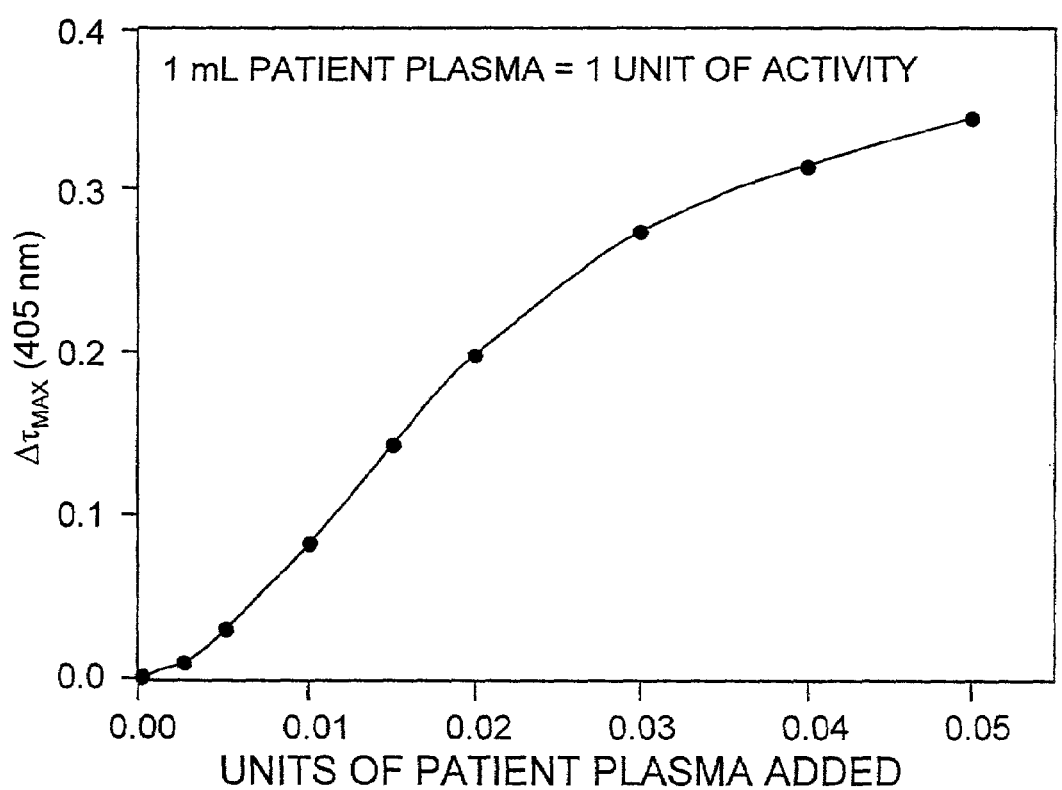
FIG. 49 is a graph depicting a standard curve assay of the change in turbidity associated with varying amounts of patient plasma added. 1 mL of patient plasma=1 unit of activity.
Figure 50:
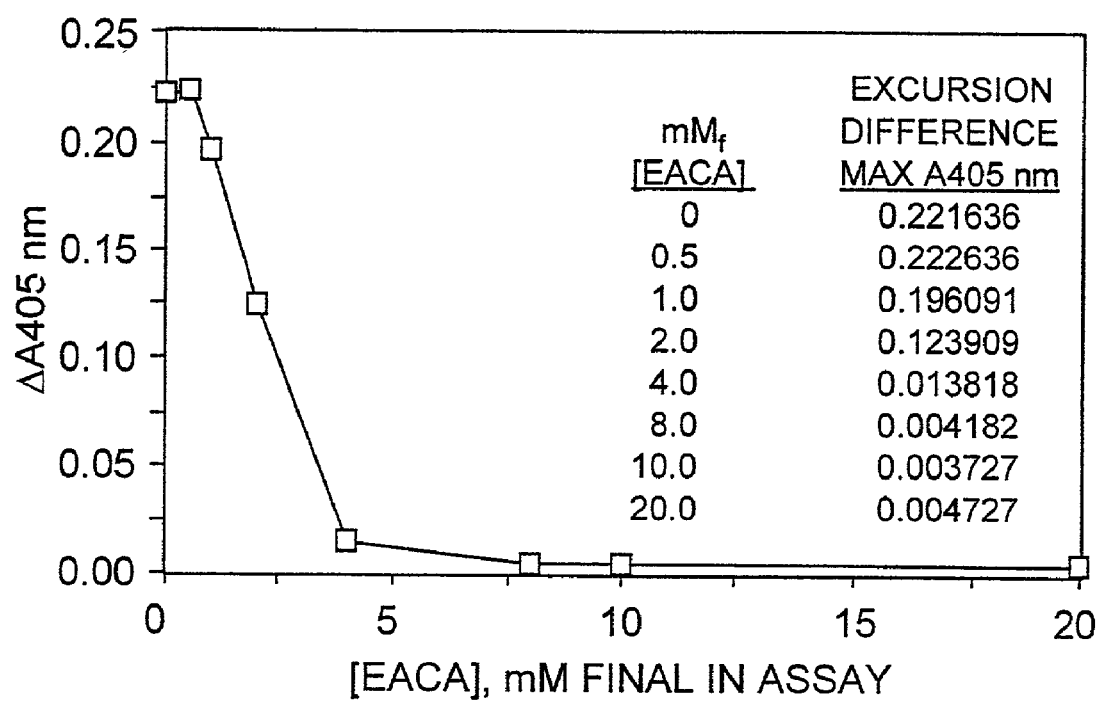
FIG. 50 is a graph depicting the effect of EACA on $Ca^{++}$-dependent turbidity changes associated with VLDL and CRP.

FIG. 44 is an illustration of two waveforms: waveform (triangles) is a test run on a sample using an APTT clotting reagent and resulting in an atypical (biphasic) waveform, whereas waveform (squares) is a test run on a sample where a clot inhibitor is used (along with a reagent, such as a metal divalent cation, which causes the formation of a precipitate in the sample). Waveform (squares) is exemplary of a waveform that can result in patients with haemostatic dysfunction where no clotting reagent is used and/or a clot inhibitor is added prior to deriving the time-dependent measurement profile. Generally speaking, the greater the slope of the waveform (the larger the drop in transmittance in the same period of time) due to the precipitate formation, the greater severity of the patient's haemostatic dysfunction. FIG. 15 is a standard curve for ELISA of CRP (CRP isolated from a patient used as the standard).

The precipitate formed in the present invention was isolated and characterized by means of chromatography and purification. Gel Filtration was performed as follows: A column (Hiprep Sephacryl S-300 High resolution—e.g. resolution of 10 to 1500 kDa) was used. The volume was 320 ml (d=26 mm, l=600 mm), and the flow rate was 1.35 ml/min.

Figure 16:
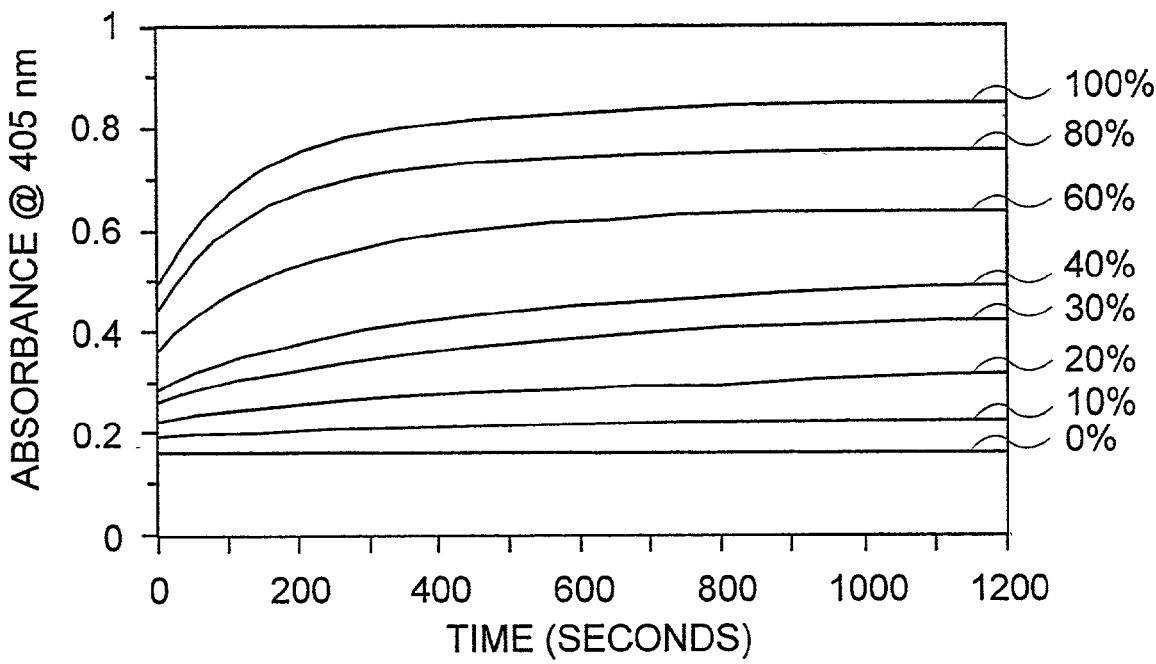
FIG. 16 is a graph showing the time course of turbidity in a sample upon adding $Ca^{2+}$ and PPACK compared to samples of normal and patient plasmas mixed in the various proportions indicated to the right. HBS/1 mM citrate was the diluent.
Figure 17:
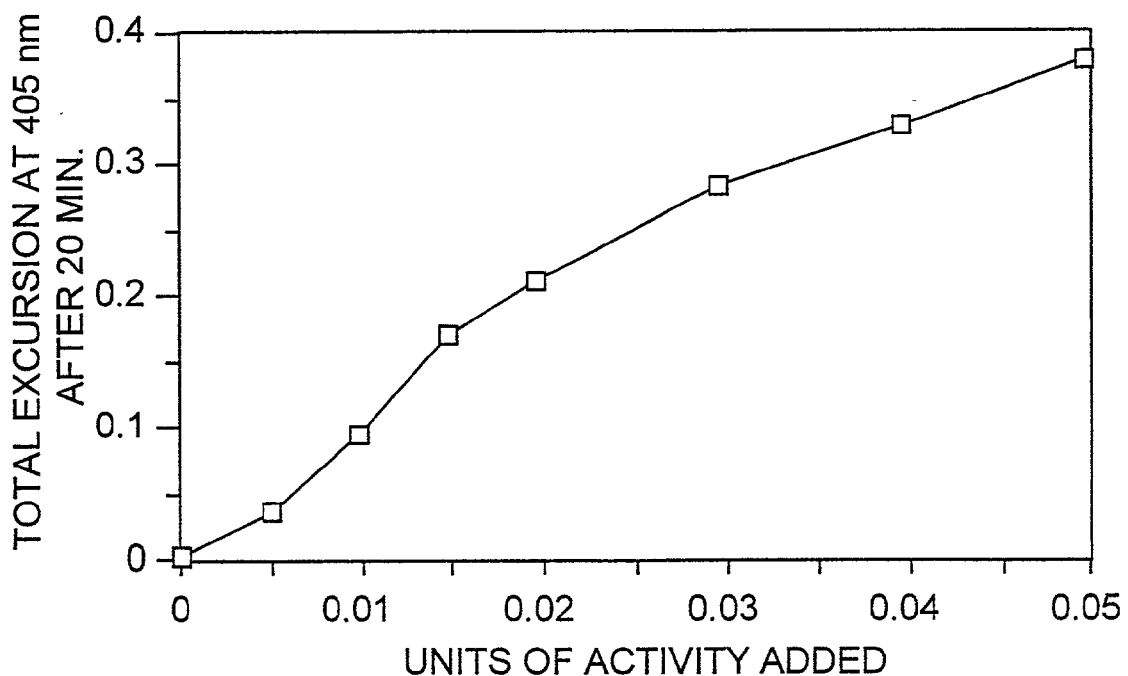
FIG. 17 is a graph showing the relationship between maximum turbidity change and amount of patient plasma in a sample.

FIG. 16 is a graph showing the time course of turbidity in a sample upon adding a precipitate inducing agent (in this case divalent calcium) and a thrombin inhibitor (in this case PPACK) to mixtures of patient and normal plasmas. FIG. 17 is a graph showing the relationship between maximum turbidity change and amount of patient plasma in one sample. 0.05 units implies 100% patient plasma.

Figure 18:
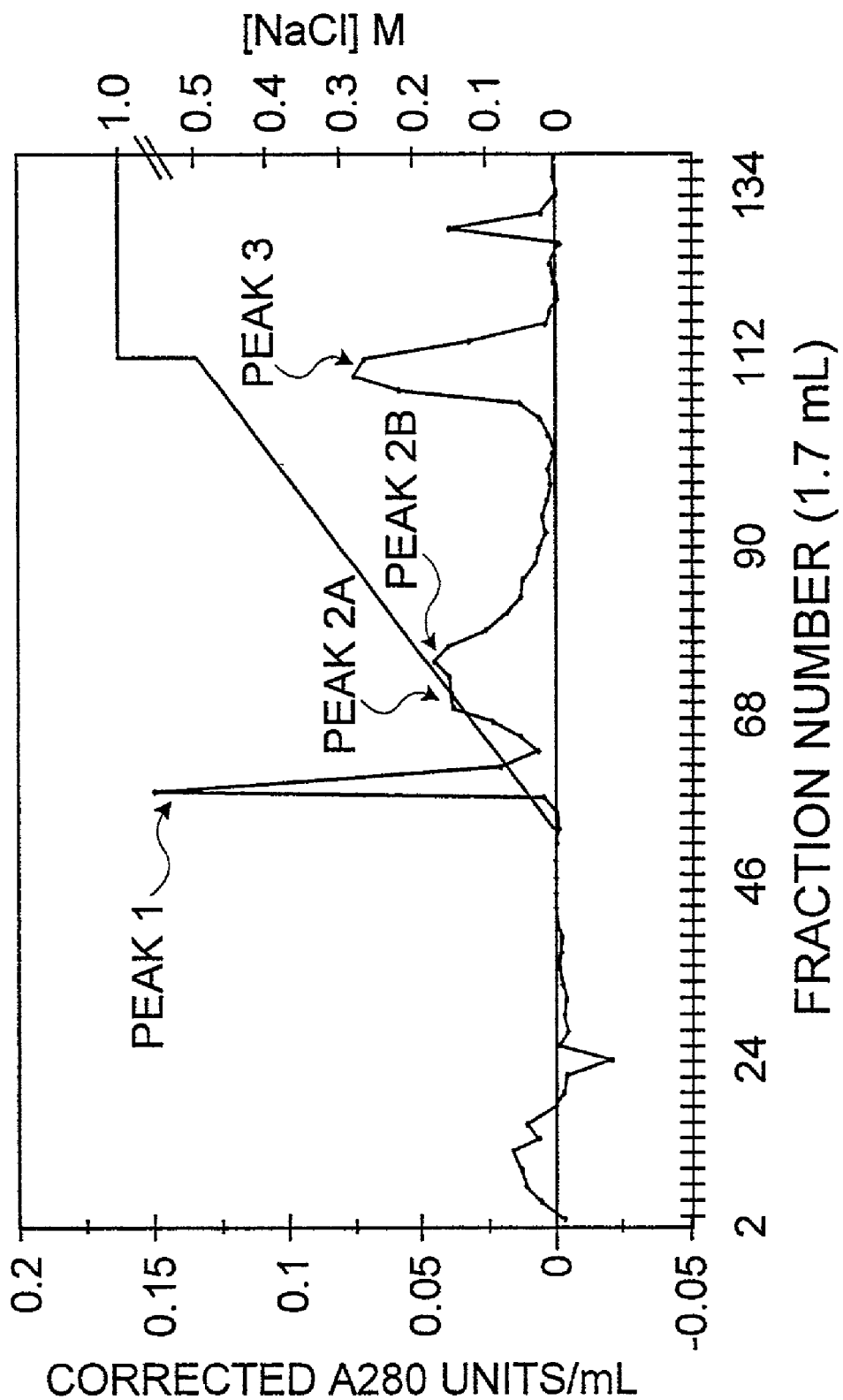
FIG. 18 shows the results of anion exchange chromatography of material recovery after fractionation of patient plasma. Peaks of interest are indicated.

The steps used in the purification of components involved in the turbidity change in a patient's plasma were as follows: PPACK (10 µM) was added to patient plasma. Calcium chloride was added to S0 mM, followed by 8 minutes of incubation, followed by the addition of ethanol to 5%. The sample was then centrifuged 10,500×g for 15 minutes at 4 degrees Celsius. The pellet was then dissolved in HBS/1 mM citrate/10 µM PPACK, followed by 35–70% $(NH_4)_2SO_4$ fractionation. Finally, an ion exchange chromatography was performed using a 5 ml bed, 0.02–0.5M NaCl gradient and 50 ml/side, to collect 2 ml fractions. FIG. 18 shows the results of anion exchange chromatography (Q-sepharose) of material recovered after the 35–70% ammonium sulfate fractionation of patient plasma.

Figure 19:
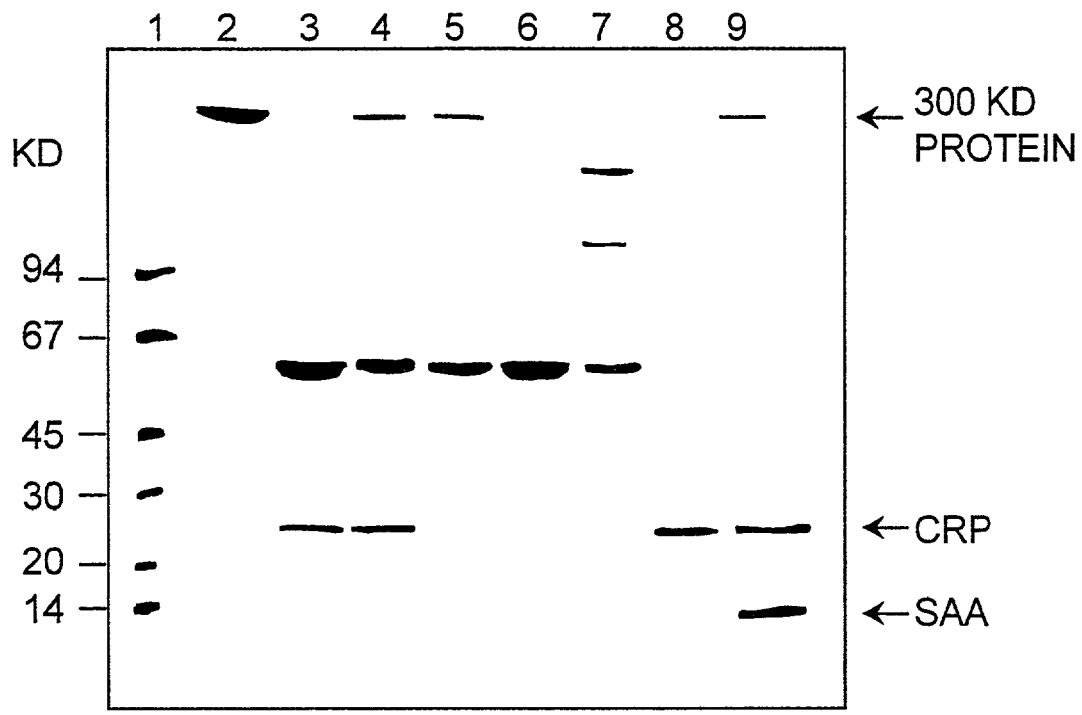
FIG. 19 shows non-reduced (A) and reduced (B) SDS-PAGE of various fractions of patient plasma.
Figure 19:
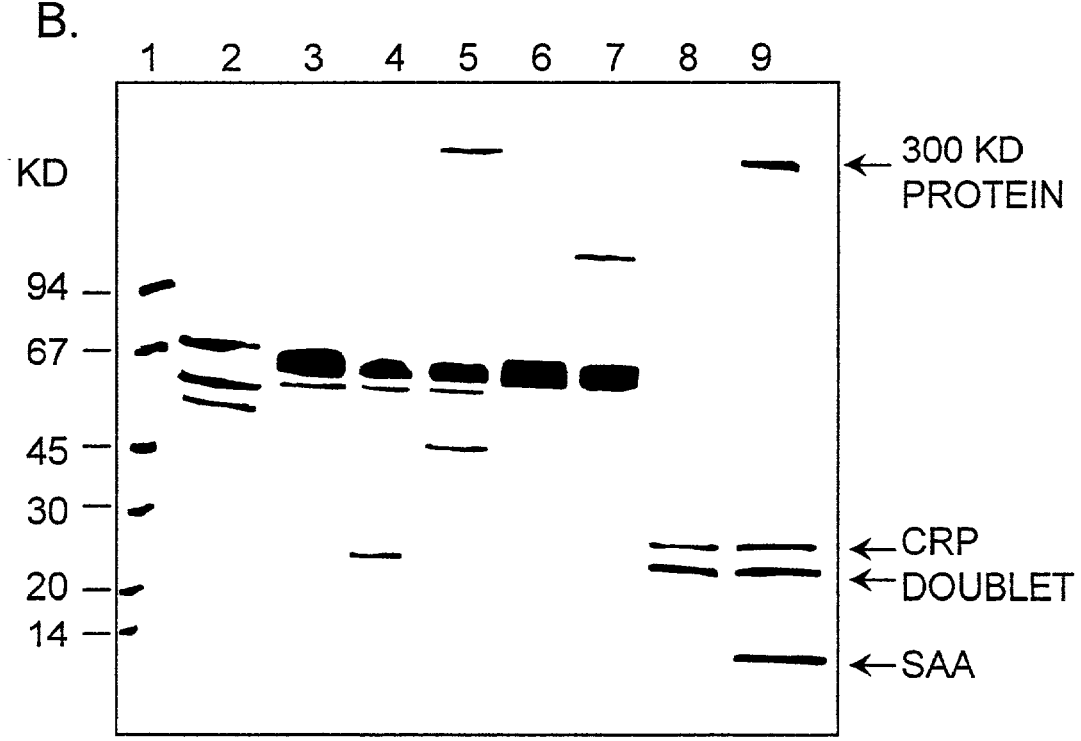

FIGS. 19A and 19B show the non-reduced and reduced, respectively, SDS-PAGE of various fractions obtained upon fractionation of patient plasma. The loading orientation (left to right): 5–15% gradient/Neville Gel. (approximately 10 µg protein loaded per well). In lane 1 are molecular weight standards (94, 67, 45, 30, 20 and 14 kDa from top to bottom. In lane 2 is 35% $(NH_4)_2SO_4$ pellet, whereas in lane 3 is 70% $(NH_4)_2SO_4$ supernate. Lane 4 is Q-sepharose starting material. Also shown in FIGS. 19A and 19B are (from FIG. 18) peaks 1, 2a, 2b and 3 in, respectively, lanes 5, 6, 7 and 8. Lane 9 is pellet 1, whereas in lane 10 are again, molecular weight standards. Results of $NH_2$-terminal sequencing showed peak 3, the 22 kDa protein in lanes 8 and 9 to be C-reactive protein (CRP), and the 10 kDa protein in lane 9 to be human serum amyloid A (SAA). Peak 1 in lane 5 is a>300 kDa protein which, as can be seen in FIG. 21, is part of the complex of proteins (along with CRP) in the precipitate formed due to the addition of a metal divalent cation to a plasma sample.

Figure 20:
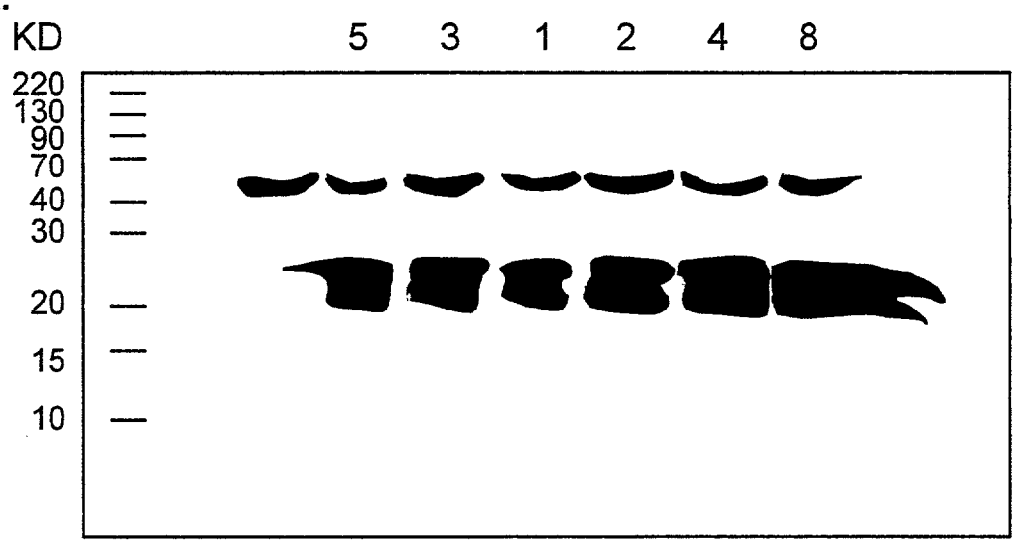
FIG. 20 shows immunoblots of CRP in normal (A and B) and DIC plasma (C). In (A) and (B) lanes are labelled with the patient number; (C) is labeled with the ng amount of CRP loaded.
Figure 20:
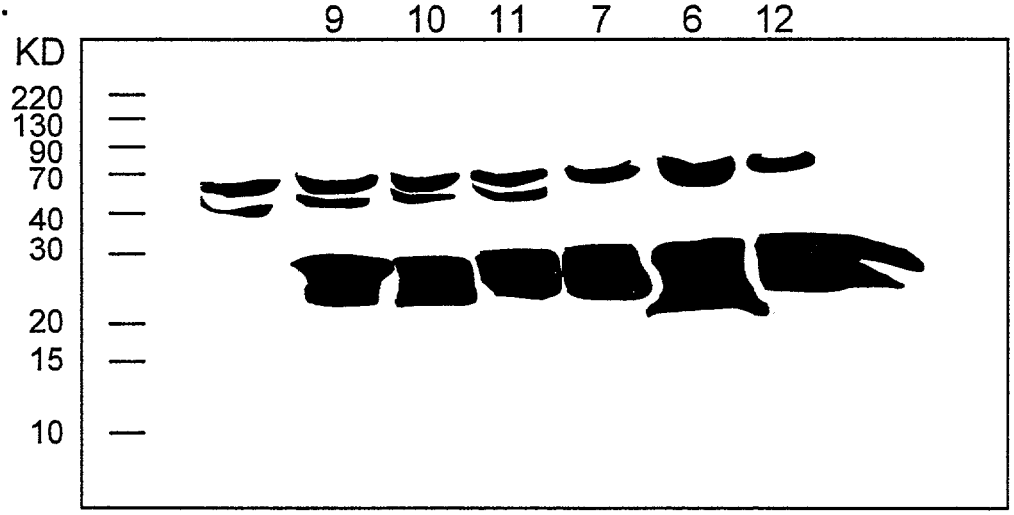
Figure 20:
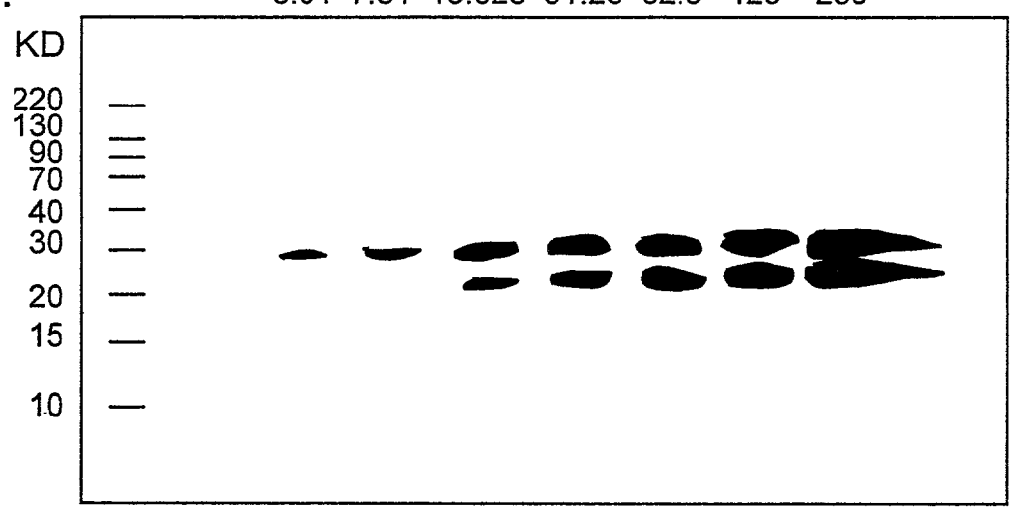

Immunoblots of CRP were performed in normal (NHP) and DIC plasma. Blot A (see FIG. 20): (used 0.2 µl plasmas for reducing SDS-PAGE/CRP Immunoblotting). Loading orientation (left to right): NHP; Pt 5; 3; 1; 2; 4; and 8. For Blot B: Loading orientation (left to right): NHP; Pt 9; 10; 11; 7; 6; 12. For Blot C: (CRP purified from DIC patient plasma) Loading orientation (left to right; ng CRP loaded): 3.91; 7.81; 15.625; 31.25; 62.5; 125; 250. The Blots were blocked with 2% (w/v) BSA in PBS, pH 7.4 and then sequentially probed with rabbit anti-human CRP-IgG (Sigma, Cat# C3527, dil 1:5000 in PBS/0.01% Tween 20) and then treated with the test detecting antibody conjugated to HRP (dil 1:25000 in PBS/0.01% Tween 20).

Figure 21:
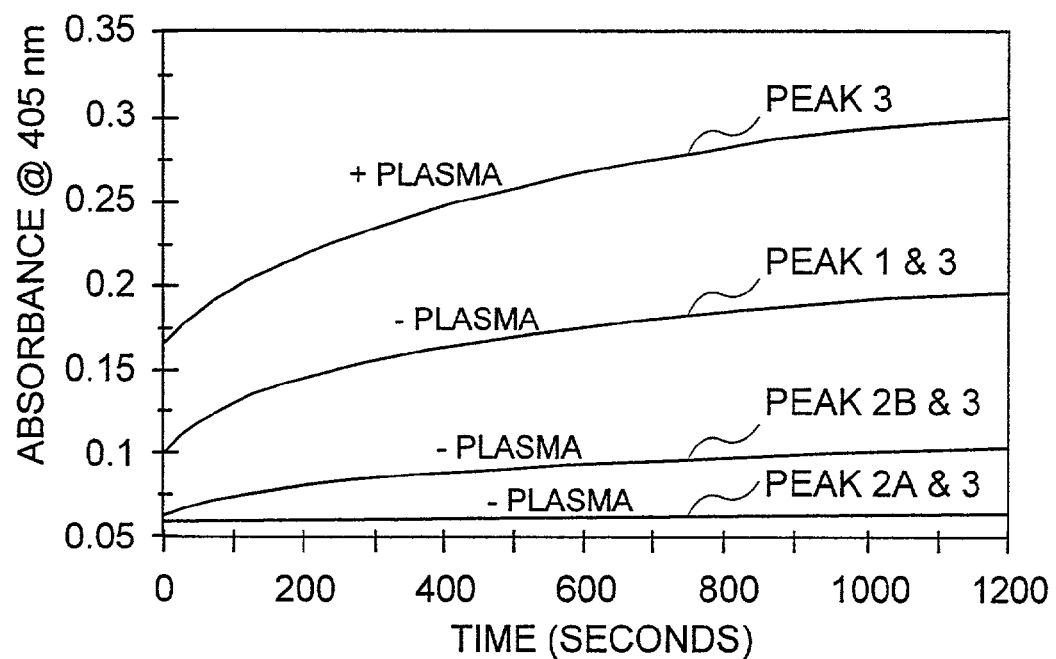
FIG. 21 illustrates the turbidity change upon adding divalent calcium to materials obtained upon Q-sepharose chromatography in the absence of plasma (except top curve).

FIG. 21 illustrates the turbidity changes upon adding divalent calcium to materials obtained upon Q-sepharose chromatography in the absence of plasma. No single peak gave a positive response, but a mixture of peak 1 and peak 3 materials did give a positive response indicating the involvement of CRP, a 300 kDa protein, and one or more other proteins in the precipitate (peak 3+plasma was the control). Table 7 is a table shows CRP amounts in µg/ml as determined by ELISA. Delta A405 nm is the maximum turbidity, change observed when patients' plasmas were recalcified on the presence of the thrombin inhibitor PPACK). Table 7, therefore, shows that patients with increased absorbance have varying elevated levels of CRP, once again indicating that more than one protein is involved in the precipitate formation.

TABLE 7

| Plasma Sample | [CRP], µg/mL | Δ 405 nm |
|---|---|---|
| Normal Human Pool | 0.73 | 0 |
| Pt #1 | 248 | 0.329 |
| Pt #2 | 277 | 0.235 |
| Pt #3 | 319 | 0.345 |
| Pt #4 | 443 | 0.170 |
| Pt #5 | 478 | 0.640 |
| Pt #6 | 492 | 0.230 |
| Pt #7 | 528 | 0.140 |
| Pt #8 | 576 | 0.640 |
| Pt #9 | 600 | 0.390 |
| Pt #10 | 639 | 0.160 |

Figure 22:
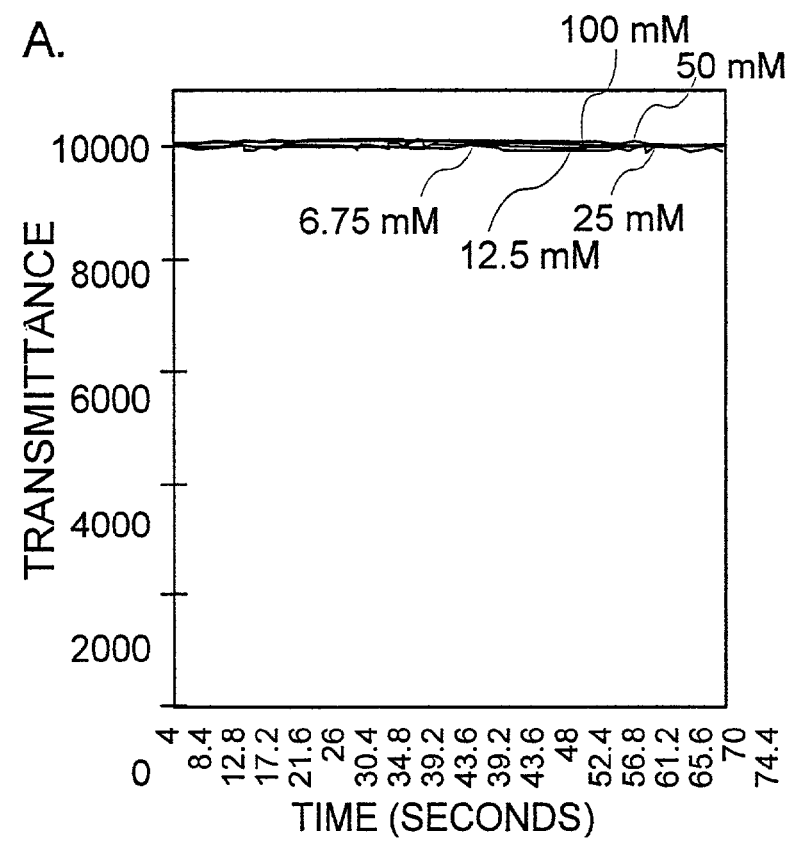
FIG. 22 shows the response to increasing calcium concentrations in optical transmission profiles. Profiles are shown for two normal patients (A, B) and two patients with DIC (c, D).
Figure 22:
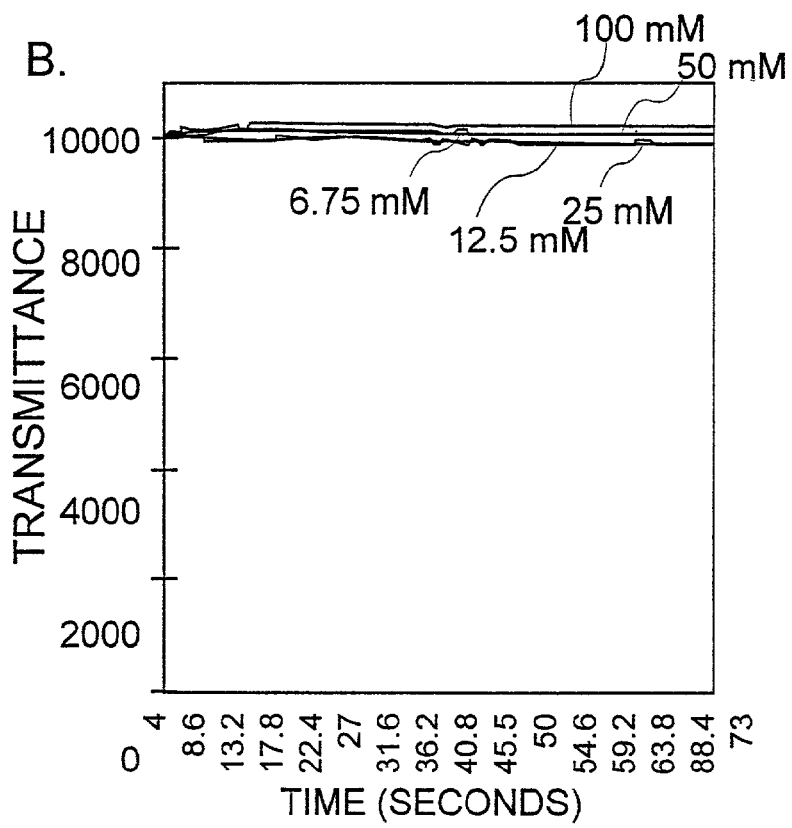
Figure 22:
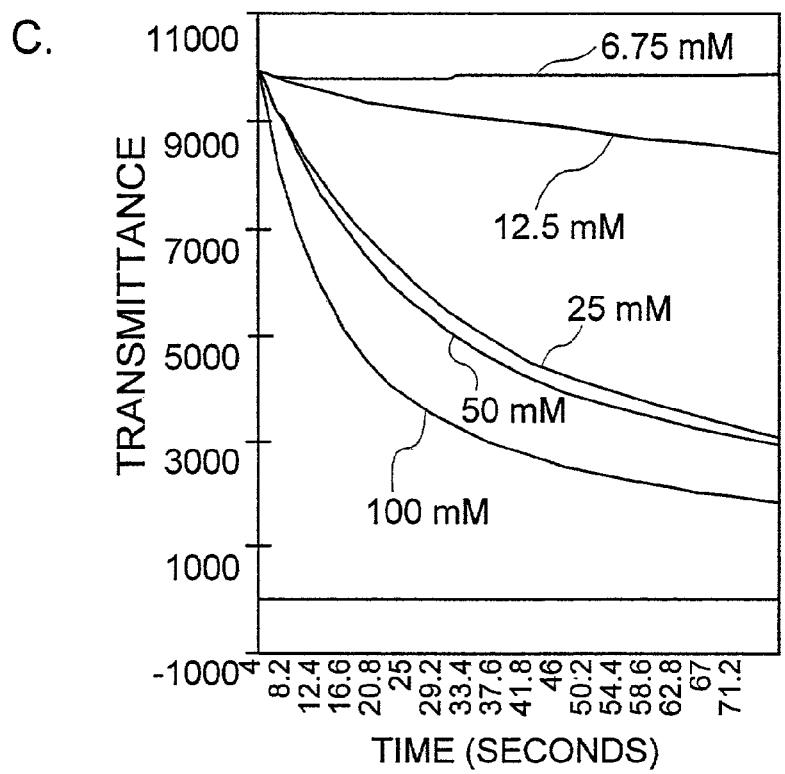
Figure 22:
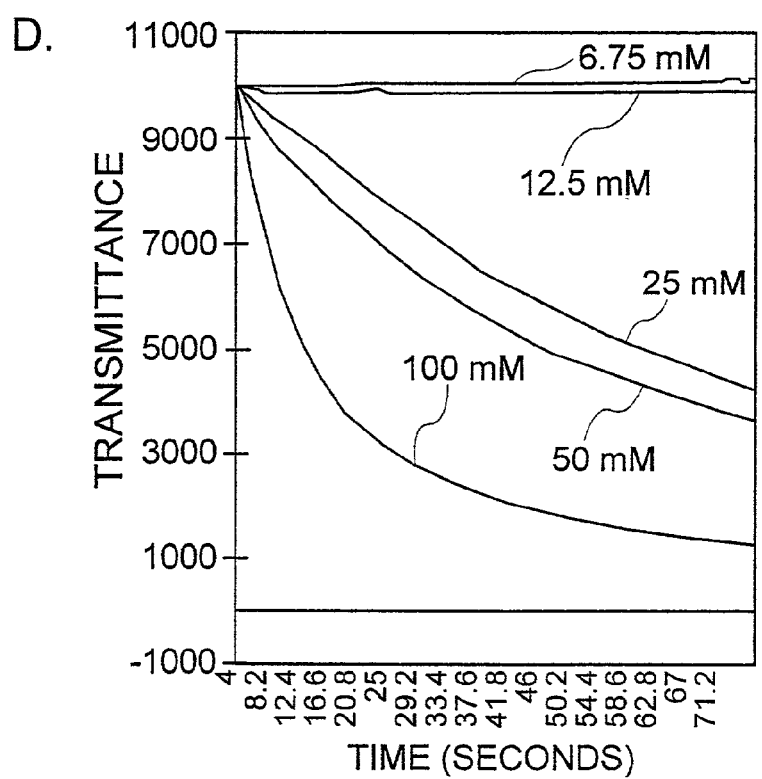

In one embodiment of the invention, the reagent to plasma ratio is varied between multiple tests using a reagent that induces precipitate formation. This variance allows for amplifying the detection of the precipitate formation by optimization of reagent to plasma ratio (e.g. varying plasma or reagent concentrations). In the alternative, the slope due to the precipitate formation can be averaged between the multiple tests. As can be seen in FIG. 22, the response to increasing calcium concentrations is shown in optical transmission waveform profiles. Panels A and B show two normal patients where calcium concentrations were varied (no clotting agents used), whereas the panels C and D show two patients with haemostatic dysfunction (DIC in these two cases) where the metal cation (calcium) concentration was varied (the calcium alone being incapable of any substantial fibrin polymerization).

Figure 23:
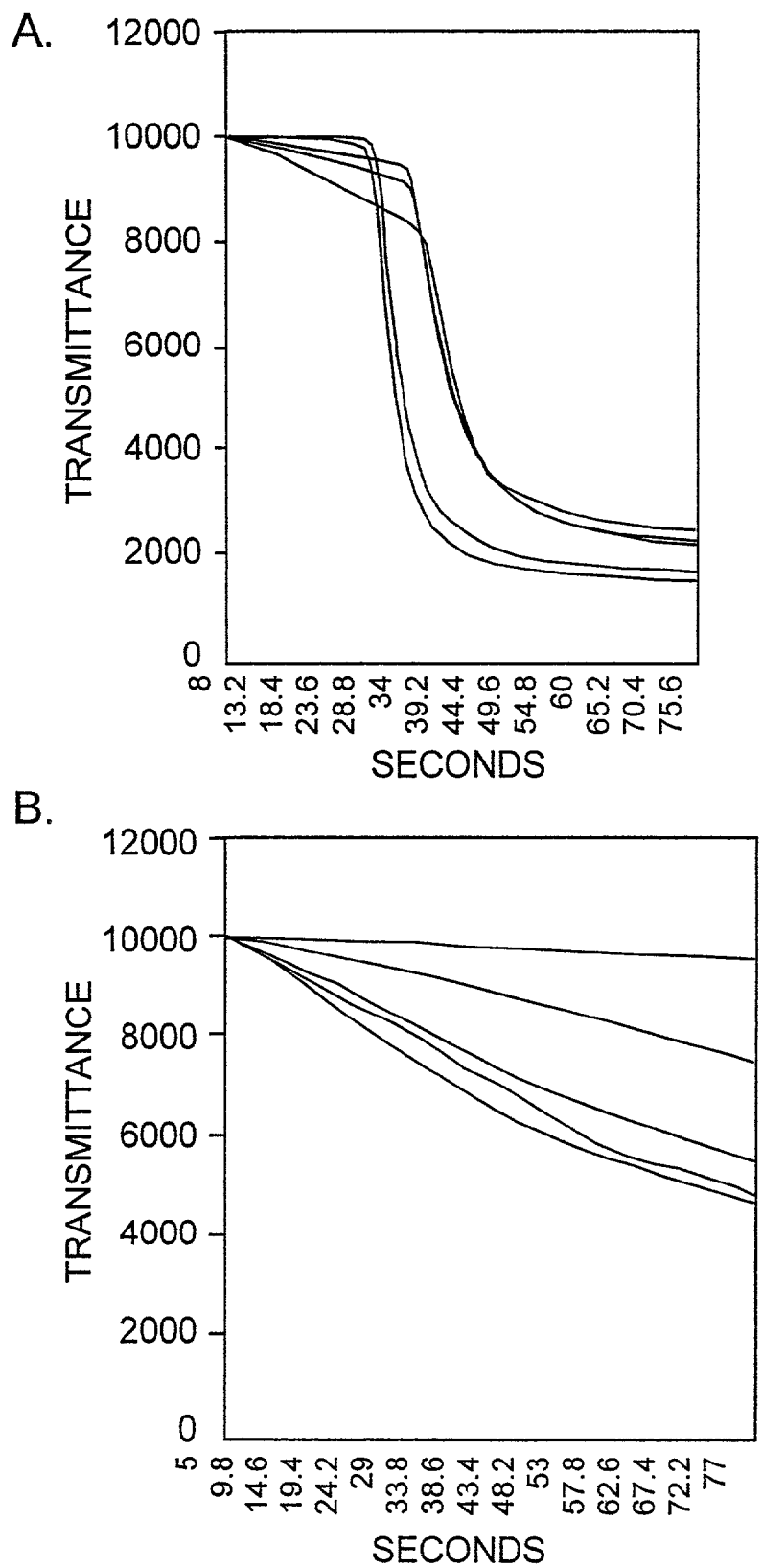
FIG. 23 shows optical transmission profiles for calcium chloride alone (B) or in combination with APTT reagent (A). Numbers indicate patient ID numbers.
Figure 24:
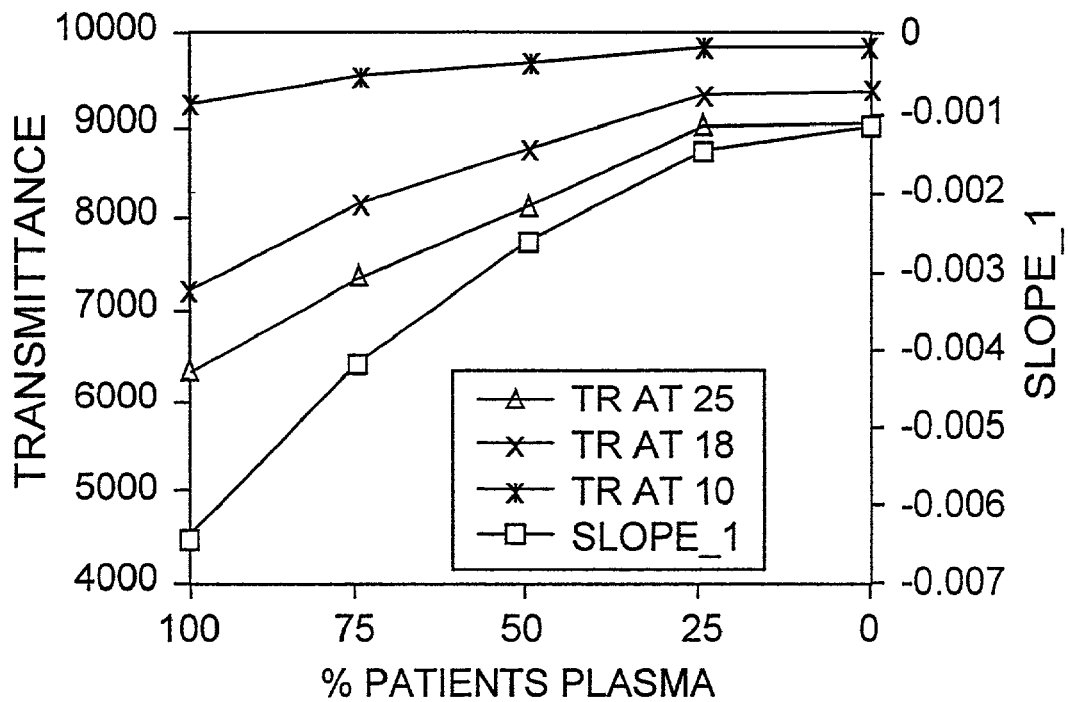
FIG. 24 is a calibration curve with heparin.

Though precipitate formation is capable of being detected in patients with haemostatic dysfunction when a clotting agent is used, it is beneficial that the reagent used is capable of forming the precipitate without fibrin polymerization. As can be seen in FIG. 23, the slope is more pronounced and more easily detectable when a reagent such as calcium chloride is used alone (panel A) as compared to when it is used along with a clotting reagent such as an APTT reagent (panel B). As can be seen in FIG. 24, when a clot inhibitor was added (in this case heparin), all parameters including slope_1 gave good results, and slope_1 showed the best sensitivity. For the above reasons, a reagent capable of precipitate formation in the absence of fibrin polymerization and/or a clot-inhibitor are preferred.

Figure 25:
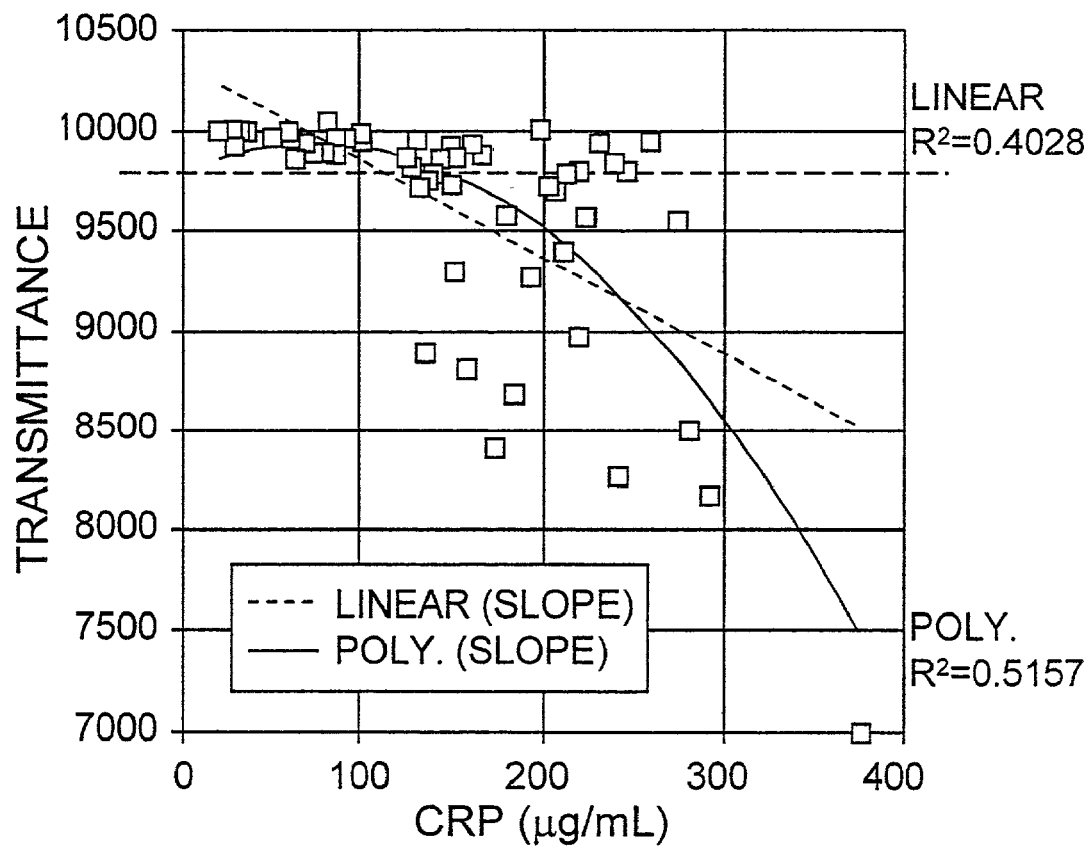
FIG. 25 shows CRP levels in 56 ITU patients plotted against transmittance at 18 seconds.
Figure 26:
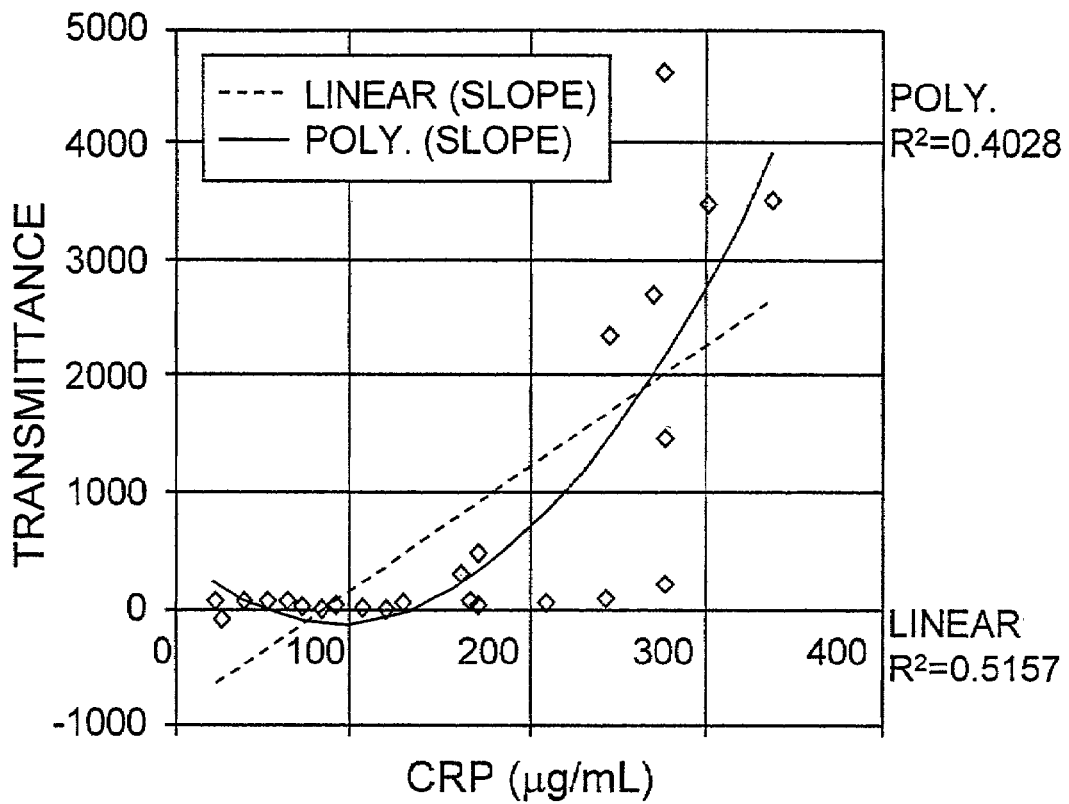
FIG. 26 shows more samples with CRP and decrease in transmittance at 18 seconds (10000—TR18).

As can be seen in FIG. 25, CRP levels from 56 ITU patients were plotted against transmittance at 18 seconds. The dotted line is the cut-off for an abnormal transmittance at 18 seconds. FIG. 26 shows more samples with CRP and decrease in transmittance at 18 seconds (10000—TR18). These figures indicate that patients with abnormal transmittance levels due to precipitate formation all have increased levels of CRP. However, not all patients with increased levels of CRP have abnormal transmittance levels thus indicating that more than CRP is involved in the precipitate.

In a further embodiment of the invention, the formation of the precipitate comprising a complex of proteins including CRP is detected and/or quantitated, by the use of a latex agglutination assay. In this method, antibodies are raised against either the 300 kDa protein or CRP. Whether monoclonal or polyclonal antibodies are used, they are bound to suitable latex and reacted with a patient test sample or preferably with the precipitate itself having been separated from the rest of the patient plasma, in accordance with known methods. The amount of agglutination of the latex is proportional to the amount of the CRP complex in the sample.

Alternatively, immunoassays can be performed, such as ELISA'S, according to known methods (sandwich, competition or other ELISA) in which the existence and/or amount of the complex of proteins is determined. For example, an antibody bound to solid phase binds to CRP in the CRP protein complex. Then, a second labeled antibody is added which also binds to CRP in the CRP protein complex, thus detecting the complex of proteins. In the alternative, the second labeled antibody can be specific for the 300 kDa protein in the complex. Or, in a different assay, the antibody bound to solid phase can bind to the 300 kDa protein in the complex, with the second (labeled) antibody binding either to the 300 kDa protein or to CRP. Such immunoassays could likewise be adapted to be specific for SAA. The above techniques are well known to those of ordinary skill in the art and are outlined in *Antibodies, A Laboratory Manual*, Harlow, Ed and Lane, David, Cold Spring Harbor Laboratory, 1988, the subject matter of which is incorporated herein by reference.

After further studies, it has been determined that the "300 kDa" protein is in fact the Apo(B)-100 compound of VLDL (very low density lipoprotein) having a molecular weight of from 500 to 550 kDa. There can be additional lipoprotein complexes in the precipitate as well, including CRP-LDL (CRP complexed with low density alipoprotein), CRP-IDL (CRP complexed with intermediate density lipoprotein), CRP-chylomicrons, CRP-HDL (CRP complexed with high density lipoprotein) and SAA-VLDL (serum amyloid A complexed with VLDL).

Figure 34:
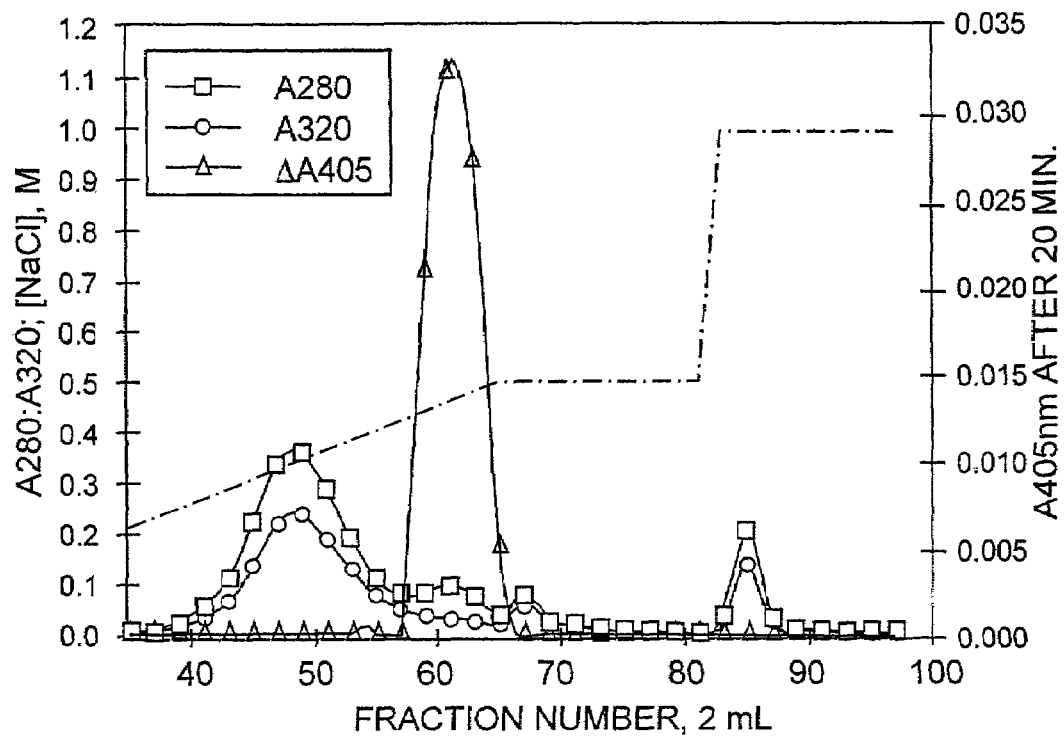
FIG. 34 is an illustration of peaks 1 and 3 recovered from a Q-Sepharose column of washed calcium precipitate.
Figure 35:
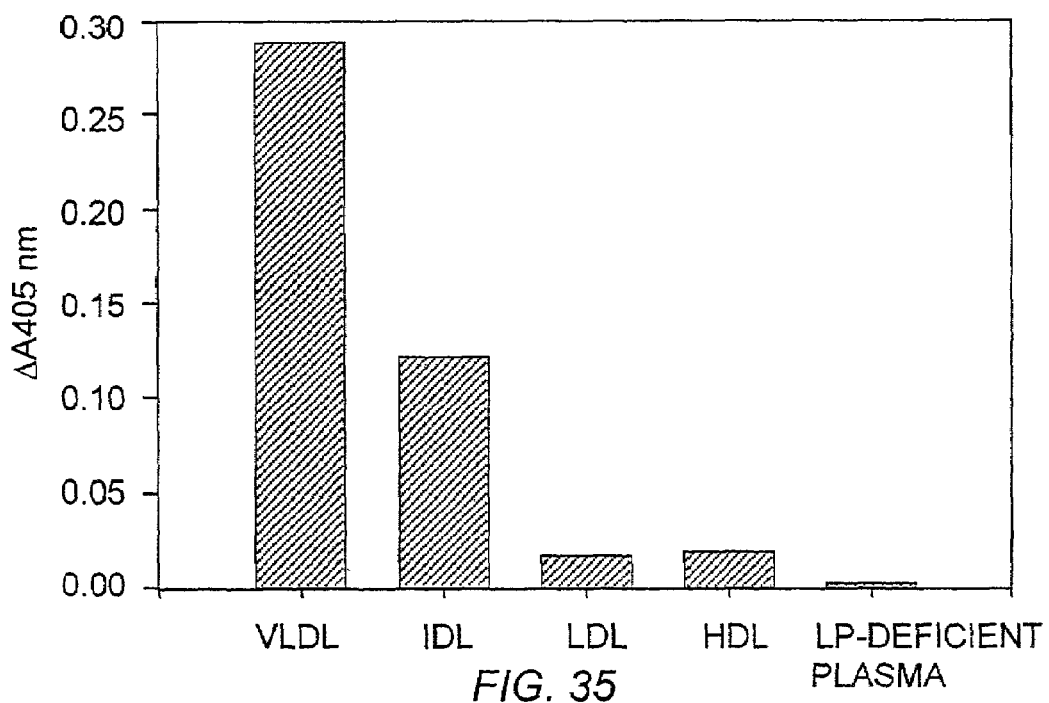
FIG. 35 is a graph depicting the turbidity changes associated with the addition of excess CRP and $Ca^{++}$ to isolated lipoproteins from normal plasma.
Figure 36:
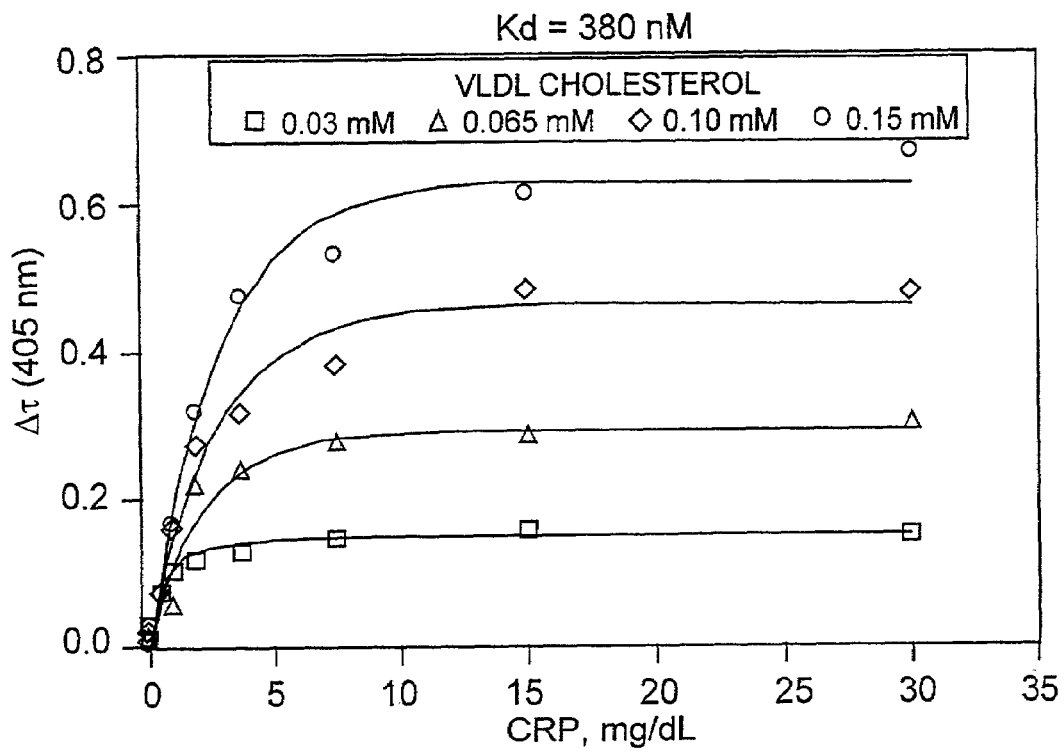
FIG. 36 is a graph depicting the quantitation of the interaction between CRP and VLDL. Recombinant CRP and normal VLDL were mixed at various concentrations in buffer and maximum turbidity changes were then recorded after adding $Ca^{2+}$. The VLDL concentrations (measured as cholesterol) were: 0.030 mM (squares), 0.065 mM (triangles), 0.10 mM (diamonds), and 0.15 mM (circles). The lines are regression lines.
Figure 37:
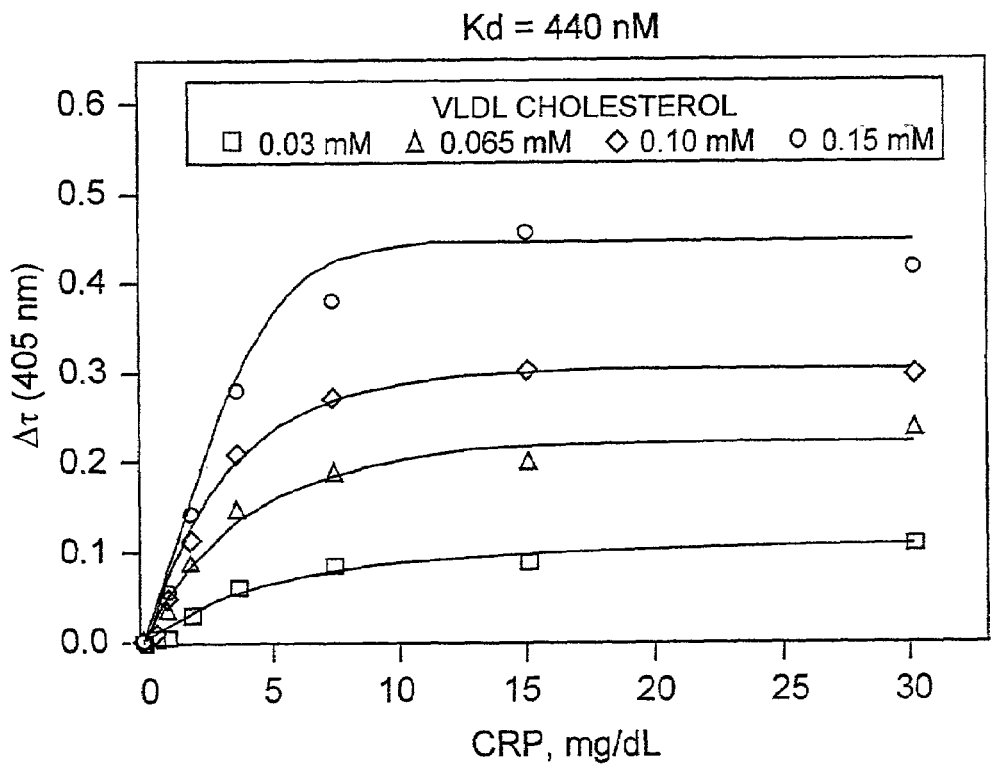
FIG. 37 is a graph depicting the quantitation of the interaction between CRP and VLDL. Recombinant CRP and normal VLDL were mixed at various concentrations in lipoprotein deficient plasma and maximum turbidity changes ere then recorded after adding $Ca^{2+}$. The VLDL concentrations (measured as cholesterol) were: 0.030 mM (squares), 0.065 mM (triangles), 0.10 mM (diamonds), and 0.15 mM (circles). The lines are regression lines.
Figure 38:
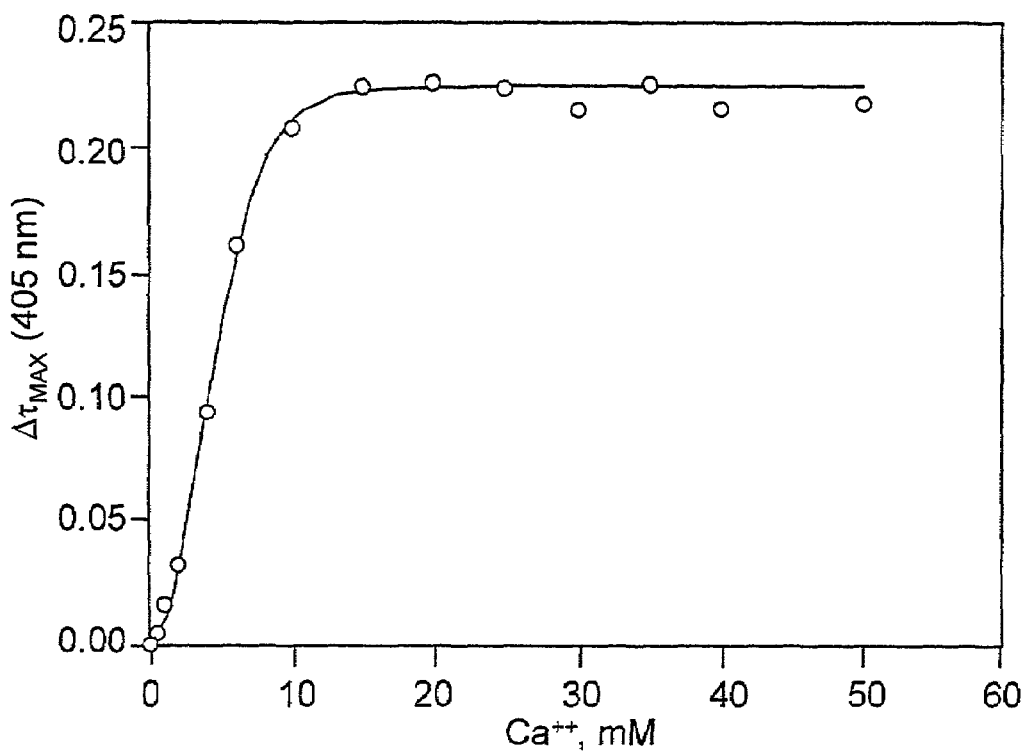
FIG. 38 is a graph depicting the calcium concentration dependence of formation of the VLDL/CRP complex. Complex formation is half maximal at 5.0 mM calcium.
Figure 39:
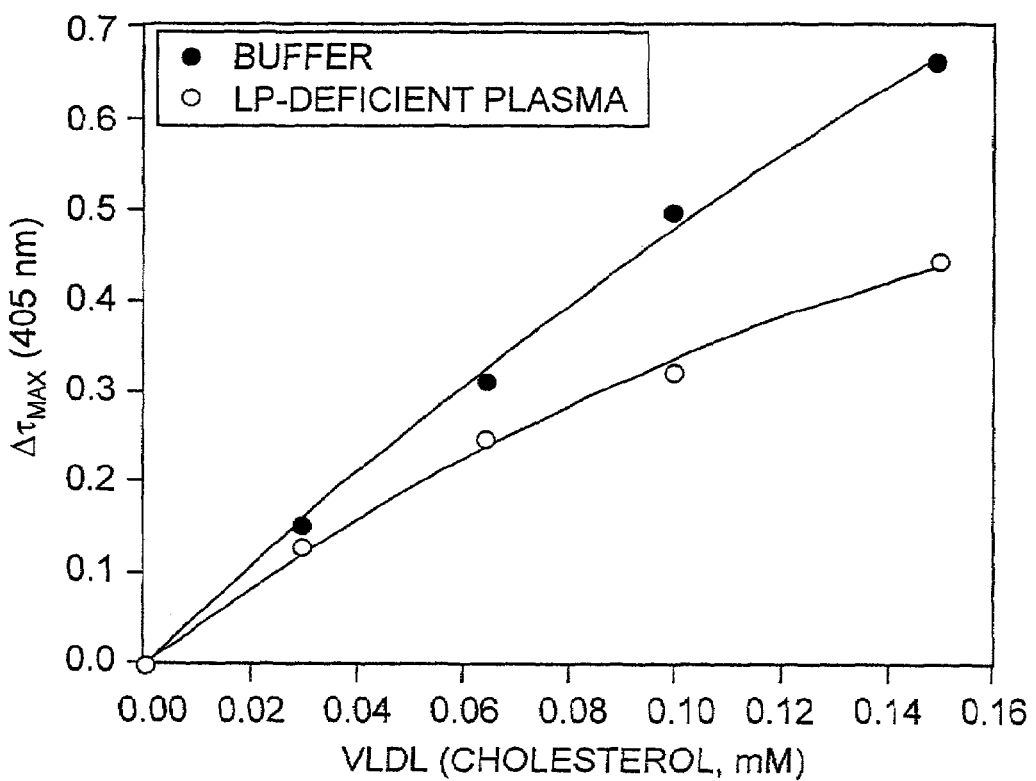
FIG. 39 is a graph depicting the turbidity changes associated with varying concentrations of VLDL in the presence of excess CRP in buffer and in lipoprotein-deficient plasma.
Figure 40:
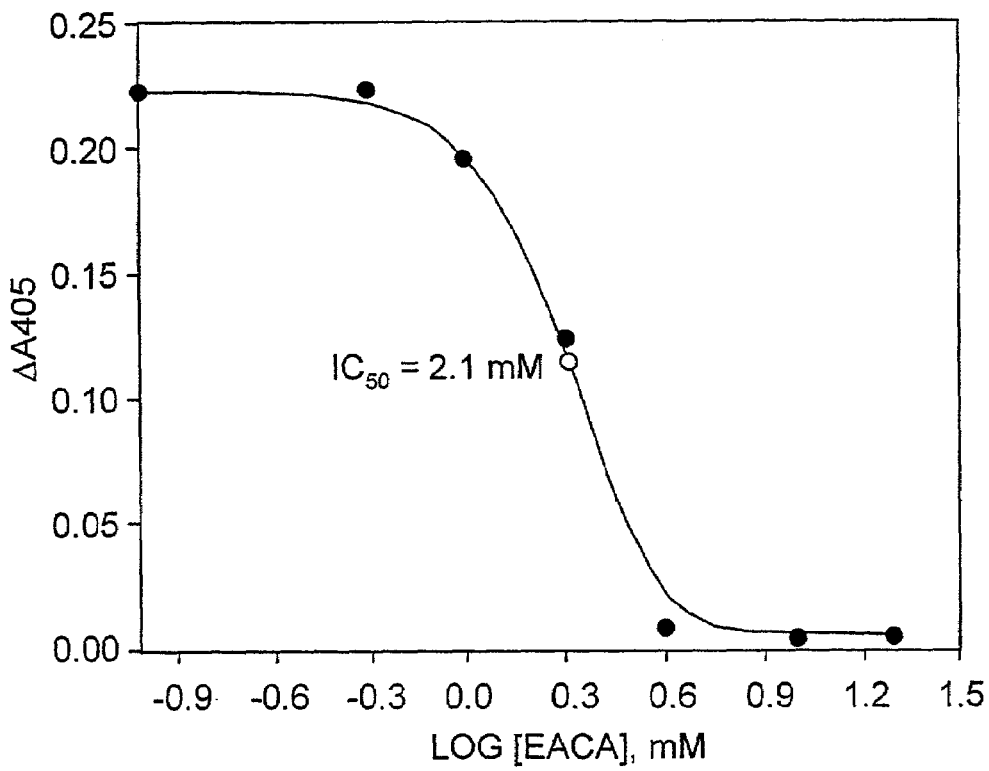
FIG. 40 is a graph depicting the inhibition of VLDL/CRP complex formation by EACA. The $IC_{50}$ for inhibition by EACA is 2.1 mM.
Figure 41:
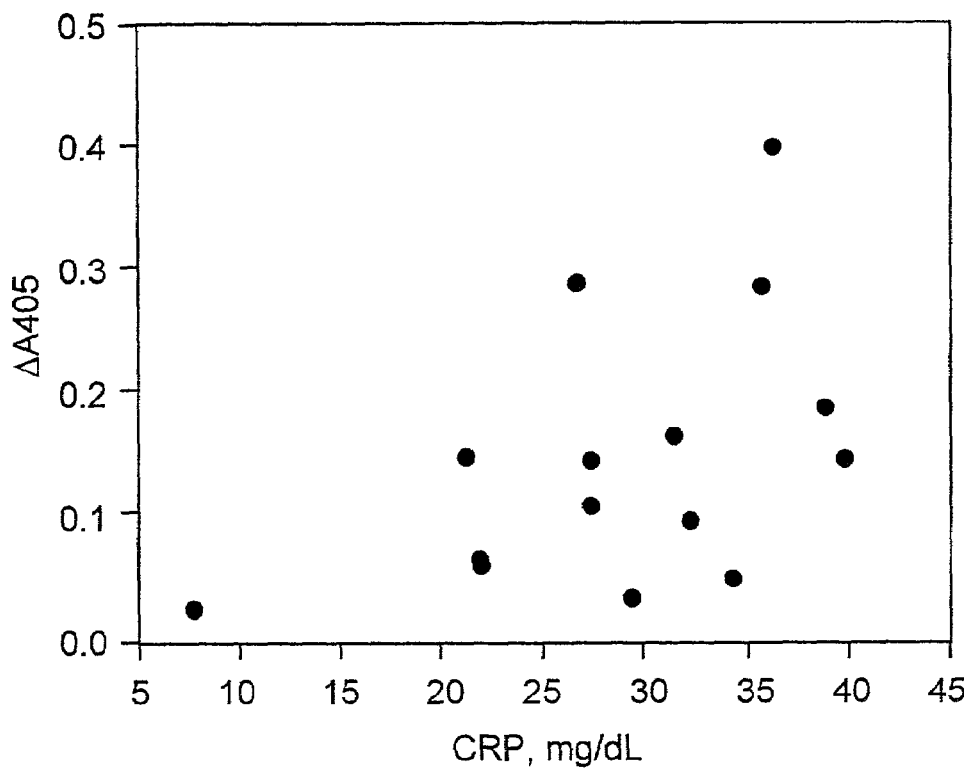
FIG. 41 is a graph depicting turbidity change versus varying CRP concentration.

In order to characterize the components of the complex, the precipitate was dispersed in citrate and subjected to anion exchange chromatography (see FIG. 34). The procedure yielded two major peaks (referred to hereinafter as "peak 1" and "peak 3"), the first of which was very turbid. The turbidity was obvious to the eye and was quantified by absorbance measurements at 320 nm. Fractions were tested for activity (turbidity formation in normal plasma upon recalcification). Only peak 3 exhibited turbidity when added to normal plasma.

In order to further characterize the precipitated material, lipid and protein analyses were performed. In addition, fractions obtained after anion exchange chromatography were subjected to SDS-PAGE, immunoblotting, and amino acid sequence analysis. The isolated materials were shown to comprise proteins, phospholipids, cholesterol and triglycerides in proportions typical of very low density lipoproteins (VLDL and IDL). See Table 8. Fractionation by anion exchange and SDS-PAGE showed that the precipitate contains Coomassie blue staining protein bands with apparent molecular masses of 500 kDa, 22 kDa and 10 kDa. The 22 kDa protein yielded an amino terminal sequence QTDM-S_KAFV (SEQ ID NO:1), which identified the protein as C-reactive protein. The 10 kDa protein gave two residues at each cycle in the sequenator.

They were consistent with serum amyloid A beginning with amino acids 18 and 19. The 500 kDa species did not yield a sequence, likely due to the small molar amounts of it. The high molecular weight of this band, however, was consistent with apo-lipoprotein B, the major protein component of VLDL.

TABLE 8

| Lipoprotein class | Protein | PL | UC | CE | TG |
|---|---|---|---|---|---|
| VLDL | 10% | 15% | 6% | 14% | 53% |
| IDL | 18% | 22% | 7% | 23% | 31% |
| LDL | 25% | 21% | 9% | 42% | 4% |

PL = phospholipid, UC = unesterified cholesterol, CE = cholesteryl esters, TG = triacylglycerol.

After fractionation, the high molecular weight band and SAA were obtained in peak 1, and CRP was obtained in peak 3 (see FIG. 34). Peaks 2a and 2b were seen in FIG. 18 but not FIG. 34 because, in the assay run for FIG. 18, the amount of protein and lipoprotein in the sample exceeded the capacity of the column. When the column is not overloaded as in the assay run for FIG. 34, peaks 2a and 2b do not appear. The precipitate and materials in peaks 1 and 3 were assessed by immunoblotting for Apo(B)-100, CRP and SAA. The results were consistent with the identification of the 500 kDa material as Apo(B)-100, the 22 kDa material as CRP, and the 10 kDa material as SAA.

The starting material, the materials in peaks 1 and 3, and a mixture of them were recalcified in the absence of plasma to determine which component or components were needed for the formation of a precipitate. The results showed that the starting material, but not isolated peak 1 or peak 3 components, formed a precipitate when recalcified. The mixture of peaks 1 and 3, however, did form a precipitate. Therefore, it can be concluded that VLDL and CRP are minimally required to form the precipitate. The procedure was repeated with at least 10 different positive plasmas and the results were the same. Occasionally, however, SAA was not recovered in the isolated peaks. Nonetheless, precipitates formed with VLDL and CRP in the absence of SAA. It is therefore concluded that SAA can be included in the precipitate/complex, but is not necessary for its formation.

Figure 27:
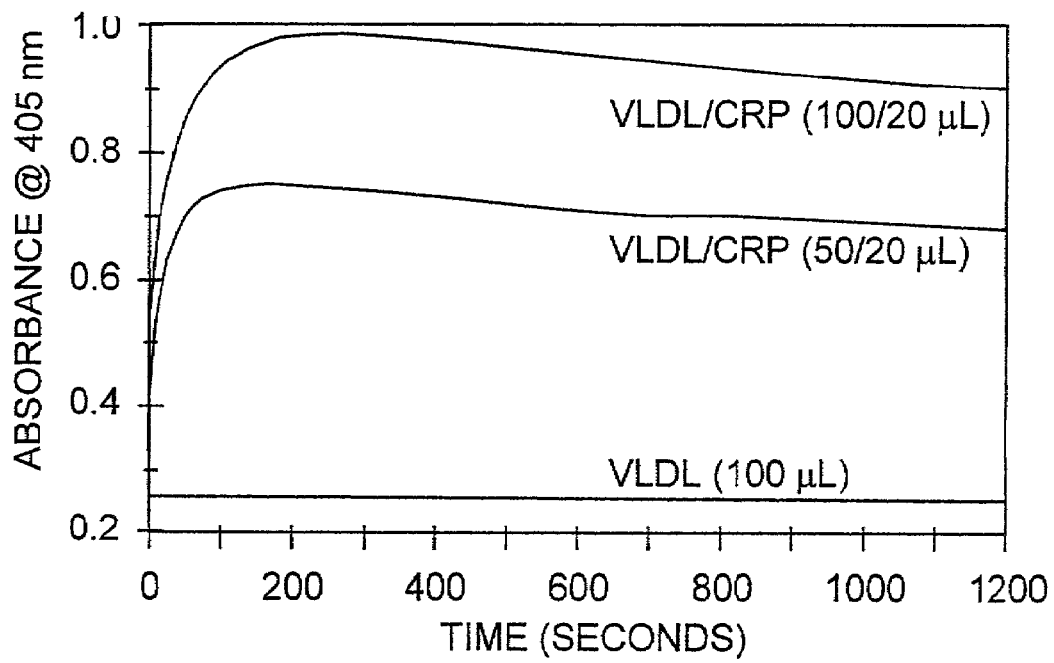
FIG. 27 depicts a reconstitution experiment showing the effect on turbidity of combining VLDL and CRP (Peak 3), compared to VLDL alone. The starting concentration of VLDL for this experiment was 0.326 mg/mL.
Figure 28:
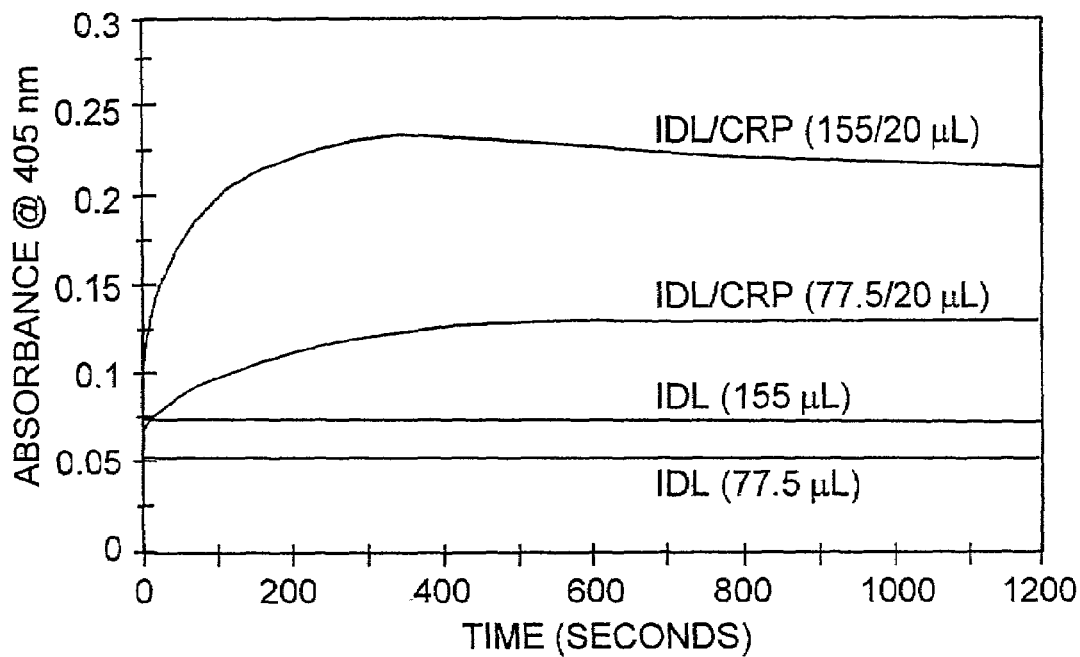
FIG. 28 depicts a reconstitution experiment showing the effect on turbidity of combining IDL and CRP (Peak 3) compared to IDL alone. The starting concentration of IDL for this experiment was 0.06797 mg/mL.
Figure 29:
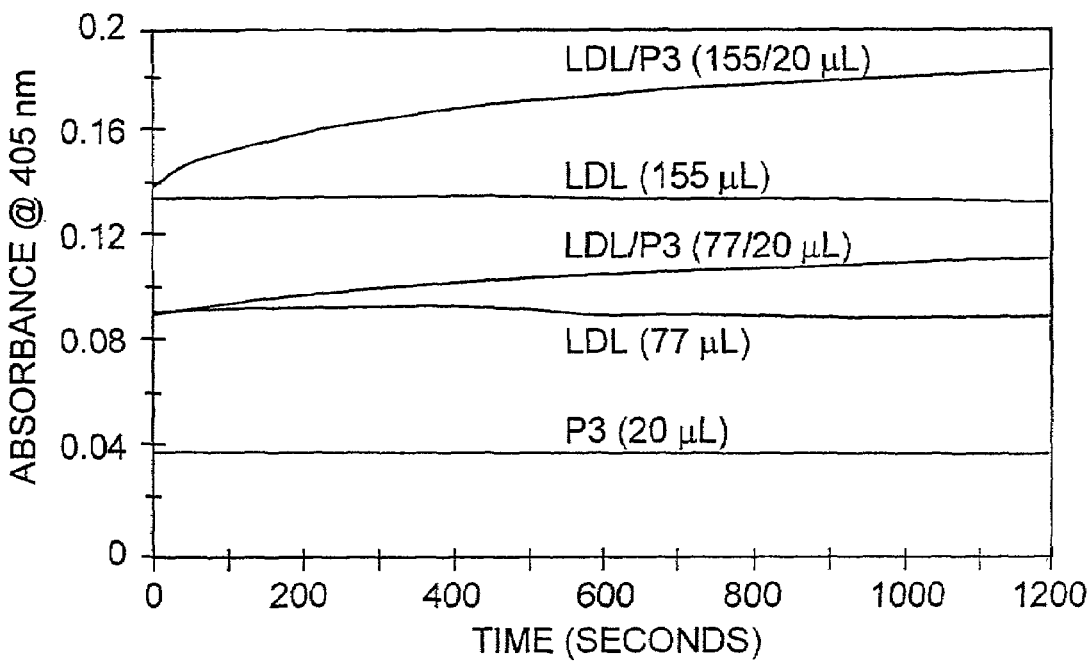
FIG. 29 depicts a reconstitution experiment showing the effect on turbidity of combining LDL and CRP compared to LDL alone and CRP (Peak 3) alone. The starting concentration of LDL for this experiment was 0.354 mg/mL.
Figure 30:
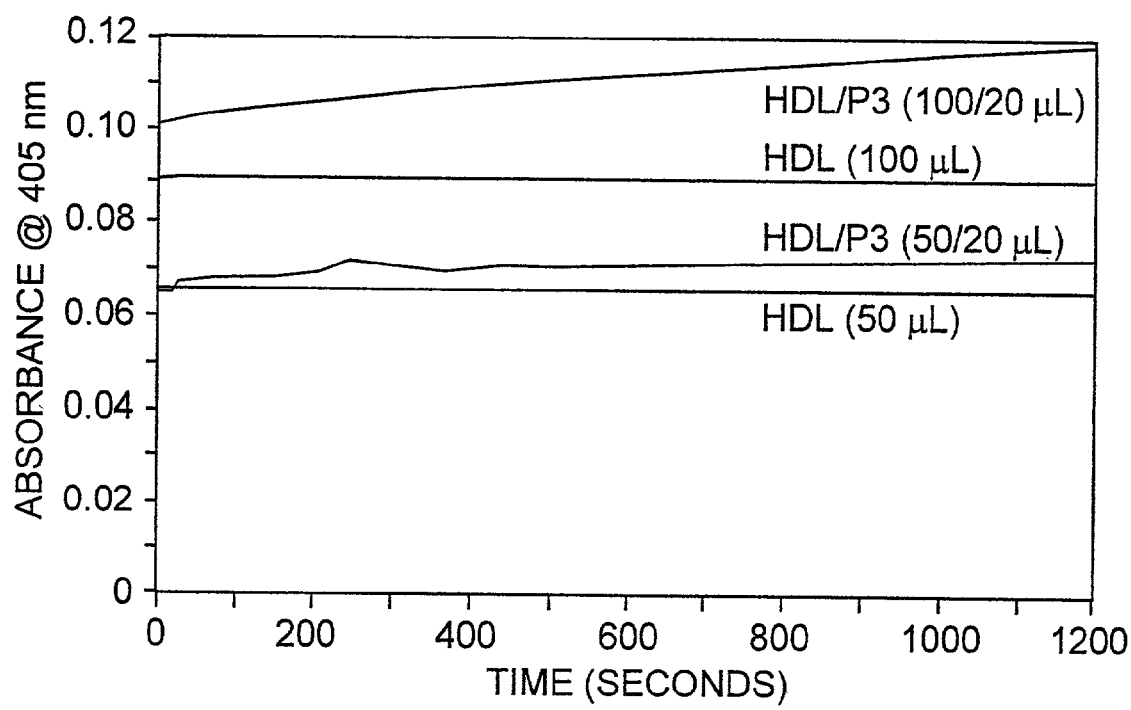
FIG. 30 depicts a reconstitution experiment showing the effect on turbidity of combining HDL and CRP (Peak 3) as compared to HDL alone. The starting concentration of HDL for this experiment was 1.564 mg/mL.

Reconstitution experiments were run to verify the ability of the above-mentioned complexes to form. As can be seen in FIG. 27, VLDL and P3 (Peak 3=CRP, see FIG. 18) at varying concentrations (100/20 μl: VLDL/CRP and 50/20 μl VLDL/CRP) shows an increase in absorbance due to turbidity, in comparison with VLDL alone. Likewise, as can be seen in FIGS. 28 and 29, IDL and CRP, as well as LDL and CRP (and to a lesser extent HDL and CRP as can be seen in FIG. 30) also cause an increase in turbidity when combined together. And, as can be further seen in Table 9, the different lipoproteins have different calcium-dependent turbidity activity in the presence of purified CRP.

TABLE 9

| Sample | Total Vol Isolated (μL) | [Protein] (mg/mL) | Excursion (ΔA405 nm/μL) | Total Protein (mg) | Total Excursion (ΔA405 nm) |
|---|---|---|---|---|---|
| VLDL | 900 | 0.326 | 0.0096 | 0.29 | 8.64 |
| IDL | 2000 | 0.068 | 0.0018 | 0.136 | 3.60 |
| LDL | 1500 | 0.354 | 0.00033 | 0.531 | 0.50 |
| HDL | 2000 | 1.564 | 0.00028 | 3.13 | 0.56 |

Interestingly, it has been found that the turbidity caused when adding a divalent metal cation such as calcium to patient plasmas which exhibit the characteristic slope (even in the absence of clot formation) due to the above-noted complexes, does not correlate with the level of CRP in the patient plasma. Therefore, the present invention is not directed to detecting CRP levels per se, but rather detecting CRP complexed with lipoproteins (VLDL in particular). In the present invention, it is believed that the formation of the complex ex vivo (after adding a divalent metal cation to citrated plasma) corresponds to the existence of the complex in vivo, which is possibly an indication of the inability of that patient to clear the formed complex(es). Clearance of VLDL and IDL from the plasma by the liver is directed by their surface apo E. Therefore, if there is defective clearance of the complex(es) from the plasma, it may be due to a mutated, fragmented or otherwise defective apo E, or to an oxidized, mutated or fragmented lipoprotein (e.g. beta-VLDL, an oxidized LDL, an abnormal LDL called Lp(a), or an otherwise abnormal version of VLDL, LDL or IDL). IDL, LDL, Lp(a) and VLDL all have Apo(B)-100, which, if abnormal, may play a roll in the improper clearance of the complex(es) from the plasma. Of course a mutated, fragmented or otherwise abnormal form of CRP could also play a role in improper clearance of the complex from plasma, resulting in the characteristic slope in the clot waveform. As can be seen in Table 10, the change in absorbance due to complex formation does not correlate with the amount of CRP in the patient sample. The level of CRP is not generally limiting in complex formation. In fact, it was found that patients can have elevated levels of CRP and yet their plasmas do not exhibit the waveform slope mentioned herein-above. Adding additional VLDL, however, will cause those samples to undergo a turbidity change (in the presence of certain divalent metal cations such as calcium, of course).

TABLE 10

| Plasma Sample | [CRP] μg/mL | Change at A405 nm with 0.05U PP |
|---|---|---|
| Normal Human Pooled Plasma | 3.24 | 0 |
| Pt #1 | 204.08 | 0.359 |
| Pt #2 | 273.34 | 0.230 |
| Pt #3 | 331.47 | 0.609 |
| Pt #4 | 333.77 | 0.181 |
| Pt #5 | 355.48 | 0.129 |
| Pt #6 | 361.81 | 0.122 |
| Pt #7 | 389.53 | 0.308 |

TABLE 10-continued

| Plasma Sample | [CRP] µg/mL | Change at A405 nm with 0.05U PP |
|---|---|---|
| Pt #8 | 438.56 | 0.531 |
| Pt #9 | 443.62 | 0.137 |

Figure 31:
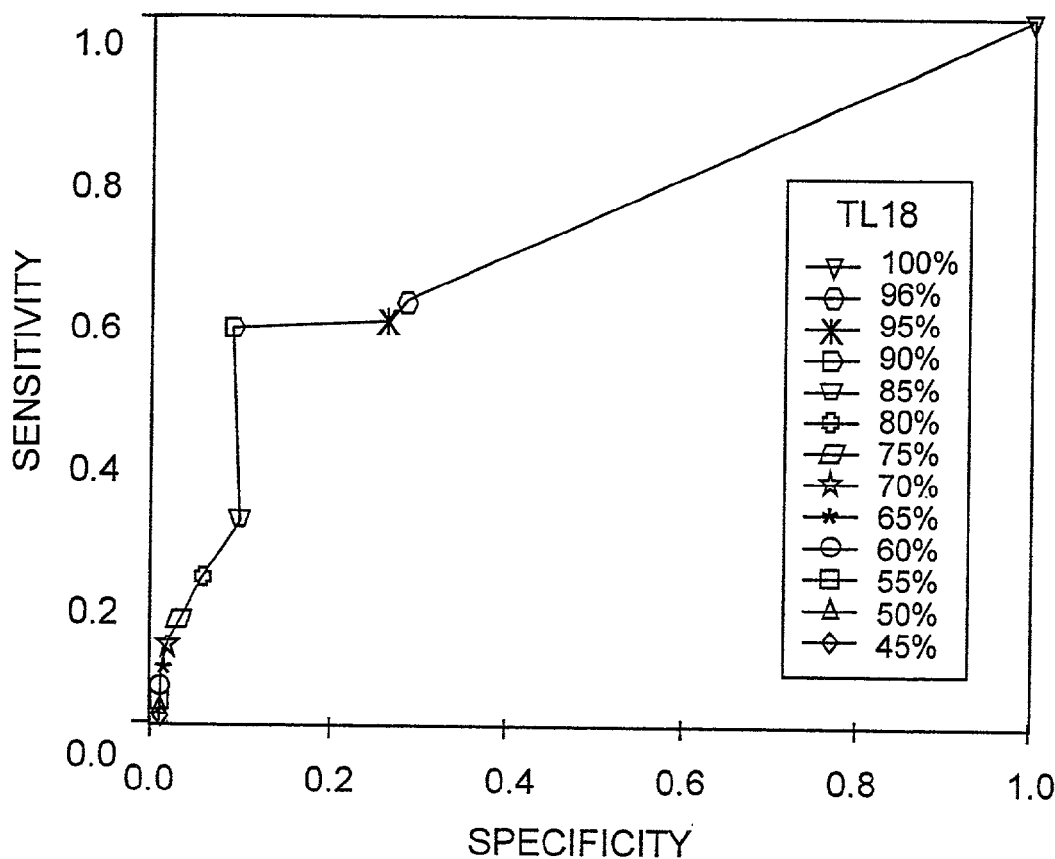
FIG. 31 is a ROC plot of sensitivity vs. specificity.

It has also been found that the detection of precipitate formation correlates to clinical outcome, specifically patient death. Of 529 admissions to an intensive care unit, there were 178 deaths (34% baseline probability of death). The positive predictive value of death increased to 50% when patients had transmittance readings at 18 seconds of 96%, or a slope of −0.00075 or less. This predictive power increased to 77% when transmittance readings at 18 seconds were less than 65% (slope of −0.00432 or less). Using receiver operator characteristics analysis, the optimum level that maximized predictivity without compromising sensitivity was transmittance at 18 seconds cut-off value of 90% (or slope cut-off value of −0.00132 or less). The predictive value of death at this cut-off was found to be 75%. Additional data is shown in Table 11, where, for patient populations of 10 or more, the positive predictive value generally increases as the negative slope value or transmittance decreases. Thus, not only is the existence of the slope or decreased transmittance a predictor of future clinical outcome (e.g. likelihood of death), but in addition, the greater the formation of the precipitate (the greater the decrease in transmittance or increase in slope), the greater the predictor of the impending death. FIG. 31 shows a ROC plot of sensitivity vs. specificity.

TABLE 11

| TL 18 ≦ (%) | Slope_1 ≧ | Total No. Patients | Total No. Deaths | PPV (%) |
|---|---|---|---|---|
| 96 | −0.00075 | 209 | 106 | 51 |
| 95 | −0.00078 | 195 | 101 | 52 |
| 90 | −0.00132 | 131 | 99 | 75 |
| 85 | −0.00184 | 84 | 49 | 58 |
| 80 | −0.00265 | 56 | 35 | 62 |
| 75 | −0.00315 | 35 | 25 | 71 |
| 70 | −0.00370 | 26 | 19 | 73 |
| 65 | −0.00432 | 18 | 14 | 78 |
| 60 | −0.00490 | 12 | 9 | 75 |

Data suggests that 25% of intensive care unit admissions will have a transmittance value at 18 seconds of 90% or less (slope −0.00132 or less) during their clinical course. Thus, the detection of complex formation can be a useful tool in predicting which patients are likely to die (and which in these group are more likely to die than others based on having a more severe decrease in slope or transmittance, and to allow for aggressive intervention with the hopes of preventing the (likely) impending death. The monitoring of the slope is also a way for monitoring the effects of the intervention.

Therefore, in one embodiment of the invention, the likelihood of system failure or mortality of a patient (e.g. in an intensive care setting) is determined by adding one or more reagents to a test sample from a patient comprising at least a component of a blood sample in order to cause formation of a precipitate comprising an acute phase protein and a lipoprotein. Then, the formation of the precipitate is measured, followed by correlating the formation of the precipitate formation to the likelihood of system failure or mortality of the patient. The method can be performed multiple times (e.g. daily, weekly, etc.) in order to monitor the effectiveness of a patient's therapy. The predictive value of this method alone or in combination with other medical indicators is clearly better than the predictive value without the test. The method also includes measuring the formation of the precipitate over time, such as with an automated analyzer using optical transmittance and/or absorbance. And, the amount of precipitate detected over time (or as a final endpoint) can be correlated to the probability of mortality (the greater the precipitate formation, the greater the likelihood of system failure or mortality, and vice versa). Also, the precipitate formation in this embodiment can form even in the absence of fibrin polymerization.

Figure 32:
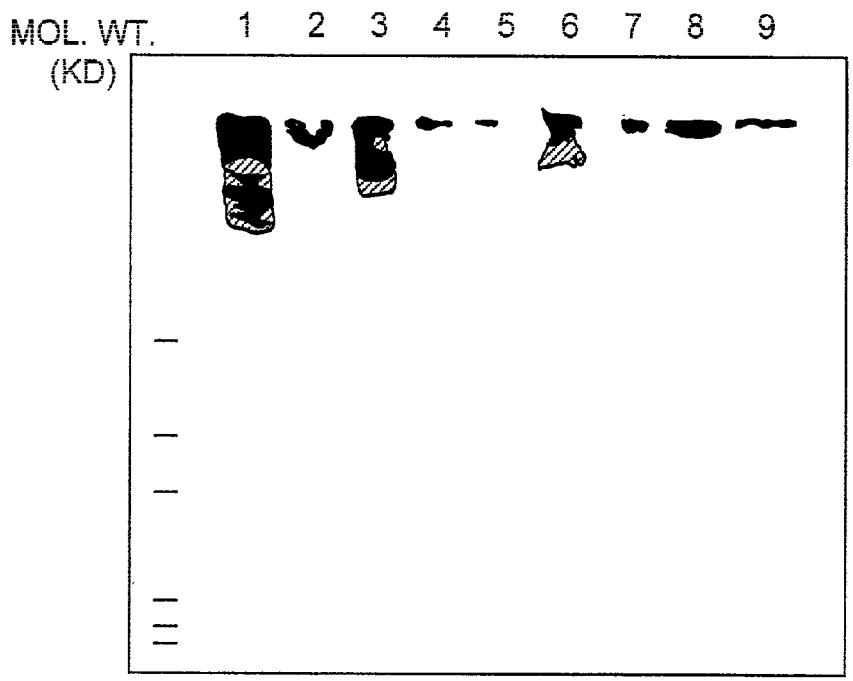
FIG. 32 is an immunoblot for apo(B)-100. Lane 1 is protein isolated from normal human plasma, lanes 2–5 are protein samples isolated from DIC patient plasma, and lanes 6–9 are calcium precipitates of protein samples from the same DIC patients in lanes 2–5. The monoclonal apo(B)-100 antibody was used at a 1/5000 dilution. Proteins were visualized with ECL reagents.
Figure 33:
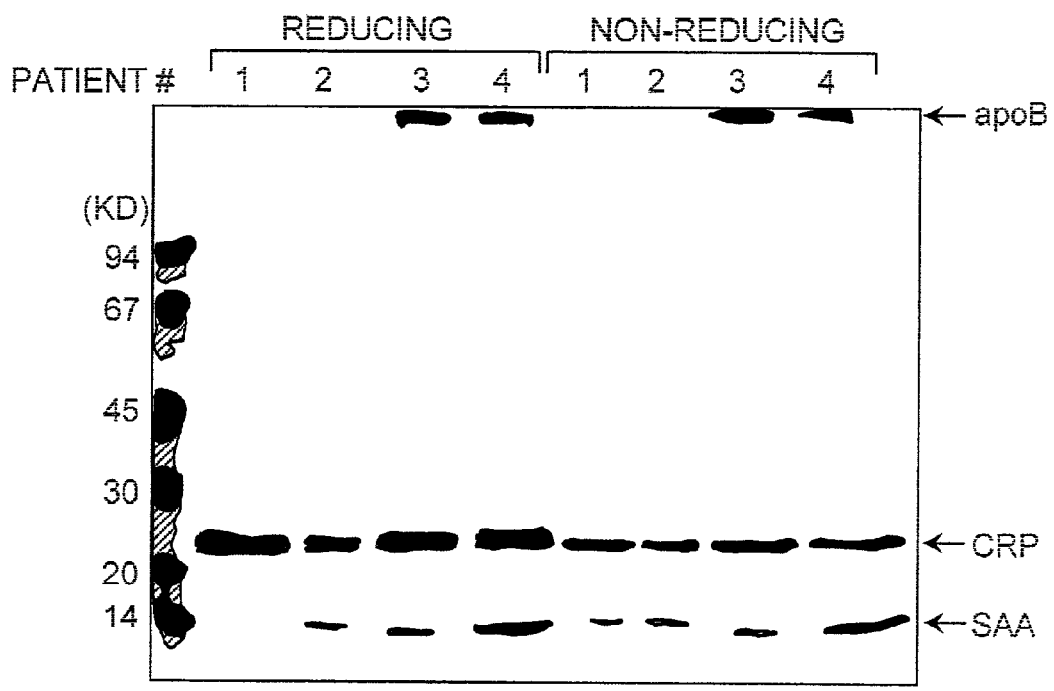
FIG. 33 is an SDS-PAGE gel of calcium precipitates from 4 DIC patients electrophoresed under reducing (lanes 1–4) or non-reducing (lanes 5–8) conditions. Approximately 5 μg of protein were loaded from patient #1 (lanes 1 and 5), patient # 2 (lanes 2 and 6), patient #3 (lanes 3 and 7), and patient #5 (lanes 4 and 8). After electrophoresis, the gel was stained with Coomassie Blue, destained, and dried.

FIG. 32 is a western blot and FIG. 33 is an SDS-PAGE gel of calcium precipitates isolated from DIC patients. FIG. 32 is a western blot of a 2.5–5% SDS-PAGE gel transferred and probed with a monoclonal antibody to apoB (present on VLDL, IDL and LDL). Lane 1 in FIG. 32 is normal human plasma, lanes 2–5 are DIC patient plasma, whereas lanes 6–9 are calcium precipitates from DIC patient plasmas isolated from patients studied in lanes 2–5, respectively. FIG. 33 is an 5–15% SDS-PAGE of calcium precipitates from four DIC patients electrophoresed under reducing (lanes 1–4) and non-reducing (lanes 5–8) conditions. Approximately 5 micrograms of protein was loaded from patient #1 (lanes 1, 5); patient #2 (lanes 2, 6); patient #3 (lanes 3, 7) and patient #4 (lanes 4, 8). After electrophoresis, the gel was stained in Coomassie Blue, destained and dried. CRP and SAA were identified by immunoblotting and apoB was identified by N-terminal sequencing and immunoblotting.

It was also found that the complex formation can be inhibited by phosphorylcholine, or phosphorylcholine with varying fatty acid side chains (e.g. phosphotidylcholine) or vesicles containing phosphorylcholine, phosphorylethanolamine, or phosphylethanolamine with varying fatty acid side chains (e.g. phosphotidylethanolamine) or vesicles containing phosphorylethanolamine, or EACA and the like. It is known that CRP binds directly to PC and that PC competes with lipoproteins for binding to CRP. Phosphotidylcholine was found to be a major phospholipid component in the complex.

PE, apo(A) and sphingomyelin were found to be minor components. It was also found that apo(B) can bind directly to CRP, however this is unlikely to occur in vivo (and thus is not likely to be contributing to complex formation) because apo(B) does not appear in plasma in a "free" form unattached to a lipoprotein.

Therefore, in a still further embodiment of the invention, a method is provided which includes adding one or more reagents (which may or may not cause coagulation) to a test sample from a patient in order to cause formation of a precipitate comprising an acute phase protein bound to a lipoprotein. Then, the binding of the acute phase protein to the lipoprotein is measured (either over time or as an endpoint). An inhibiting reagent is added before or after the complex-inducing reagent(s), which inhibiting reagent inhibits at least in part, the binding of the acute phase protein to the lipoprotein. The extent of inhibition is then determined (e.g. based on the amount of complex formed or not). The inhibiting reagent can be added after all or substantially all of the lipoprotein has become bound to the acute phase protein, or, the inhibiting reagent can be added even prior to adding the complex inducing reagent(s) (e.g. metal divalent cation such as calcium). The types of complex-inhibiting substances can be those such as mentioned above, or an apo-lipoprotein that binds to CRP such as apoB, or apoE, or EDTA, sodium citrate, or antibodies to epitopes involved in complex formation. The complex-inhibiting reagent should preferably inhibit, as an example, CRP bound to a chylomicron or chylomicron remnant, or LDL, VLDL or IDL. The method can be performed whereby the complex-causing reagent and/or the complex-inhibiting reagent are added at more than one concentration. This embodiment can be utilized to quantitate the amount of complex and/or establish the specificity of the complex. Due to the correlation of poor clinical outcome and complex formation, in one embodiment, the complex-inhibiting reagent can be used as a therapeutic to decrease the amount of complex in vivo.

Figure 42:
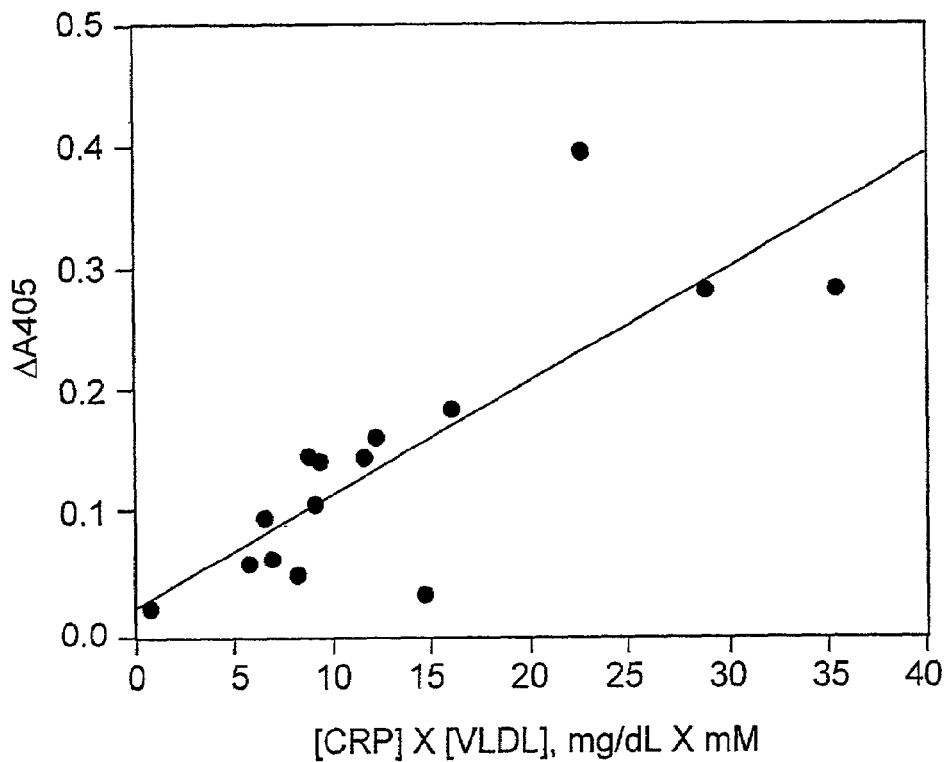
FIG. 42 is a graph depicting correlations between the level of CRP in complex with VLDL and the turbidity change upon recalcification of patient plasma samples. The total concentration of CRP and VLDL (cholesterol) in 15 patient plasmas were measured. The level of CRP in complex was calculated, using the parameters for complex formation measured in lipoprotein depleted normal plasma, supplemented with normal VLDL and recombinant CRP. The absorbance change at 405 nm (turbidity) was measured 20 minutes after adding $CaCl_2$ and the thrombin inhibitor PPACK to the samples.
Figure 43:
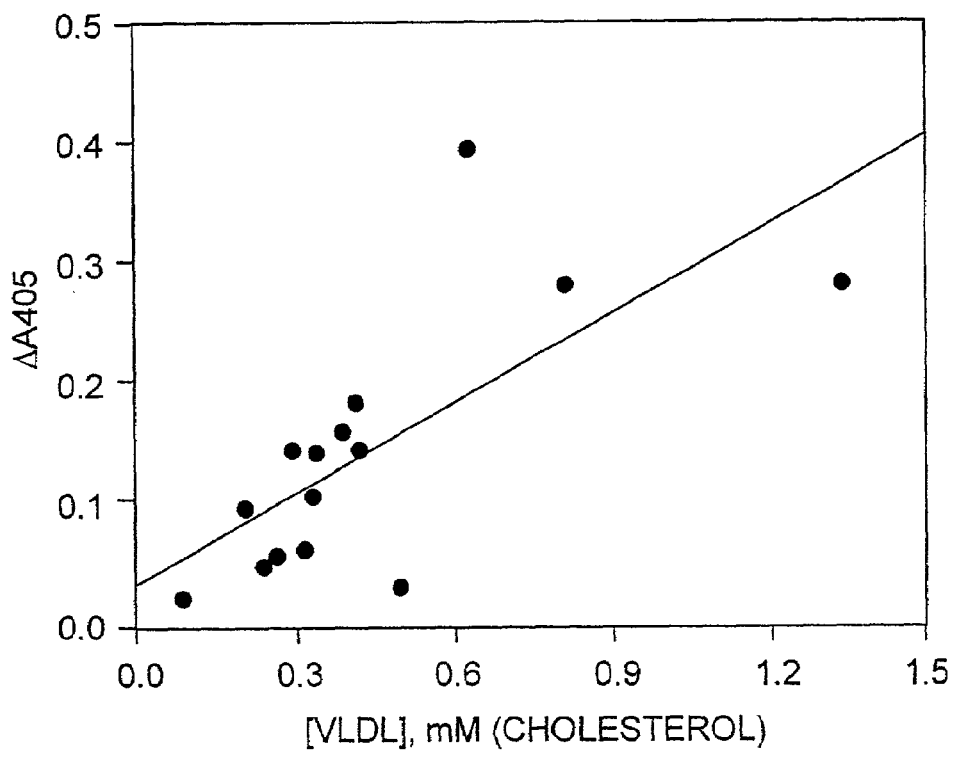
FIG. 43 is a graph depicting the correlation between the VLDL levels and turbidity changes upon recalcification of patient plasma versus varying VLDL concentration.

Though the primary invention is directed to detecting the complex and thereby predicting mortality, the invention is also directed to detecting total lipoprotein(s) that bind to CRP (and thus determining a total amount of certain lipoproteins in the sample). More specifically, an acute phase protein (such as CRP) is added to a test sample along with precipitate induces such as a divalent metal cation or a reagent to lower the pH at least below 7. The exogenous acute phase protein ensures that substantially all of the lipoprotein VLDL, as well as a majority of the LDL in the test sample, will form the complex/precipitate. Because the complex formation is much greater between CRP and VLDL and IDL, as compared to between CRP and LDL and HDL (see FIG. 42), in this embodiment, the complex formed by adding exogenous CRP can be correlated to total VLDL and/or VLDL+IDL levels. When adding additional CRP, the CRP can be isolated or purified CRP or recombinant CRP.

It should be understood that the present invention is useful for detecting complex formation in the absence of adding exogenous lipids to the test sample, or in the absence of adding exogenous lipids to the patient (e.g. intravenous administration of lipids such as Intralipid). Rather, the present invention is desirable for detecting a patient's own lipoproteins such as VLDL complexed with the patient's own acute phase protein(s) such as CRP. By measuring this "natural" lipoprotein-acute phase protein complex (rather than artificially causing the complex to form due to the addition of exogenous lipids), the test can be a helpful predictor of clinical outcome.

In a further embodiment of the invention the slope of the clot profile and/or the overall change in turbidity (e.g. as measured by optical-transmittance or absorbance) can be utilized to diagnose the condition of the patient. More particularly, one or more reagents are added to a test sample from a patient. The test sample should include at least a component of blood from the patient (e.g. plasma or serum could be used). The reagents are capable of causing the formation of the complex in vitro, which complex comprises at least one acute phase protein and at least one lipoprotein, while causing substantially no fibrin polymerization. The formation of the complex is measured over time so as to derive a time-dependent measurement profile. Then the slope and/or overall change in turbidity ("delta") are used to diagnose the condition of the patient (e.g. predict the likelihood of mortality of the patient).

In a still further embodiment of the invention, a method for testing therapeutics (or "test compound") or treatment agents includes providing a human or animal subject whose blood undergoes complex formation and administering a therapeutic to the human or animal subject whose blood shows evidence of complex formation. Then, a therapeutic is either administered to the subject or added to the test sample in vitro, followed by determining whether complex formation is increased, decreased or prevented entirely. If the therapeutic is administered to the patient, it is preferable that it be administered over time and that the complex formation (or lack thereof) be likewise monitored over time.

For the purposes of the foregoing, the terms "test compound" and "therapeutic" refer to an organic compound, drug, or pharmaceutically active agent, particularly one being tested to confirm effectiveness in a clinical trial on a human or animal (preferably mammalian such as dog, cat or rat) subject (rather than an approved therapeutic agent being used to treat a disease in a particular subject). The therapeutic may, in general, be an antibiotic agent, an anti-inflammatory agent, an anti-coagulant agent, a pro-coagulant agent, etc. In addition to clinical trial or drug testing use, the method may also be used in conjunction with an approved therapeutic agent-such as those described above to monitor the effectiveness of the therapeutic agent in a particular patient. Thus, if the particular therapeutic is early on discovered to be ineffective for a particular patient, an opportunity is provided to switch the patient to a different therapeutic which may prove to be more effective for that patient.

Table 12' shows CRP, VLDL, Slope 1 and the turbidity changes in 15 patients.

TABLE 12

| Patient # | Turbidity (ΔA405 nm) | Slope _1 X10$^5$ | CRP (μg/mL) | VLDL Cholesterol (mM) | VLDL Apo (B) (mM) | VLDL Total Protein (μg/mL) |
|---|---|---|---|---|---|---|
| 1 | 0.290 | 185 | 266 | 1.320 | 367.0 | 553.0 |
| 2 | 0.145 | 294 | 398 | 0.360 | 87.1 | 83.1 |
| 3 | 0.062 | 160 | 219 | 0.440 | 64.2 | 114.0 |
| 4 | 0.048 | 198 | 342 | 0.297 | 64.8 | 78.5 |
| 5 | 0.033 | 221 | 294 | 0.568 | 143.0 | 169.0 |
| 6 | 0.095 | 274 | 323 | 0.276 | 50.8 | 62.6 |
| 7 | 0.288 | 361 | 355 | 0.850 | 230.0 | 310.0 |
| 8 | 0.162 | 292 | 314 | 0.478 | 94.5 | 144.0 |
| 9 | 0.401 | 564 | 361 | 0.810 | 134.0 | 243.0 |
| 10 | 0.057 | 240 | 220 | 0.329 | 72.2 | 79.0 |
| 11 | 0.187 | 389 | 387 | 0.460 | 113.0 | 155.0 |
| 12 | 0.143 | 206 | 274 | 0.378 | 72.5 | 157.0 |
| 13 | 0.146 | 314 | 212 | 0.554 | 108.0 | 134.0 |
| 14 | 0.106 | 414 | 274 | 0.350 | 104.0 | 113.0 |
| 15 | 0.021 | 109 | 77 | 0.095 | 14.4 | 41.7 |

VLDL levels were measured 3 ways: 1) Total cholesterol, 2) ELISA for Apo(B), and 3) total protein by the Bradford assay.

FIGS. 37 through 50 illustrate further features of the present invention.

It is to be understood that the invention described and illustrated herein is to be taken as a preferred example of the same, and that various changes in the methods of the invention may be resorted to, without departing from the spirit of the invention or scope of the claims.

We claim:

1. A method for testing the effectiveness of a therapeutic for treatment of hemostatic dysfunction, comprising the steps of (a) providing a test sample from a patient with hemostatic dysfunction, (b) adding a divalent metal cation reagent to the test sample wherein the reagent does not cause fibrin formation, (c) measuring the formation of a complex comprising C reactive protein (CRP) and at least one human lipoprotein selected from the group consisting of very low density lipoprotein (VLDL) and intermediate density lipoprotein (IDL), (d) administering a therapeutic to said patient, (e) repeating the steps (a) through (d) at a later time, wherein a decrease in said complex formation at said later time is indicative of the efficacy of said therapeutic for treatment of hemostatic dysfunction.

2. The method of claim 1, wherein the hemostatic dysfunction is disseminated intravascular coagulation (DIC).

3. The method of claim 1, wherein the at least one human lipoprotein is a very low density lipoprotein (VLDL).

4. The method of claim 1, wherein the at least one human lipoprotein is an intermediate density lipoprotein (DL).

5. The method of claim 1, wherein the at least one human lipoprotein further comprises a chylomicron.

* * * * *

UNITED STATES PATENT AND TRADEMARK OFFICE
CERTIFICATE OF CORRECTION

| | |
|---|---|
| PATENT NO. | : 7,179,612 B2 |
| APPLICATION NO. | : 10/019087 |
| DATED | : February 20, 2007 |
| INVENTOR(S) | : Fischer et al. |

It is certified that error appears in the above-identified patent and that said Letters Patent is hereby corrected as shown below:

Column 4, Line 64: Please Correct "DIC (c, D)." To Read --DIC (C, D).--

Column 5, Line 55: Please Correct "changes ere" To Read --changes were--

Signed and Sealed this

Twenty-sixth Day of June, 2007

JON W. DUDAS
*Director of the United States Patent and Trademark Office*

UNITED STATES PATENT AND TRADEMARK OFFICE
CERTIFICATE OF CORRECTION

PATENT NO. : 7,179,612 B2  Page 1 of 1
APPLICATION NO. : 10/019087
DATED : February 20, 2007
INVENTOR(S) : Fischer et al.

It is certified that error appears in the above-identified patent and that said Letters Patent is hereby corrected as shown below:

In The Claims:
Column 24, Line 28 Claim 4:   Please Correct Claim 4 To Read: --The method of claim 1, wherein the at least one human lipoprotein is an intermediate density lipoprotein (IDL)--

Signed and Sealed this

Sixteenth Day of December, 2008

JON W. DUDAS
*Director of the United States Patent and Trademark Office*